(12) United States Patent
Anderskewitz et al.

(10) Patent No.: US 6,512,000 B1
(45) Date of Patent: Jan. 28, 2003

(54) AMINOCARBONYL-SUBSTITUTED BENZIMIDAZOLES HAVING TRYPTASE-INHIBITORY ACTIVITY

(75) Inventors: Ralf Anderskewitz, Bingen (DE); Christine Braun, Giubiasco (CH); Hans Briem, Ingelheim (DE); Bernd Disse, Mainz (DE); Christoph Hoenke, Ingelheim (DE); Hans Michael Jennewein, Wiesbaden (DE); Georg Speck, Ingelheim (DE)

(73) Assignee: Boehringer Ingelheim Pharma KG, Ingelheim (DE)

( * ) Notice: Subject to any disclaimer, the term of this patent is extended or adjusted under 35 U.S.C. 154(b) by 0 days.

(21) Appl. No.: 09/634,958

(22) Filed: Aug. 8, 2000

Related U.S. Application Data
(60) Provisional application No. 60/153,423, filed on Sep. 10, 1999.

(30) Foreign Application Priority Data

Aug. 20, 1999 (DE) .......................... 199 39 463

(51) Int. Cl.$^7$ .............................. A01N 43/50
(52) U.S. Cl. ................ 514/396; 514/218; 514/235.8; 514/273; 514/314; 514/317; 514/339; 544/153; 544/370; 540/492; 546/159; 546/199; 546/273.4
(58) Field of Search ............. 548/304.7, 305.1, 548/306.1; 540/492; 544/153, 370; 546/159, 199, 273.4; 514/218, 235.8, 273.4, 314, 317, 339, 394

(56) References Cited

U.S. PATENT DOCUMENTS 6,087,380 A  7/2000 Hauel et al. ............. 546/273.4

FOREIGN PATENT DOCUMENTS

WO  WO98 37075 A  8/1998

OTHER PUBLICATIONS

Corvera et al., Journal of Physiology 517(3), 741–756, 1999.*

* cited by examiner

Primary Examiner—Richard L. Raymond
Assistant Examiner—Venkataraman Balasubramanian
(74) Attorney, Agent, or Firm—Robert P. Raymond; Alan R. Stempel; Mary-Ellen M. Devlin

(57) ABSTRACT

A method for treating diseases in which tryptase inhibitors may be of thereapeutic value, which comprises the administration of a thereapeutic amount of a compound of the formula

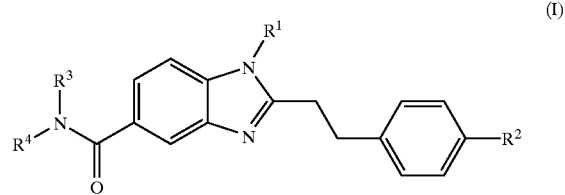

(I)

The invention also comprises novel compounds of the formula (I). Exemplary is 2-[2-(4-amidinophenyl)ethyl]-1-methyl-benzimidazol-5-yl-carboxylic acid-N-(pyridin-3-yl-methyl)-N-methyl-amide-hydrochloride.

17 Claims, No Drawings

AMINOCARBONYL-SUBSTITUTED BENZIMIDAZOLES HAVING TRYPTASE-INHIBITORY ACTIVITY

RELATED APPLICATIONS

Benefit of U.S. Provisional Application Serial No. 60/153,423, filed on Sep. 10, 1999, is hereby claimed.

FIELD OF THE INVENTION

The invention relates to the use of certain aminocarbonyl-substituted benzimidazole derivatives for the treatment of diseases in which inhibition of tryptase is of therapeutic value, certain novel aminocarbonyl-substituted benzimidazole derivatives having tryptase-inhibitory activity, methods for preparing their preparation and pharmaceutical compositions containing such compounds.

BACKGROUND OF THE INVENTION

Benzimidazole derivatives are known from the prior art as active substances with valuable pharmaceutical properties. Thus, International Patent Application WO 98/37075 discloses, in addition to other bicyclic heterocycles, benzimidazoles, which can be used to good effect, on the basis of their thrombin-inhibiting activity, to prevent and treat venous and arterial thrombotic diseases.

In contrast to the use of benzimidazole derivatives described hereinbefore and known from the prior art, the aim of the present invention is to prepare new tryptase inhibitors which can be used, by virtue of their tryptase-inhibiting properties, to prevent and treat inflammatory and/or allergic diseases.

DETAILED DESCRIPTION OF THE INVENTION

It has been found, surprisingly, that aminocarbonyl-substituted benzimidazole derivatives of general formula (I)

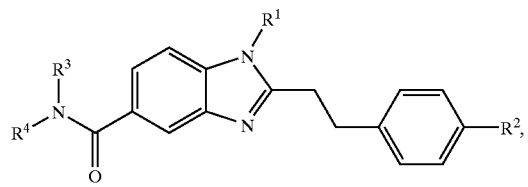

(I)

wherein the groups $R^1$, $R^2$, $R^3$ and $R^4$ may have the meanings given hereinafter, have a tryptase-inhibiting effect and may be used according to the invention for the prevention and treatment of diseases in which tryptase inhibitors may be of therapeutic value.

Thus, a first aspect of the invention is a method for treating diseases in which tryptase inhibitors may be of thereapeutic value, which method comprises the administration, to a host in need of such treatment, of a thereapeutic amount of a compound of the formula (I)

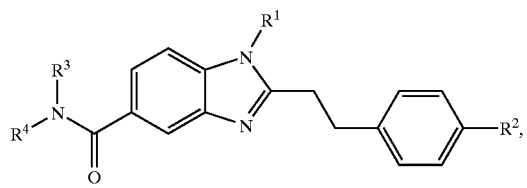

(I)

wherein:
$R^1$ denotes $C_1$–$C_{10}$-alkyl, which may optionally be mono-, di- or tri-substituted by one or more of the groups $C_1$–$C_4$-alkoxy, phenoxy, hydroxyphenoxy, $C_1$–$C_4$-alkoxy-phenoxy, $C_3$–$C_6$-cycloalkyl, —$NH_2$, —NH($C_1$–$C_4$-alkyl), —N($C_1$–$C_4$-alkyl)$_2$, —NH—CO—($C_1$–$C_4$-alkyl), —CO—$NH_2$, —CO—NH—($C_1$–$C_4$-alkyl) or —NH—CO-benzyl, or phenyl-$C_1$–$C_4$-alkyl, wherein the phenyl ring may optionally be mono-, di- or tri-substituted by one or more of the groups $C_1$–$C_4$-alkyl, $CF_3$, fluorine, chlorine, bromine, COOH or COO—$C_1$–$C_4$-alkyl, or a 5 or 6 membered, saturated or unsaturated heterocyclic group linked via a single bond or via a $C_1$–$C_4$-alkylene bridge, which may contain one, two or three heteroatoms selected from the group comprising oxygen, nitrogen or sulphur and which may optionally be mono-, di- or tri-substituted by one or more of the groups $C_1$–$C_4$-alkyl, optionally by $C_1$–$C_4$-alkyl substituted phenyl or optionally by $C_1$–$C_4$-alkyl substituted benzyl or to which a benzene ring may optionally be fused via two adjacent carbon atoms;

$R^2$ denotes —C(=NH)$NH_2$ or —$CH_2$—$NH_2$;

$R^3$ and $R^4$ which may be identical or different, denote hydrogen, $C_1$–$C_6$-alkyl, which may be mono- or disubstituted by one or more of the groups COOH, COO—$C_1$–$C_4$-alkyl, $C_3$–$C_6$-cycloalkyl, —$NH_2$, —NH($C_1$–$C_4$-alkyl), —N($C_1$–$C_4$-alkyl)$_2$, —NHphenyl, —N(phenyl)$_2$, —NHbenzyl, —N(benzyl)$_2$, —NH—CO—($C_1$–$C_4$-alkyl), —C(=NH)$NH_2$ or —NH—C(=NH)$NH_2$, or phenyl-$C_1$–$C_4$-alkyl, wherein the $C_1$–$C_4$-alkylene bridge may optionally be substituted by phenyl, COOH or COO—$C_1$–$C_4$-alkyl and wherein the phenyl ring may optionally be mono-, di- or tri-substituted, directly or via a $C_1$–$C_4$-alkylene bridge, by one or more of the groups $C_1$–$C_4$-alkyl, $C_1$–$C_4$-alkoxy, $CF_3$, fluorine, chlorine, bromine, COOH, COO—$C_1$–$C_4$-alkyl, —$NH_2$, —NH($C_1$–$C_4$-alkyl), —N($C_1$–$C_4$-alkyl)$_2$, —NHphenyl, —N(phenyl)$_2$, —NHbenzyl, —N(benzyl)$_2$, —NH—CO—($C_1$–$C_4$-alkyl), —C(=NH)$NH_2$ or —NH—C(=NH)$NH_2$, or a 5-, 6- or 7-membered, saturated or unsaturated heterocyclic group linked directly or via a $C_1$–$C_4$-alkylene bridge, which may contain one, two, three or four heteroatoms selected from the group comprising oxygen, nitrogen or sulphur and which may optionally be mono-, di- or tri-substituted by one or more of the groups $C_1$–$C_4$-alkyl, phenyl or benzyl or to which a benzene ring may optionally be fused via two adjacent carbon atoms, or $C_3$–$C_8$-cycloalkyl, naphthyl or phenyl, which may optionally be mono-, di- or tri-substituted by one or more of the groups $C_1$–$C_4$-alkyl, $C_1$–$C_4$-alkoxy, phenyloxy, benzyloxy, $CF_3$, fluorine, chlorine, bromine, COOH or COO—$C_1$–$C_4$-alkyl, or $R^3$ and $R^4$ together with the nitrogen atom form a 5-, 6- or 7-membered, saturated or unsaturated heterocyclic group, which may contain one or two further heteroatoms selected from the group comprising oxygen, nitrogen or sulphur and which may optionally be substituted by one or more of the groups $C_1$–$C_4$-alkyl, $C_5$–$C_6$-cycloalkyl, benzyl, which may optionally be substituted by $C_1$–$C_4$-alkyl, pyridyl or phenyl, optionally substituted by $C_1$–$C_4$-alkyl, $C_1$–$C_4$-alkoxy or hydroxy, or a tautomer or pharmacologically acceptable acid addition salt thereof.

The phrase "a host in need of such treatment" as used herein means a patient, whether animal or human, which or who suffers from a disease which is treatable by the inhibition of tryptase.

The above-described thereapeutic method may be used to treat inflammatory and/or allergic diseases. Even more particularly, the above-described method may be used for the treatment of bronchial asthma, allergic rhinitis, allergic conjunctivitis, atopic dermatitis, urticaria, allergic otitis, allergic gastro-intestinal disorders, Crohn's disease, ulcerative colitis, anaphylactic shock, septic shock, shock lung (ARDS) and arthritis.

The compounds of formula (I) as described above for may also be used, in accordance with the invention, for the treatment of fibroses such as lung fibrosis, fibrosing alveolitis and scarring, collagenoses such as lupus erythematodes and sclerodermia as well as arteriosclerosis, psoriasis and neoplasm.

Some of the above-described compounds of the formula (I) are known and others are novel. These novel compounds of formula (I) constitute a second aspect of the invention.

The novel compounds provided by the invention are those of the formula (I)

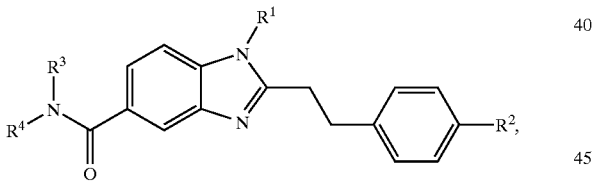

(I)

wherein

R denotes $C_1$–$C_{10}$-alkyl, which may optionally be mono-, di- or tri-substituted by one or more of the groups $C_1$–$C_4$-alkoxy, phenoxy-, $C_1$–$C_4$-alkoxy-phenoxy, hydroxyphenoxy, $C_3$–$C_6$-cycloalkyl, —$NH_2$, —NH($C_1$–$C_4$-alkyl), —N($C_1$–$C_4$-alkyl)$_2$, —NH—CO—($C_1$–$C_4$-alkyl), —CO—$NH_2$, —CO—NH—($C_1$–$C_4$-alkyl) or —NH—CO-benzyl, or phenyl-$C_1$–$C_4$-alkyl, wherein the phenyl ring may optionally be mono-, di- or tri-substituted by one or more of the groups $C_1$–$C_4$-alkyl, $CF_3$, fluorine, chlorine, bromine, COOH or COO—$C_1$–$C_4$-alkyl, or a 5 or 6 membered, saturated or unsaturated heterocyclic group linked via a single bond or via a $C_1$–$C_4$-alkylene bridge, which may contain one, two or three heteroatoms selected from the group comprising oxygen, nitrogen or sulphur and may optionally be mono-, di- or tri-substituted by one or more of the groups $C_1$–$C_4$-alkyl, optionally by $C_1$–$C_4$-alkyl substituted phenyl or optionally by $C_1$–$C_4$-alkyl substituted benzyl, or to which a benzene ring may optionally be fused via two adjacent carbon atoms;

$R^2$ denotes —C(=NH)$NH_2$ or —$CH_2$—$NH_2$;

$R^3$ denotes $C_1$–$C_6$-alkyl, which is mono- or disubstituted by one or more of the groups —$NH_2$, —NH($C_1$–$C_4$-alkyl), —N($C_1$–$C_4$-alkyl)$_2$, —NHphenyl, —N(phenyl)$_2$, —NHbenzyl, —N(benzyl)$_2$, —NH—CO—($C_1$–$C_4$-alkyl), —C(=NH)$NH_2$ or —NH—C(=NH)$NH_2$, or benzyl, wherein the phenyl ring is mono- or disubstituted, directly or via a $C_1$–$C_4$-alkylene bridge, by one or more of the groups —$NH_2$, —NH($C_1$–$C_4$-alkyl), —N($C_1$–$C_4$-alkyl)$_2$, —NHphenyl, —N(phenyl)$_2$, —NHbenzyl, —N(benzyl)$_2$, —NH—CO—($C_1$–$C_4$-alkyl), —C(=NH)$NH_2$ or —NH—C(=NH)$NH_2$, or phenyl-$C_2$–$C_4$-alkyl, wherein the $C_2$–$C_4$-alkylene bridge may optionally be substituted by phenyl, COOH or COO—$C_1$–$C_4$-alkyl and wherein the phenyl ring may optionally be mono- or di-substituted, directly or via a $C_1$–$C_4$-alkylene bridge, by one or more of the groups —$NH_2$, —NH($C_1$–$C_4$-alkyl), —N($C_1$–$C_4$-alkyl)$_2$, —NHphenyl, —N(phenyl)$_2$, —NHbenzyl, —N(benzyl)$_2$, —NH—CO—($C_1$–$C_4$-alkyl), —C(=NH)$NH_2$ or —NH—C(=NH)$NH_2$, or a 5 or 6 membered, saturated or unsaturated heterocyclic group linked via a $C_1$–$C_4$-alkylene bridge, which may contain one, two or three heteroatoms selected from the group comprising oxygen, nitrogen or sulphur and which may optionally be mono-, di- or tri-substituted by one or more of the groups $C_1$–$C_4$-alkyl, phenyl or benzyl;

$R^4$ denotes hydrogen, $C_1$–$C_6$-alkyl, which may be mono- or disubstituted by one or more of the groups COOH, COO—$C_1$–$C_4$-alkyl or $C_3$–$C_6$-cycloalkyl, or phenyl-$C_1$–$C_4$-alkyl, wherein the $C_1$–$C_4$-alkylene bridge may optionally be substituted by phenyl and wherein the phenyl ring may optionally be mono-, di- or tri-substituted by one or more of the groups $C_1$–$C_4$-alkyl, $C_1$–$C_4$-alkoxy, $CF_3$, fluorine, chlorine, bromine, COOH or COO—$C_1$–$C_4$-alkyl, or $C_3$–$C_8$-cycloalkyl, naphthyl or phenyl, which may optionally be mono-, di- or tri-substituted by one or more of the groups $C_1$–$C_4$-alkyl, $C_1$–$C_4$-alkoxy, phenyloxy, benzyloxy, $CF_3$, fluorine, chlorine, bromine, COOH or COO—$C_1$–$C_4$-alkyl, or a 5-, 6- or 7-membered, saturated or unsaturated heterocyclic group linked via a $C_1$–$C_4$-alkylene bridge, which contains a heteroatom selected from the group comprising oxygen, nitrogen or sulphur and which may optionally be mono-, di- or tri-substituted by one or more of the groups $C_1$–$C_4$-alkyl, phenyl or benzyl or to which a benzene ring may optionally be fused via two adjacent carbon atoms, or $R^3$ and $R^4$ together with the nitrogen atom form a 5-, 6- or 7-membered, saturated or unsaturated heterocyclic group, which contains one or two further heteroatoms selected from the group comprising oxygen, nitrogen or sulphur and may optionally be substituted by one or more of the groups $C_1$–$C_4$-alkyl; benzyl, which is optionally $C_1$–$C_4$-alkyl-substituted, $C_{5-C6}$-cycloalkyl, pyridyl or phenyl, which optionally bears a group selected from the group comprising $C_1$–$C_4$-alkyl, $C_1$–$C_4$-alkoxy or hydroxy, and tautomers and pharmacologically acceptable acid addition salts thereof.

Preferred are compounds of general formula (I), wherein
$R^1$ denotes unsubstituted $C_1$–$C_{10}$-alkyl, or
may be mono- or disubstituted by $C_1$–$C_4$-alkoxy, phenoxy, $C_1$–$C_4$-alkoxy-phenoxy, hydroxyphenoxy, $C_3$–$C_6$-cycloalkyl, —$NH_2$, —$NH(C_1$–$C_4$-alkyl), —$N(C_1$–$C_4$-alkyl)_2$, —NH—CO—$(C_1$–$C_4$-alkyl), —CO—$NH_2$, —CO—NH—$(C_1$–$C_4$-alkyl) or NH—CO-benzyl substituted $C_1$–$C_4$-alkyl, or phenyl-$C_1$–$C_3$-alkyl, wherein the phenyl ring may optionally be mono- or disubstituted by $C_1$–$C_4$-alkyl, $CF_3$, fluorine, chlorine, bromine, COOH or COO—$C_1$–$C_4$-alkyl, or a 5-, 6- or 7-membered, saturated or unsaturated heterocyclic group linked via a $C_1$–$C_3$-alkylene bridge, which may contain one or two heteroatoms selected from the group comprising oxygen, nitrogen or sulphur and may optionally be mono- or disubstituted by one or more of the groups methyl, ethyl, propyl, phenyl, methylphenyl- or benzyl or to which a benzene ring may optionally be fused via two adjacent carbon atoms;

$R^2$ denotes —C(=NH)$NH_2$ or —$CH_2$—$NH_2$;

$R^3$ denotes $C_1$–$C_6$-alkyl, which is mono- or disubstituted by one or more of the groups —$NH_2$, —$NH(C_1$–$C_4$-alkyl), —$N(C_1$–$C_4$-alkyl)_2$, —NHphenyl, —N(phenyl)$_2$, —NHbenzyl, —N(benzyl)$_2$, —NH—CO—$(C_1$–$C_4$-alkyl), —C(=NH)$NH_2$ or —NH—C(=NH)$NH_2$, or benzyl, wherein the phenyl ring is substituted directly or via a $C_1$–$C_4$-alkylene bridge by one of the groups —$NH_2$, —$NH(C_1$–$C_4$-alkyl), —$N(C_1$–$C_4$-alkyl)_2$, —NHphenyl, —N(phenyl)$_2$, —NHbenzyl, —N(benzyl)$_2$, —NH—CO—$(C_1$–$C_4$-alkyl), —C(=NH)$NH_2$ or —NH—C(=NH)$NH_2$, or phenyl-$C_2$–$C_4$-alkyl, wherein the $C_2$–$C_4$-alkylene bridge may optionally be substituted by phenyl, COOH or COO—$C_1$–$C_4$-alkyl and wherein the phenyl ring may be substituted directly or via a $C_1$–$C_4$-alkylene bridge by one of the groups —$NH_2$, —$NH(C_1$–$C_4$-alkyl), —$N(C_1$–$C_4$-alkyl)_2$, —NHphenyl, —N(phenyl)$_2$, —NHbenzyl, —N(benzyl)$_2$, —C(=NH)$NH_2$ or —NH—C(=NH)$NH_2$, or a 5-, 6- or 7-membered, saturated or unsaturated heterocyclic group linked via a $C_1$–$C_4$-alkylene bridge, which may contain one or two heteroatoms selected from the group comprising oxygen or nitrogen and may optionally be mono- or disubstituted by one or more of the groups methyl, ethyl, propyl, phenyl or benzyl;

$R^4$ hydrogen, $C_1$–$C_4$-alkyl, which may be substituted by one of the groups COOH, COO—$C_1$–$C_4$-alkyl or $C_3$–$C_6$-cycloalkyl, or phenyl-$C_1$–$C_4$-alkyl, wherein the $C_1$–$C_4$-alkylene bridge may optionally be substituted by phenyl and wherein the phenyl ring may optionally be mono- or disubstituted by one or more of the groups $C_1$–$C_4$-alkyl, $C_1$–$C_4$-alkoxy, $CF_3$, fluorine, chlorine, bromine, COOH or COO—$C_1$–$C_4$-alkyl, or $C_3$–$C_8$-cycloalkyl, naphthyl or phenyl, which may optionally be mono- or disubstituted by one or more of the groups $C_1$–$C_4$-alkyl, $C_1$–$C_4$-alkoxy, phenyloxy, benzyloxy, $CF_3$, fluorine, chlorine, bromine, COOH or COO—$C_1$–$C_4$-alkyl, or a 5-, 6- or 7-membered, saturated or unsaturated heterocyclic group linked via a $C_1$–$C_4$-alkylene bridge, which contains a heteroatom selected from the group comprising oxygen, nitrogen or sulphur and which may optionally be mono- or disubstituted by one or more of the groups methyl, ethyl, propyl, phenyl or benzyl or to which a benzene ring may optionally be fused via two adjacent carbon atoms, or $R^3$ and $R^4$ together with the nitrogen atom form a 6- or 7-membered, saturated or unsaturated heterocyclic group, which contains one or two further heteroatoms selected from the group comprising oxygen or nitrogen and which may optionally be substituted by one or more of the groups methyl, ethyl, propyl, benzyl, cyclopentyl, cyclohexyl, pyridyl or phenyl, which optionally carries a group selected from the group comprising methyl, methoxy, ethoxy, propyloxy or hydroxy, and tautomers and pharmacologically acceptable acid addition salts thereof.

More preferred are compounds of general formula (I), wherein $R^1$ denotes unsubstituted $C_1$–$C_{10}$-alkyl, or by $C_1$–$C_4$-alkoxy, phenoxy, $C_1$–$C_4$-alkoxy-phenoxy, hydroxyphenoxy, $C_3$–$C_6$-cycloalkyl, —$NH_2$, —NH $(C_1$–$C_4$-alkyl), —$N(C_1$–$C_4$-alkyl)$_2$, —NH—CO—$(C_1$–$C_4$-alkyl), —CO—$NH_2$, —CO-NH—$(C_1$–$C_4$-alkyl) or —NH—CO-benzyl substituted $C_1$–$C_4$-alkyl, or phenyl-$C_1$–$C_3$-alkyl, wherein the phenyl ring may optionally be mono- or disubstituted by $C_1$–$C_4$-alkyl, $CF_3$, fluorine, chlorine, bromine, COOH or COO—$C_1$–$C_4$-alkyl, or a heterocyclic group linked via a $C_1$–$C_3$-alkylene bridge, optionally mono- or disubstituted by one or more of the groups methyl, ethyl, propyl, phenyl, methylphenyl or benzyl, selected from the group comprising pyrrole, pyrroline, pyrrolidine, pyridine, piperidine, pyrimidine, piperazine, morpholine, thiomorpholine, imidazole, imidazoline, imidazolidine, pyrazole, pyrazoline, pyrazolidine, triazole, furan, tetrahydrofuran, α-pyran, γ-pyran, dioxolan, tetrahydropyran, dioxane, thiophene, dihydrothiophene, thiolan, dithiolan, oxazole, isoxazole, thiazole, isothiazole, oxadiazole, benzodioxole, benzimidazole, benzothiophene, benzofuran or indole;

$R^2$ denotes —C(=NH)$NH_2$ or —$CH_2$—$NH_2$;

$R^3$ denotes $C_1$–$C_3$-alkyl, which is substituted by —$NH_2$, —$NH(C_1$–$C_3$-alkyl), —$N(C_1$–$C_3$-alkyl)$_2$, —NHphenyl, —N(phenyl)$_2$, —NHbenzyl, —N(benzyl)$_2$, —NH—CO—$(C_1$–$C_3$-alkyl), —C(=NH)$NH_2$ or —NH—C(=NH)$NH_2$, or benzyl, wherein the phenyl ring is substituted directly or via a methylene bridge by one of the groups —$NH_2$, —$NH(C_1$–$C_3$-alkyl), —$N(C_1$–$C_4$-alkyl)$_2$, —NHphenyl, —N(phenyl)$_2$, —NHbenzyl, —N(benzyl)$_2$, —NH—CO—$(C_1$–$C_3$-alkyl), —C(=NH)$NH_2$ or —NH—C(=NH)$NH_2$, or phenyl-$C_2$–$C_3$-alkyl, wherein the $C_2$–$C_3$-alkylene bridge may optionally be substituted by phenyl, COOH or COO—$C_1$–$C_3$-alkyl and wherein the phenyl ring may be substituted directly or via a methylene bridge by one of the groups —$NH_2$, —NH $(C_1$–$C_3$-alkyl), —$N(C_1$–$C_3$-alkyl)$_2$, —NHphenyl, —N(phenyl)$_2$, —NHbenzyl, —N(benzyl)$_2$, —C(=NH)$NH_2$ or —NH—C(=NH)$NH_2$, or a heterocyclic group linked via a $C_1$–$C_3$-alkylene bridge, optionally mono- or disubstituted by one or more of the groups methyl, ethyl, propyl, phenyl or benzyl, selected from the group comprising pyrrole, pyrroline, pyrrolidine, pyridine, piperidine, pyrimidine, piperazine morpholine, diazepan, imidazole, imidazoline, imidazolidine, pyrazole, pyrazoline, pyrazolidine, furan, tetrahydrofuran, α-pyran, γ-pyran, dioxolan, tetrahydropyran, dioxane, oxazole or isoxazole;

$R^4$ denotes hydrogen, $C_1$–$C_4$-alkyl, which may be substituted by one of the groups COOH, COO—$C_1$–$C_3$-alkyl or $C_3$–$C_6$-cycloalkyl, or phenyl-$C_1$–$C_3$-alkyl, wherein the $C_1$–$C_3$-alkylene bridge may optionally be substituted by phenyl and wherein the phenyl ring may optionally be substituted by $C_1$–$C_3$-alkyl, $C_1$–$C_3$-alkoxy, $CF_3$, fluorine, chlorine, bromine, COOH or COO—$C_1$–$C_3$-alkyl, or $C_3$–$C_8$-cycloalkyl, naphthyl or phenyl, which may optionally be mono- or disubstituted by one or more of the groups $C_1$–$C_3$-alkyl, $C_1$–$C_3$-alkoxy, phenyloxy, benzyloxy, $CF_3$, fluorine, chlorine, bromine, COOH or COO—$C_1$–$C_3$-alkyl, or a heterocyclic group linked via a $C_1$–$C_3$-alkylene bridge, optionally mono- or disubstituted by one or more of the groups methyl, ethyl, propyl, phenyl, methylphenyl- or benzyl, selected from the group comprising pyrrole, pyrroline, pyrrolidine, pyridine, piperidine, pyrimidine, piperazine morpholine, thiomorpholine, imidazole, imidazoline, imidazolidine, pyrazole, pyrazoline, pyrazolidine, triazole, furan, tetrahydrofuran, α-pyran, γ-pyran, dioxolan, tetrahydropyran, dioxane, thiophene, dihydrothiophene, thiolan, dithiolan, oxazole, isoxazole, thiazole, isothiazole, oxadiazole, benzodioxole, benzimidazole, benzothiophene, benzofuran or indole; or $R^3$ and $R^4$ together with the nitrogen atom form a 6- or 7-membered, saturated heterocyclic group, which contains one or two further nitrogen heteroatoms and which may optionally be substituted by one or more of the groups methyl, ethyl, propyl, benzyl, cyclopentyl, cyclohexyl, pyridyl or phenyl, which optionally carries a group selected from the group comprising methyl, methoxy, ethoxy, propyloxy or hydroxy, and tautomers and pharmacologically acceptable acid addition salts thereof.

Still more preferred are compounds of general formula (I), wherein $R^1$ denotes methyl, ethyl, propyl, butyl, pentyl, hexyl, heptyl, octyl, nonyl or decyl, or a methyl, ethyl or propyl group which is substituted by methoxy, ethoxy, cyclopropyl, cyclopentyl, cyclohexyl, phenyl, methoxyphenoxy, —$NH_2$, —NH($C_1$–$C_4$-alkyl), —N($C_1$–$C_4$-alkyl)$_2$, —NH—CO-methyl, —CO—$NH_2$, —CO—NH-methyl or —NH—CO-benzyl, or benzyl, which is mono- or disubstituted by methyl, ethyl, propyl, $CF_3$, fluorine, chlorine, bromine, COOH, COOMe or COOEt, or phenylethyl, which is mono- or disubstituted by methyl, ethyl, propyl, $CF_3$, fluorine, chlorine, bromine, COOH, COOMe or COOEt, or a heterocyclic group linked via a methylene, ethylene or propylene bridge, optionally mono- or disubstituted by one or more of the groups methyl, ethyl, propyl, phenyl, methylphenyl or benzyl, selected from the group comprising pyrrole, pyrrolidine, pyridine, piperidine, piperazine, morpholine, furan, tetrahydrofuran, thiophene, benzodioxole or benzimidazole;

$R^2$ denotes —C(=NH)$NH_2$ or —$CH_2$—$NH_2$;

$R^3$ denotes a methyl, ethyl or propyl group which is substituted by —$NH_2$, —NH($C_1$–$C_3$-alkyl), —N($C_1$–$C_3$-alkyl)$_2$, —NHphenyl, —N(phenyl)$_2$, —NHbenzyl, —N(benzyl)$_2$, —NH—CO—($C_1$–$C_3$-alkyl), —NH-benzyl or —C(=NH)$NH_2$, or benzyl, which is substituted directly or via a methylene bridge by one of the groups —$NH_2$, —NH($C_1$–$C_3$-alkyl), —N($C_1$–$C_4$-alkyl)$_2$, —NHphenyl, —N(phenyl)$_2$, —NHbenzyl, —N(benzyl)$_2$, —NH—CO—($C_1$–$C_3$-alkyl) or —C(=NH)$NH_2$, or phenyl-$C_2$–$C_3$-alkyl, wherein the $C_2$–$C_3$-alkylene bridge may optionally be substituted by phenyl, COOH or COO—$C_1$–$C_3$-alkyl and wherein the phenyl ring may be substituted directly or via a methylene bridge by one of the groups —$NH_2$, —NH($C_1$–$C_3$-alkyl), —N($C_1$–$C_3$-alkyl)$_2$, —NHphenyl, —N(phenyl)$_2$, —NHbenzyl, —N(benzyl)$_2$ or —C(=NH)$NH_2$, or a heterocyclic group linked via a methylene, ethylene or propylene bridge, optionally mono- or disubstituted by methyl, ethyl, propyl, phenyl or benzyl, selected from the group comprising pyrrole, pyrrolidine, pyridine, piperidine, piperazine, morpholine, diazepan, furan, tetrahydrofuran, thiophene, benzodioxole or benzimidazoles;

$R^4$ denotes hydrogen or a methyl, ethyl, propyl or butyl group which may be substituted by one of the groups COOH, COOMe, COOEt, cyclopropyl, cyclopentyl or cyclohexyl, or benzyl, which may optionally be substituted by methyl, ethyl, propyl, methoxy, ethoxy, $CF_3$, fluorine, chlorine, bromine, COOH, COOMe or COOEt, or phenylethyl, phenylpropyl, diphenylpropyl;

cyclopropyl, cyclopentyl, cyclohexyl, cyclooctyl, naphthyl or phenyl, which may optionally be substituted by methyl, ethyl, propyl, methoxy, ethoxy, phenyloxy, benzyloxy, $CF_3$, fluorine, chlorine, bromine, COOH, COOMe or COOEt, or a heterocyclic group linked via a methylene, ethylene or propylene bridge, optionally mono- or disubstituted by methyl, ethyl, propyl, phenyl or benzyl, selected from the group comprising pyrrole, pyrrolidine, pyridine, piperidine, piperazine, morpholine, furan, tetrahydrofuran, thiophene, quinoline, isoquinoline, benzodioxole or benzimidazole; or $R^3$ and $R^4$ together with the nitrogen atom form a piperazine or diazepan ring which may optionally be substituted by one of the groups methyl, ethyl, propyl, cyclopentyl, cyclohexyl, pyridyl, benzyl or phenyl, which optionally carries a group selected from the group comprising methyl, methoxy ethoxy, propyloxy or hydroxy, and tautomers and pharmacologically acceptable acid addition salts thereof.

Especially preferred according to the invention are compounds of general formula (I), wherein $R^1$ denotes methyl, ethyl, propyl, pentyl or n-decyl, or a methyl, ethyl- or propyl group which is substituted by methoxy, ethoxy, cyclopropyl, cyclopentyl, cyclohexyl, phenyl or methoxyphenoxy, or benzyl, which is mono- or disubstituted by methyl, $CF_3$, COOH, COOMe or COOEt, or a tetrahydrofuran linked via a methylene bridge;

$R^2$ denotes —C(=NH)NH$_2$ or —CH$_2$—NH$_2$;

$R^3$ denotes an ethyl or propyl group which is substituted by —NH$_2$, —NHMe, —NMe$_2$, —NHEt, —NEt$_2$, —NHphenyl, —N(phenyl)$_2$, —NHbenzyl, —N(benzyl)$_2$ or —C(=NH)NH$_2$, or benzyl which is substituted by one of the groups —NH$_2$, —CH$_2$—NH$_2$, —NMe$_2$, —NHMe, —NEt$_2$, —NHEt, —NH—CO-Me, —CH$_2$—NH—CO—Me or —C(=NH)NH$_2$, or phenylethyl, wherein the ethylene bridge may be substituted by COOH, COOMe or COOEt and wherein the phenyl ring is optionally substituted by one of the groups —NH$_2$, —CH$_2$—NH$_2$, —NMe$_2$, —NHMe, —NEt$_2$, —NHEt, —NH—CO-Me, —CH$_2$—NH—CO-Me or —C(=NH)N$_2$, or phenylpropyl, diphenylpropyl or pyridylmethyl;

$R^4$ denotes hydrogen or a methyl, ethyl, propyl or butyl group, which may be substituted by one of the groups COOH, COOMe, COOEt, cyclopropyl, cyclopentyl or cyclohexyl, or benzyl, which may optionally be substituted by methyl, ethyl, propyl, methoxy, ethoxy, CF$_3$, fluorine, chlorine, bromine, COOH, COOMe or COOEt, or phenyl-ethyl, phenylpropyl, diphenylpropyl, or cyclopentyl, cyclohexyl, cyclooctyl, naphthyl or phenyl, which may optionally be substituted by methyl, ethyl, methoxy, ethoxy, phenyloxy or CF$_3$, or a pyridine or quinoline linked via a methylene bridge, or $R^3$ and $R^4$ together with the nitrogen atom form a piperazine or diazepan ring, which may optionally be substituted by one of the groups cyclopentyl, cyclohexyl, pyridyl, benzyl or phenyl, which optionally carries one of the groups selected from the group comprising methyl, methoxy, ethoxy, propyloxy or hydroxy, and tautomers and pharmacologically acceptable acid addition salts thereof.

More especially preferred according to the invention are compounds of general formula (I), wherein $R^1$ denotes methyl, ethyl, propyl, pentyl, phenylethyl, phenylpropyl, cyclopropylmethyl, tetrahydrofuranylmethyl or benzyl, which is mono- or disubstituted by CF$_3$, COOH, COOMe or COOEt;

$R^2$ denotes —C(=NH)NH$_2$ or —CH$_2$—NH$_2$, preferably —C(=NH)NH$_2$;

$R^3$ denotes an ethyl or propyl group which is substituted by —NH$_2$, —NHMe, —NMe$_2$, —NHEt, —NEt$_2$, —NHphenyl, —N(phenyl)$_2$, —NHbenzyl, —N(benzyl)$_2$ or —C(=NH)NH$_2$, or benzyl substituted by one of the groups —NH$_2$, —CH$_2$—NH$_2$, —NMe$_2$, —NHMe, —NEt$_2$, —NHEt, —NH—CO-Me, —CH$_2$—NH—CO-Me or —C(=NH)NH$_2$, or phenylethyl, wherein the ethylene bridge is substituted by COOH, COOMe or COOEt and wherein the phenyl ring carries one of the groups —NH$_2$, —CH$_2$—NH$_2$, —NMe$_2$, —NHMe, —NEt$_2$, —NHEt, —NH—CO-Me, —CH$_2$—NH—CO-Me or —C(=NH)NH$_2$, or phenylpropyl, diphenylpropyl or pyridylmethyl;

$R^4$ denotes hydrogen or a methyl, ethyl, propyl or butyl group which may be substituted by one of the groups COOH, COOMe, COOEt or cyclohexyl, or phenyl, which may optionally be substituted by methyl, ethyl, methoxy, ethoxy, phenyloxy or CF$_3$, or benzyl, phenylethyl, phenylpropyl, diphenylpropyl, cyclohexyl, cyclooctyl or naphthyl, or a pyridine or quinoline linked via a methylene bridge, or $R^3$ and $R^4$ together with the nitrogen atom form a piperazine or diazepan ring, which may optionally be substituted by one of the groups cyclopentyl, cyclohexyl, pyridyl, benzyl or phenyl, which optionally carries a group selected from the group comprising methyl, methoxy, ethoxy, propyloxy or hydroxy, and tautomers and pharmacologically acceptable acid addition salts thereof.

Still more especially preferred are compounds of general formula (I), wherein $R^1$ denotes methyl;

$R^2$ denotes —C(=NH)NH$_2$ or —CH$_2$—NH$_2$, preferably —C(=NH)NH$_2$;

$R^3$ denotes ethyl, substituted by —NH$_2$, —NMe$_2$, —NHphenyl, —NHbenzyl, —N(benzyl)$_2$, pyrrolidine, piperidine, diazepan or —C(=NH)NH$_2$, benzyl substituted by one of the groups —CH$_2$—NH$_2$, —NMe$_2$ or —C(=NH)NH$_2$, phenylethyl, wherein the ethylene bridge is substituted by COOH, COOMe or COOEt and wherein the phenyl ring carries one of the groups —CH$_2$—NH—CO-Me or —C(=NH)NH$_2$, diphenylpropyl or pyridylmethyl;

$R^4$ denotes hydrogen or a methyl or ethyl group which may optionally be substituted by one of the groups COOH or COOEt; propyl, butyl or phenyl, which may optionally be substituted by methyl, ethyl, methoxy, ethoxy, phenyloxy or CF$_3$; benzyl, phenylethyl, phenylpropyl, diphenylpropyl, cyclohexyl, cyclooctyl, naphthyl, pyridylmethyl or quinolinylmethyl or $R^3$ and $R^4$ together with the nitrogen atom form a piperazine or diazepan ring substituted by one of the groups benzyl, cyclopentyl, cyclohexyl or phenyl, which optionally carries a group selected from the group comprising methyl, ethoxy, propyloxy or hydroxy, and tautomers and pharmacologically acceptable acid addition salts thereof.

Even more preferred are compounds of general formula (I), wherein $R^1$ denotes methyl;

$R^2$ denotes —C(=NH)NH$_2$;

$R^3$ denotes ethyl, substituted by —NH$_2$, —NHphenyl, —NHbenzyl, —N(benzyl)$_2$, pyrrolidine, piperidine, diazepan or —C(=NH)NH$_2$; benzyl substituted by —C(=NH)NH$_2$, or diphenylpropyl;

$R^4$ denotes hydrogen, methyl, propyl, butyl, benzyl or phenyl, which may optionally be substituted by ethyl or phenyloxy; phenylethyl, cyclohexyl or cyclooctyl, or $R^3$ and $R^4$ together with the nitrogen atom form a piperazine ring which is substituted by a group selected from the group comprising cyclopentyl, cyclohexyl, phenyl, methylphenyl, ethoxyphenyl or propoxyphenyl, or a diazepan ring substituted by methylphenyl, optionally in the form of their tautomers, their racemates, their enantiomers, their diastereomers and mixtures thereof and optionally the pharmacologically acceptable acid addition salts thereof.

Penultimately preferred are those compounds of general formula (I) according to the invention wherein $R^1$ denotes methyl;

$R^2$ denotes —C(=NH)NH$_2$;

$R^3$ denotes ethyl, substituted by —NH$_2$, —NHbenzyl, —N(benzyl)$_2$, pyrrolidine, piperidine, diazepan or —C(=NH)NH$_2$, benzyl substituted by —C(=NH)NH$_2$, or diphenylpropyl;

$R^4$ denotes hydrogen, methyl, butyl or phenyl, which may optionally be substituted by ethyl or phenyloxy; phenylethyl, cyclohexyl or cyclooctyl, optionally in the form of their tautomers, their racemates, their enantiomers, their diastereomers and mixtures thereof and optionally the pharmacologically acceptable acid addition salts thereof.

Ultimately preferred in accordance with the invention are the following specific compounds of the formula (I):

2-[2-(4-Amidinophenyl)-ethyl]-1-methyl-benzimidazol-5-yl-carbons äure-N-(2-amidinoethyl)-N-(2-phenylethyl)-amide;

2-[2-(4-Amidinophenyl)-ethyl]-1-methyl-benzimidazol-5-yl-carboxylic acid-N-[2-N',N'-dibenzylamino)ethyl]-N-phenyl-amide;

2-[2-(4-Amidinophenyl)-ethyl]-1-methyl-benzimidazol-5-yl-carboxylic acid-N-(2-amidinoethyl)-N-(3-phenoxy-phenyl)-amide;

2-[2-(4-Amidinophenyl)-ethyl]-1-methyl-benzimidazol-5-yl-carboxylic acid-N-(2-amidinoethyl)-N-phenyl-amide;

2-[2-(4-Amidinophenyl)-ethyl]-1-methyl-benzimidazol-5-yl-carboxylic acid-N-(2-amidinoethyl)-N-cyclooctyl-amide;

2-[2-(4-Amidinophenyl)-ethyl]-1-methyl-benzimidazol-5-yl-carboxylic acid-N-(2-amidinoethyl)-N-(3-ethyl-phenyl)-amide;

2-[2-(4-Amidinophenyl)-ethyl]-1-methyl-benzimidazol-5-yl-carboxylic acid-[N-(2-(N'-benzylamino)-ethyl)-N-cyclohexyl-amide];

2-[2-(4-Amidinophenyl)-ethyl]-1-methyl-benzimidazol-5-yl-carboxylic acid-[N-(2-amino-ethyl)-N-cyclohexyl-amide];

2-[2-(4-Amidinophenyl)-ethyl]-1-methyl-benzimidazol-5-yl-carboxylic acid-N-(3,3-diphenylpropyl)-amide;

2-[2-(4-Amidinophenyl)-ethyl]-1-methyl-benzimidazol-5-yl-carboxylic acid-N-(4-amidino-benzyl)-N-methyl-amide;

2-[2-(4-Amidinophenyl)-ethyl]-1-methyl-benzimidazol-5-yl-carboxylic acid-N-(2-amidinoethyl)-N-iso-butyl-amide;

2-{2-[4-(Amino-hydroximino-methyl)phenyl]-ethyl}-1-methyl-benzimidazol-5-yl-carboxylic acid-[N'-(cyclohexyl)-piperazide]; and, 2-[2-(4-Amidinophenyl)-ethyl]-1-methyl-benzimidazol-5-yl-carboxylic acid-[N'-(2-methyl-phenyl)-diazepide].

Apart from the abovementioned compounds of general formula (I) the present invention is also directed to compounds which are only converted into the therapeutically effective compounds of general formula (I) by the body after being taken by the patient, on the basis of a functionality which can be cleaved in vivo. Such compounds are known as prodrugs. According to another aspect the invention therefore relates to prodrugs of general formula (II)

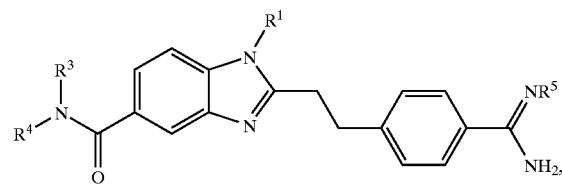

wherein $R^1$ and $R^4$ may be as hereinbefore defined and $R^3$ may have the meanings given hereinbefore or denotes $C_1$-$C_4$-alkyl, which is substituted by a group selected from the group comprising —C(=NOH)NH$_2$, —C(=NCOO—C$_1$-C$_4$-alkyl)NH$_2$ or —C(=NCOO—C$_1$-C$_4$-alkyl-phenyl)NH$_2$;

$R^5$ may denote hydroxy, —COO—C$_1$-C$_8$-alkyl or —COO—C$_1$-C$_4$-alkyl-phenyl, whilst in the abovementioned group the phenyl ring may be substituted by $C_1$-$C_4$-alkyl or $C_1$-$C_4$-alkoxy, and tautomers and pharmacologically acceptable acid addition salts thereof.

Preferred are prodrugs of general formula (II), wherein $R^1$, $R^3$ and $R^4$ may be as hereinbefore defined and $R^5$ may denote hydroxy, methoxycarbonyl, ethoxycarbonyl, propyloxycarbonyl, butyloxycarbonyl, pentyloxycarbonyl, hexyloxycarbonyl, benzyloxycarbonyl, optionally in the form of their tautomers, their racemates, their enantiomers, their diastereomers and mixtures thereof and optionally the pharmacologically acceptable acid addition salts thereof.

In another aspect the present invention relates to compounds of general formula (III)

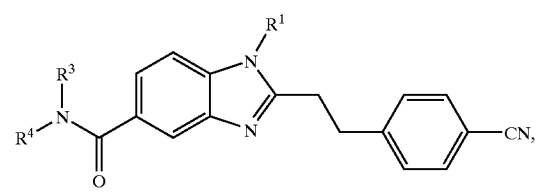

wherein the groups $R^1$, $R^3$ and $R^4$ may be as hereinbefore defined. The compounds of general formula (III) are valuable intermediate products for preparing the aminocarbonyl-substituted benzimidazole derivatives of general formula (I) according to the invention and the prodrugs of general formula (II) according to the invention.

The term alkyl groups (including those which are part of other groups) denotes branched and unbranched alkyl groups with 1 to 10 carbon atoms, preferably 1–6, most preferably 1–4 carbon atoms, such as, for example: methyl, ethyl, propyl, butyl, pentyl, hexyl, heptyl and octyl. Unless otherwise stated, the above terms propyl, butyl, pentyl, hexyl, heptyl and octyl also include all the possible isomeric forms. For example, the term propyl also includes the two isomeric groups n-propyl and iso-propyl, the term butyl includes n-butyl, iso-butyl, sec. butyl and tert.-butyl, the term pentyl includes iso-pentyl, neopentyl, etc. In some cases common abbreviations are also used to denote the abovementioned alkyl groups, such as Me for methyl, Et for ethyl etc.

Examples of cycloalkyl groups with 3–8 carbon atoms include cyclopropyl, cyclobutyl, cyclopentyl, cyclohexyl, cycloheptyl or cyclooctyl. Fluorine, chlorine, bromine or iodine is generally referred to as halogen.

Examples of N-linked cyclic groups of general formula $NR^3R^4$ include: pyrrole, pyrroline, pyrrolidine, 2-methylpyrrolidine, 3-methylpyrrolidine, piperidine, piperazine, morpholine, thiomorpholine, imidazole, imidazoline, imidazolidine, pyrazole, pyrazoline, pyrazolidine or diazepan, which may be substituted as specified in the definitions.

Examples of 5-, 6- or 7-membered, saturated or unsaturated heterocycles which may contain nitrogen, oxygen or sulphur as heteroatoms, include, unless otherwise stated in the definitions, furan, tetrahydrofuran, tetrahydrofuranon, γ-butyrolactone, α-pyran, γ-pyran, dioxolan, tetrahydropyran, dioxane, thiophene, dihydrothiophene, thiolan, dithiolan, pyrrole, pyrroline, pyrrolidine, pyrazole, pyrazoline, pyrazolidine, imidazole, imidazoline, imidazolidine, triazole, tetrazole, pyridine, piperidine, pyridazine, pyrimidine, pyrazine, piperazine, triazine, tetrazine, morpholine, thiomorpholine, diazepan, oxazole, isoxazole, oxazine, thiazole, isothiazole, thiadiazole, oxadiazole and pyrazolidine, wherein the heterocyclic group may be substituted as stated in the definitions.

"=O" denotes an oxygen atom linked via a double bond.

Aminocarbonyl-substituted benzimidazole derivatives of formula (I) and the prodrugs of general formula (II) may be synthesised using the methods of synthesis known from the prior art. In this respect, attention is drawn to International Patent Application WO 98/37075 mentioned earlier, the contents of which are hereby referred to.

One possible method of obtaining the compounds according to the invention with the aid of and using conventional chemical methods of synthesis is diagrammatically shown hereinafter (Diagram 1).

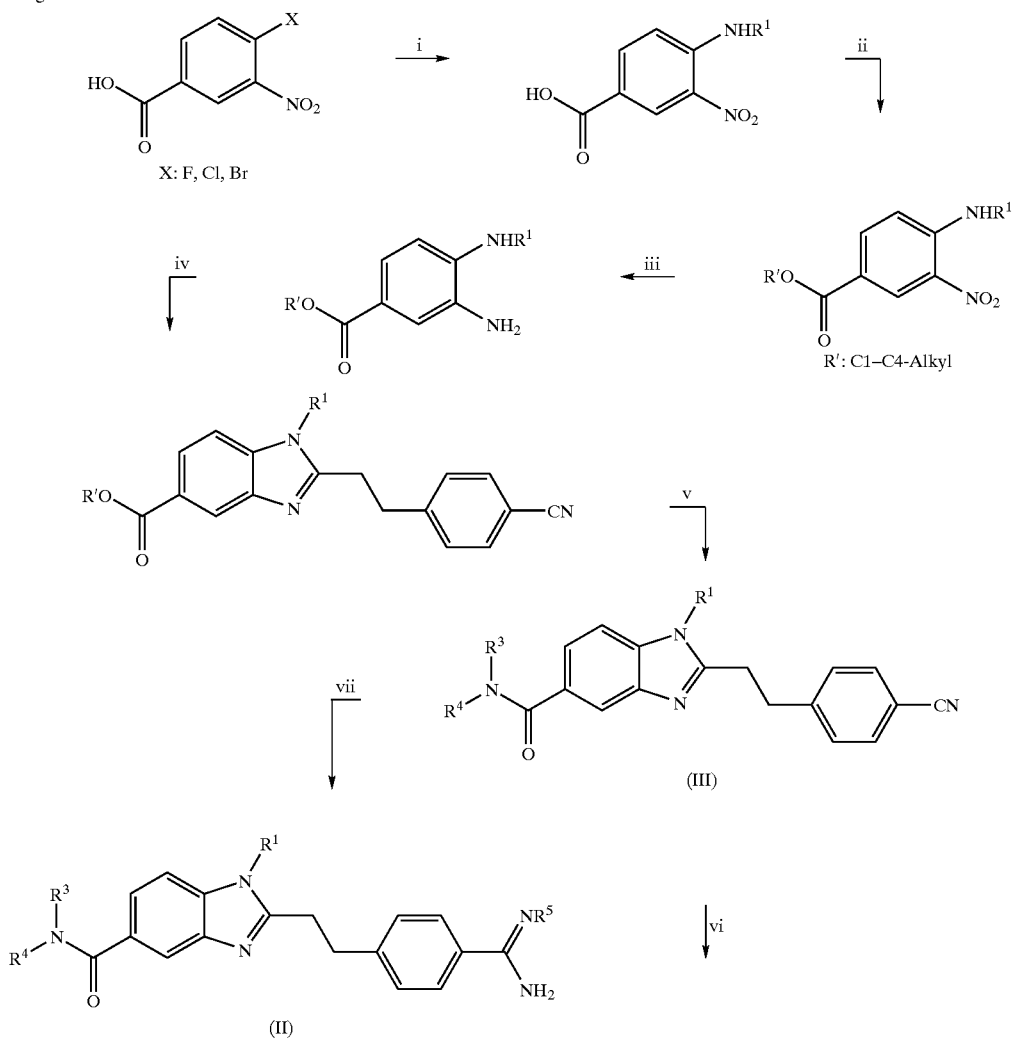

Diagram 1:

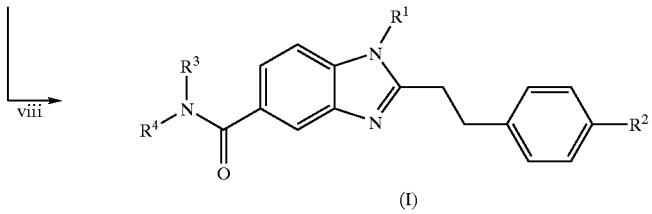

(I)

In a first step (step i, Diagram 1) 4-amino-3-nitrobenzoic acid derivatives are synthesised, starting from 4-halo-3-nitro-benzoic acid derivatives, by aminolysis with suitably substituted primary amines. The reaction is carried out in suitable organic solvents such as dimethyl sulphoxide, N,N-dimethylformamide, N-methylpyrrolidone or optionally in water at ambient temperature or in a temperature range from 30–80° C., preferably 40–50° C. The aminobenzoic acid compounds thus obtained are converted by standard conventional methods into the corresponding alkylesters, preferably into the corresponding methylesters or ethylesters (step ii, Diagram 1). The reduction of the nitro group to the alkyl diaminobenzoates is preferably carried out by catalytic hydrogenation according to step iii (Diagram 1). The preferred catalyst is palladium. Palladium on charcoal (5%) is particularly preferred as the catalyst. By reacting the diaminobenzoates thus obtained with p-cyanophenylpropionic acid in the presence of dehydrating reagents, the benzimidazole heterocycle is formed according to step v (Diagram 1). The reaction is optionally carried out in a solvent or mixture of solvents such as methylene chloride, dimethylformamide, benzene, toluene, chlorobenzene, tetrahydrofuran, benzene/tetrahydrofuran or dioxane. Suitable dehydrating agents include, for example, isobutyl chloroformate, tetraethyl orthocarbonate, trimethyl orthoacetate, 2,2-dimethoxypropane, tetramethoxysilane, phosphorus oxychloride, thionylchloride, trimethylchlorosilane, phosphorus trichloride, phosphorus pentoxide, ethyl 1,2-dihydro-2-ethoxy-quinoline-1-carboxylate (EEDQ), i-propylester 1,2-dihydro-2-i-propyloxy-quinolin-1-carboxylate (IIDQ), N,N'-dicyclohexylcarbodiimide, N,N'-dicyclohexylcarbodiimide/N-hydroxysuccinimide, N,N'-dicyclohexylcarbodiimide/1-hydroxy-benztriazole, 2-(1H-benzotriazol-1-yl)-1,1,3,3-tetramethyluronium-tetrafluoroborate, 2-(1 H-benzotriazol-1-yl)-1,1,3,3-tetramethyluronium-tetrafluoroborate/1-hydroxy-benzotriazole, N,N'-carbonyldiimidazole or triphenylphosphine/carbon tetrachloride. In some cases it may prove useful to add a base such as pyridine, 4-dimethylaminopyridine, N-methyl-morpholine or triethylamine. The reaction is normally carried out at temperatures between 0 and 150° C., preferably at temperatures between 0 and 110° C.

The benzimidazole derivatives of general formula (III) which may be prepared according to step v (Diagram 1) are either obtainable directly from the abovementioned benzimidazole carboxylates or are obtained via the corresponding carboxylic acids or carboxylic acid halides.

If the carboxylic acid esters obtained in step iv (Diagram 1) are saponified under standard conditions (protic organic solvent such as methanol, ethanol or isopropanol, for example. optionally in the presence of water and in the presence of bases such as hydroxides or carbonates of alkali and alkaline earth metals), this leads to the corresponding free carboxylic acids. Usually, this saponification is carried out at temperatures between 0–40° C., preferably at 10–30° C. If desired, however, the synthesis may also be carried out at elevated temperature (>50° C. to reflux temperature).

The preferred solvent according to the invention is a methanol-water mixture. The base used is preferably sodium hydroxide. The reaction of the resulting acid with the amines H—NR³R⁴ to obtain the compounds of general formula (III) is optionally carried out in a solvent or mixture of solvents such as methylene chloride, dimethylformamide, benzene, toluene, chlorobenzene, tetrahydrofuran, benzene/tetrahydrofuran or dioxane or in the corresponding amine H—NR³R⁴, optionally in the presence of a dehydrating agent, e.g. in the presence of isobutyl chloroformate, tetraethyl orthocarbonate, trimethyl orthoacetate, 2,2-dimethoxypropane, tetramethoxysilane, thionylchloride, trimethylchlorosilane, phosphorus trichloride, phosphorus pentoxide, N,N'-dicyclohexylcarbodiimide, N,N'-dicyclohexylcarbodiimide/N-hydroxysuccinimide, N,N'-dicyclohexylcarbodiimide/1-hydroxy-benzotriazole, 2-(1H-benzotriazol-1-yl)-1,1,3,3-tetramethyluronium-tetrafluoroborate, 2-(1H-benzotriazol-1-yl)-1,1,3,3-tetramethyluronium-tetrafluoroborate/1-hydroxy-benzotriazole, N,N'-carbonyldiimidazole or triphenylphosphine/carbon tetrachloride, and optionally with the addition of a base such as pyridine, 4-dimethylaminopyridine, N-methyl-morpholine or triethylamine, appropriately at temperatures of between 0 and 150° C., preferably at temperatures of between 0 and 100° C., The synthesis of the compounds of general formula (III) starting from the carboxylates obtained in Diagram 1 (step iv) or from the corresponding carboxylic acid chlorides is carried out either in the corresponding amine H—NR³R⁴ as solvent, or with the amine H—NR³R⁴ in the presence of a solvent such as methylene chloride, ether or ethyl acetate and preferably in the presence of a tertiary organic base such as triethylamine, N-ethyl-diisopropylamine or N-methyl-morpholine at temperatures of between 0 and 150° C., preferably at temperatures of between 40 and 100° C.

A compound of general formula (I) is obtained for example by treating a compound of general formula (III, Diagram 1, step vi) with a corresponding alcohol such as methanol, ethanol, n-propanol, isopropanol or benzylalcohol optionally mixed with another organic solvent such as for example chloroform, nitrobenzene or toluene in the presence of an acid such as hydrochloric acid or by reacting a corresponding amide with a trialkyloxonium-salt such as triethyloxonium tetrafluoroborate in a solvent such as methylene chloride, tetrahydrofuran or dioxane at temperatures of between −10 and 50° C., but preferably at 0–20° C. Alternatively, the compounds of general formula (I) may be obtained by reacting a compound of general formula (III) (Diagram 1, step vi) with sulphur nucleophiles such as e.g. hydrogen sulphide, ammonium or sodium sulphide, sodium hydrogen sulphide, carbon disulphide, thioacetamide or bistrimethylsilylthioether optionally in the presence of bases such as triethylamine, ammonia, sodium hydride or sodium alkoxide in solvents such as methanol, ethanol, water, tetrahydrofuran, pyridine, dimethylformamide or 1,3-dimethyl-imidazolidin-2-one at 20–100° C., and subsequently treating with a suitable methylating agent such as e.g. methyl iodide or dimethyl sulphate in a solvent such as acetonitrile or acetone at temperatures of between −10 and 50° C., but preferably at 0–20° C. and then treating with ammonia, ammonium carbonate or ammonium chloride in a suitable alcohol, such as for example methanol, ethanol, isopropanol etc. at temperatures between −10 and 50° C., but preferably at 0–20° C.

Moreover, the compounds of general formula (I) according to the invention may be obtained by treating a compound of general formula (III) with lithium hexamethyldisilazide in a suitable organic solvent such as e.g. tetrahydrofuran at temperatures of between −20 and 50° C., but preferably at 0–20° C. and then hydrolysing with dilute hydrochloric acid at 0–5° C.

Another alternative method of obtaining compounds of general formula (I) is by treating a compound of general formula (III) with ammonium chloride and trimethylaluminium in a suitable organic solvent such as e.g. toluene at temperatures of between 20 and 150° C., but preferably at 110° C.

A compound of general formula (II) is obtained for example by treating a compound of general formula (III, Diagram 1, step vii) with hydroxylamine in the presence of carbonates or alkoxides of the alkali or alkaline earth metals in solvents such as methanol, ethanol, n-propanol or isopropanol optionally mixed with dioxane or tetrahydrofuran. The alkoxides may be prepared from the respective alkali metals or metal hydrides and the corresponding alcohol. The reaction is preferably carried out at 20–100° C., most preferably at the boiling temperature of the solvent used.

Compounds of general formula (II) may alternatively be prepared by treating a compound of general formula (III, Diagram 1, step vii) with a corresponding alcohol such as methanol, ethanol, n-propanol, isopropanol or benzylalcohol in the presence of an acid such as hydrochloric acid or by reacting a corresponding amide with a trialkyloxonium-salt such as triethyloxonium-tetrafluoroborate in a solvent such as methylene chloride, tetrahydrofuran or dioxane at temperatures of between −10 and 50° C., but preferably at 0–20° C. and subsequently treating with hydroxylamine in the presence of bases in a suitable alcohol, such as methanol, ethanol, isopropanol etc. at temperatures of between −10 and 50° C., but preferably at 0–20° C.

A compound of general formula (I) may be obtained for example by treating a compound of general formula (II, Diagram 1, step viii) with hydrogen in the presence of hydrogenation catalysts such as Raney nickel or rhodium/aluminium oxide in water or methanol, optionally with the addition of acids such as hydrochloric acid or methanesulphonic acid or by treating with hydrogen in the presence of palladium/charcoal in acetic acid/acetic anhydride at 20–50° C. and 1–5 bar hydrogen pressure, preferably at ambient temperature and normal pressure.

Acyl- or alkoxycarbonyl prodrugs of the compound of general formula (I) are obtained by reacting the compounds of general formula (I) with the corresponding acid chlorides in the presence of bases such as e.g. triethylamine, N-methylmorpholine, diethylisopropylamine or DBU in a suitable solvent such as methylene chloride, chloroform, tetrahydrofuran, acetonitrile, dimethylformamide or dimethyl sulphoxide.

Alternatively to the method described above the compounds according to the invention may also be obtained on a polymeric carrier by means of a solid phase synthesis. The method of production by solid phase synthesis, as shown by way of example in Diagram 2 in a manner which must not be regarded as restricting the core of the invention, is of particular interest for those compounds according to the invention wherein the group $R^3$ is terminally amino-substituted.

Diagram 2:

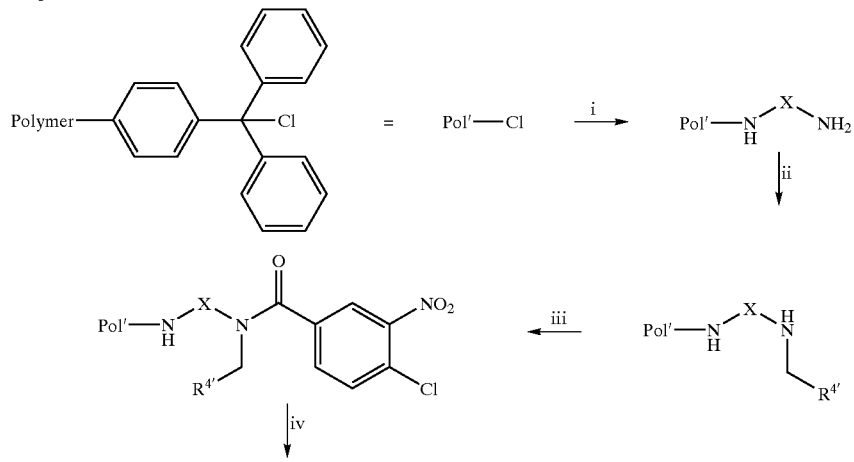

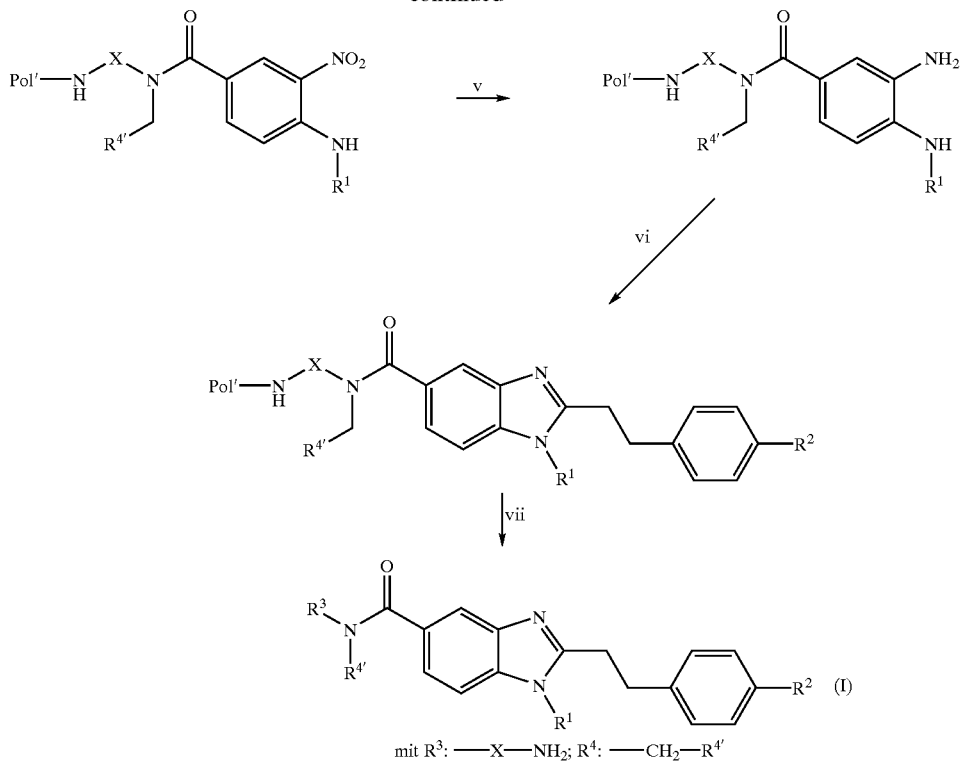

mit R³: —X—NH₂; R⁴: —CH₂—R⁴'

In a first step (Diagram 2, step i) a resin-bound diamine is reacted. The resins which may be used are usually trityl, 2-chlorotrityl, 4-methoxytrityl resins with polymer matrices of crosslinked polystyrene or Tentagel or Synphase™ crowns. In order to carry out the synthesis step according to Diagram 2 (step i) the same procedure is used as hereinbefore, according to the invention. 2–4 equivalents of the diamine, based on the resin charge, are dissolved in an organic solvent selected from the group comprising dichloromethane, tetrahydrofuran, 1,2-dichloroethane or dimethylformamide. The solution is added to the trityl resin and stirred for 2–16 h at ambient temperature. Then the resin is filtered off and washed several times with dry pyridine or a mixture of dichloromethane/diisopropylamine and dichloromethane or dry diethylether. The resin is dried in vacuo until a constant weight is obtained.

In a second step (Diagram 2, step ii) the diamine coupled to the resin is reacted in a reductive amination with the aldehydes R⁴—CHO, wherein R⁴ may have the meanings given hereinbefore. The following procedure is used for this. 2–10 Equivalents of the aldehyde R⁴—CHO, dissolved in tetramethyl orthoformate/dichloromethane or dichloromethane or dichloromethane/dimethylformamide or dimethylformamide or 1,2-dichloromethane, are added to diamine-charged resin, suspended in tetramethyl orthoformate or dichloromethane, dimethylformamide, 1,2-dichloromethane, 1-methyl-2-pyrrolidone (each with added tetramethyl orthoformate) and shaken for 2–12 h at 0–30° C. Then the resin is washed and mixed with a solution of sodium triacetoxyborohydride or sodium cyanoborohydride in dichloromethane or DMF or 1,2-dichloromethane at 0–30° C. and agitated for 2–24 h. Alternatively the aldehyde and the reducing agent may be added directly to the resin.

In the third step the amine coupled to the resin is reacted with 4-chloro-3-nitrobenzoylchloride in an acylating reaction (Diagram 2, step iii). The following procedure is used for this. The resin is suspended in dichloromethane or dimethylformamide or 1,2-dichloromethane or 1-methyl-2-pyrrolidone or tetrahydrofuran with the addition of a base such as triethylamine or diisopropylethylamine or pyridine and combined at ambient temperature with a solution of 4-chloro-3-nitro-benzoylchlorid in dichloromethane or 1,2-dichloroethane or 1-methyl-2-pyrrolidone or dimethylformamide or tetrahydrofuran and shaken for 1–12 h at ambient temperature. Then the mixture is filtered and washed with various solvents. Alternatively to the method shown by way of example in Diagram 2, it is possible to use 4-fluoro-3-nitro-benzoylchloride, for example, instead of the 4-chloro-3-nitro-benzoylchloride.

There is then a Nucleophilic Substitution at the benzoic acid amide coupled to the resin by the primary amines R¹—NH₂.(Diagram 2, step iv). The following procedure is used for this, according to the invention. The resin, suspended in diisopropylethylamine solution or in 1-methyl-2-pyrrolidone or dimethylformamide (20% v/v), is combined with a solution of an amine R¹—NH₂ in 1-methyl-2-pyrrolidone or dimethylformamide and heated for 2–24 h in a temperature range from 50–110° C. After cooling to ambient temperature the resin is filtered off and washed with various solvents.

The reduction of the nitro group leads according to step v (Diagram 2) to the diaminobenzoic acid amides coupled to the resin. The following procedure is used for this, according to the invention. The resin is suspended in dimethylformamide or 1-methyl-2-pyrrolidone, combined with 5–50 equivalents of 1.0 M SnCl₂ solution in dimethylformamide or in 1-methyl-2-pyrrolidone and shaken for 12–48 h at ambient temperature. Then the resin is filtered off and washed intensively with various solvents. Alternatively to the reduction with the abovementioned SnCl₂ solutions, the reaction may also be carried out for example with sodium borohydride/Cu(acac)$_2$ (cat.) or Na$_2$S$_2$O$_4$ in protic organic solvents such as alcohols, preferably in ethanol.

By reacting with the aldehydes R$^2$—C$_6$H$_4$—CH$_2$CH$_2$—CHO according to step vi (Diagram 2) the resin-coupled benzimidazole heterocycles are obtained by oxidative cyclisation. The following procedure is used for this, according to the invention. The resin is suspended in tetrahydrofuran or dioxane or 1-methyl-2-pyrrolidone, combined with a solution of an aldehyde R$^2$—C$_6$H$_4$—CH$_2$CH$_2$—CHO in THF or dioxane or 1-methyl-2-pyrrolidone and shaken for 12–48 h at ambient temperature in oxygen from the air. Then the resin is filtered off and washed.

After the cleaving of the resin, the compounds of general formula (I) according to the invention can thus be obtained (Diagram 2, step vii). The following procedure is used according to the invention for the cleaving. The resin is shaken with trifluoroacetic acid (10–70% v/v) in dichloromethane for 1 h at ambient temperature and suction filtered. Then the resin remaining is once again combined with trifluoroacetic acid (10–70% v/v) in dichloromethane, suction filtered, and the combined filtrates are evaporated down in vacuo. After the resin residue has been treated with a mixture of dichloromethane/methanol it is filtered off after 1 h shaking at ambient temperature.

The filtrates and the residues obtained are combined and evaporated to dryness in vacuo.

Procedures by way of example for preparing the compounds according to the invention will be described in more detail hereinafter. The Examples which follow serve solely as a detailed illustration without restricting the subject matter of the invention.

EXAMPLE 1

2-[2-(4-Amidinophenyl)ethyl]-1-methyl-benzimidazol-5-yl-carboxylic Acid-N-(pyridin-3-yl-methyl)-N-methyl-amide-hydrochloride

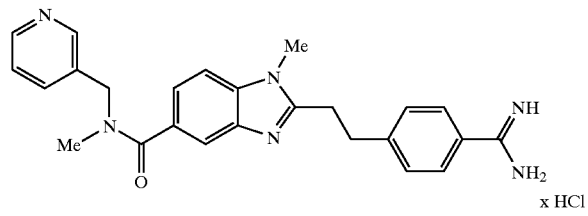

x HCl a) 4-Methylamino-3-nitrobenzoic Acid:

20 g (100 mmol) of 4-chloro-3-nitro-benzoic acid are taken up in 80 mL 40% aqueous methylamine solution, stirred for 15 h at ambient temperature and 1.5 h at 40–50° C.

After cooling the mixture is acidified with acetic acid. The crystals formed are filtered off, washed with cold water and dried. Yield: 18.2 g (93%); melting point: >220° C.

b) Methyl 4-Methylamino-3-nitro-benzoate:

9.8 g (50 mmol) of 4-methylamino-3-nitro-benzoic acid are combined with K$_2$CO$_3$ (14 g) in 50 mL DMF. To this suspension 5 mL of dimethyl sulphate are added dropwise within 10 min. with stirring. The temperature rises to about 35° C. The mixture is stirred for 15 minutes and then heated to 60° C. for 0.5 h. After cooling the mixture is diluted with water, the solid precipitated is filtered off, washed with water and dried. Yield: 9.8 g (93%); melting point: 138–140° C.;

c) Methyl 3-Amino-4-methylamino-benzoate:

71 g of methyl 4-methylamino-3-nitro-benzoate (338 mmol) are hydrogenated in 1.4 L of methanol and 67 mL of concentrated aqueous hydrochloric acid in the presence of 15 g Pd/C (5%) at 2–5 bar at ambient temperature. After the catalyst has been filtered off and the solvent distilled off in vacuo the residue is taken up in 200 mL water, covered with ethyl acetate and made alkaline with 50% aqueous potassium carbonate solution. The produce is extracted into the organic phase which is washed with water again and finally dried over sodium sulphate. After the majority of the solvent has been distilled off in vacuo the residue is combined with diethylether and cooled. The crystals formed are filtered off.

Yield: 54 g (81%); melting point: 215–220° C. (decomposition);

d) Methyl 2-[2-(4-Cyanophenyl)-ethyl]-1-methyl-benzimidazol-5-yl-carboxylate:

7.5 g (42 mmol) of methyl 3-amino-4-methylamino-benzoate and 7.3 g (42 mmol) of p-cyano-phenylpropionic acid are taken up in 50 mL of phosphorus oxychloride and refluxed for 2 h. After cooling the excess phosphorus oxychloride is decomposed with ice water. Ethyl acetate is poured over and the mixture is made alkaline with potassium carbonate with stirring. The organic phase is separated off, washed with water and dried. After most of the solvent has been distilled off in vacuo the mixture is cooled. The crystals precipitated are filtered off and washed with cold ethyl acetate or diethylether. Yield: 8.5 g (63%); melting point: 148–150° C.; mass: calc.: [319], found: [M+H]$^+$ 320, [M+Na]$^+$ 342, [2M+H]$^+$ 639; $^1$H-NMR (250 MHz, DMSO-d6): δ [ppm]=8.18 (7H, m, aryl-H); 3.86 (3H, s, OCH$_3$); 3.75 (3H, s, aryl-N—CH$_3$); 3.26 (4H, s, aryl-CH$_2$—CH$_2$—).

e) 2-[2-(4-Cyanophenyl)-ethyl]-1-methyl-benzimidazol-5-yl-carboxylic Acid:

5.0 g (15.7 mmol) of methyl 2-[2-(4-cyanophenyl)-ethyl]-1-methyl-benzimidazol-5-yl-carboxylate are taken up in 50 mL methanol, combined with 20 mL of aqueous sodium hydroxide solution (1N) and refluxed for 0.5 h. The mixture is combined with 20 mL of aqueous hydrochloric acid (1N) and diluted with water. The crystals precipitated are filtered off, washed with water, acetone and ether. The crude product obtained is recrystallised from dimethylformamide.

Yield: 4.5 g (94%); melting point: >220° C.;

f) 2-[2-(4-Cyanophenyl)-ethyl]-1-methyl-benzimidazol-5-yl-carboxylic Acid-N-(pyridin-3-yl-methyl)-N-methyl-amide:

1.2 g of 2-[2-(4-cyanophenyl)-ethyl]-1-methyl-benzimidazol-5-yl-carboxylic acid (4 mmol), 3-(methylaminomethyl)-pyridine (0.49 g, 4 mmol) and 0,7 mL of N-methylmorpholine are taken up in 20 mL dimethylformamide. Then 1.6 g of O-(benzotriazol-1-yl)-N,N,N', N'-tetramethyluronium tetrafluoroborate (=TBTU; 5 mmol) are added and stirred for 16 h at RT. After dilution with 75 mL of ethyl acetate the mixture is washed with saturated, aqueous sodium hydrogen carbonate solution and washed with water and dried over sodium sulphate. After most of the solvent has been distilled off the precipitate formed is filtered off and washed with ether. Yield: 1.2 g (73%); melting point: 150–153° C.;

g) 2-[2-(4-Amidinophenyl)-ethyl]-1-methyl-benzimidazol-5-yl-carboxylic Acid-N-(pyridin-3-yl-methyl)-N-methyl-amide-hydrochloride:

1.1 g (2.7 mmol) of 2-[2-(4-Cyanophenyl)-ethyl]- -methyl-benzimidazol-5-yl-carboxylic acid-[N-(pyridin-3-yl-methyl)-N-methyl-amide are taken up in 25 mL of a cooled ethanolic HCl solution saturated at 0° C. It is stirred until the educt has dissolved completely and the temperature is maintained at 0–5° C. for about 12 h. The ethanol is distilled off at a maximum of 40° C. and the residue is taken up in 30 mL of an ethanolic ammonia solution saturated at 0° C. It is stirred for 1 h at ambient temperature and 2 h at 40–50° C., combined with a further 10 mL of the abovementioned ammonia solution, refluxed for 1 h and left to stand for 12 h at ambient temperature. The inorganic salts precipitated are filtered off, the filtrate is evaporated down to half and diluted with 50 mL of acetone. The crystals precipitated are filtered off and washed with acetone.

Yield: 1.0 g (80%); melting point: >220° C. mass: calc.: [426], found: [M+H]$^+$ 427, [M+2H]$^{2+}$ 214; $^1$H-NMR (250 MHz, DMSO-d6): δ [ppm]=8.64–7.26 (11H, m, aryl-/pyridyl-H); 4.79 (2H, s, N—CH$_2$—); 3.72 (3H, s, aryl—N—CH$_3$); 3.30 (4H, s, aryl-CH$_2$—CH$_2$—); 3.02 (3H, s, CO—N—CH$_3$).

EXAMPLE 2

2-[2-(4-Amidinophenyl)ethyl]-1-methyl-benzimidazol-5-yl-carboxylic Acid-N-[2-(N,N-dibenzylamino)ethyl]-N-cyclohexyl-amide-dihydrochloride

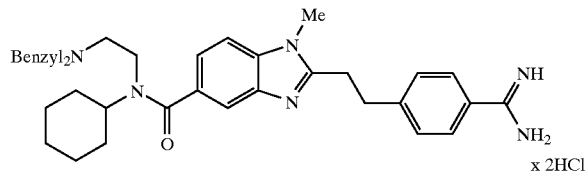

a) 2-[2-(4-Cyanophenyl)-ethyl]-1-methyl-benzimidazol-5-yl-carboxylic Acid Chloride:

7.0 g (23 mmol) of 2-[2-(4-Cyanophenyl)-ethyl]-1-methyl-benzimidazol-5-yl-carboxylic acid (obtainable according to Example 1, step e), 2 drops of dimethylformamide and 70 mL of thionylchloride are refluxed for 3 h. The excess thionylchloride is distilled off and the solid residue remaining is taken up in acetonitrile/diethylether and filtered. The solid filtered off is washed with diethylether.

Yield: 7.8 g (94%);

b) 2-[2-(4-Cyanophenyl)-ethyl]-1-methyl-benzimidazol-5-yl-carboxylic Acid-N-[2-(N',N'-dibenzylamino)-ethyl]-N-cyclohexyl-amide:

4.0 g (11 mmol) of 2-[2-(4-Cyanophenyl)-ethyl]-1-methyl-benzimidazol-5-yl-carboxylic acid chloride are added in batches to 3.2 g (10 mmol) of N',N'-dibenzyl-N-cyclohexyl-ethylenediamine and 3 mL N-methylmorpholine in 75 mL of ethyl acetate with stirring at RT. The mixture is stirred for 0.5 h at 40–50° C., cooled, poured onto water and extracted with ethyl acetate. The organic phase is washed with dilute aqueous sodium hydroxide solution and with water, dried over sodium sulphate and most of the solvent is distilled off in vacuo. The residue is diluted with diethylether and cooled. The crystals precipitated are filtered off and washed with diethylether.

Yield: 5.7 g (94%); melting point: 124–126° C.;

c) 2-[2-(4-Amidinophenyl)-ethyl]-1-methyl-benzimidazol-5-yl-carboxylic acid-N-[2-(N',N'-dibenzylamino)-ethyl]-N-cyclohexyl-amide-dihydrochloride:

The reaction was carried out starting from 9.4 mmol of 2-[2-(4-cyanophenyl)-ethyl]-1-methyl-benzimidazol-5-yl-carboxylic acid-N-[2-(N',N'-dibenzylamino)-ethyl]-N-cyclohexyl-amide analogously to Example 1, step g. The product is obtained by crystallisation from acetone with some water. Yield: 67%; melting point: 140–148° C. (dihydrochloride, contains water of crystallisation); mass: calc.: [626], found: [M+H]$^+$ 627, [M+2H]$^{2+}$ 314; $^1$H-NMR (250 MHz, DMSO-d6): δ [ppm]=9.35, 9.10 (4H, 2s, C(=NH$_2^+$)NH$_2$); 7.86–7.01 (17H, m, aryl-H); 3.66, 2.60 (4H, 2 m, N—CH$_2$—CH$_2$—N); 3.75 (3H, s, aryl-N—CH$_3$); 3.62 (1H, m, N-cyclohexyl-H); 3.26 (4H, s, aryl-CH$_2$—CH$_2$—); 1.71–054 (10H, m, cyclohexyl).

EXAMPLE 3

2-[2-(4-Amidinophenyl)-ethyl]1-methyl-benzimidazol-5-yl-carboxylic Acid-N-[2-(N,N-dimethylamino)-ethyl]-N-methyl-amide-dihydrochlonide

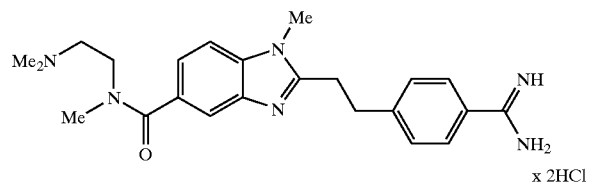

a) 2-[2-(4-Cyanophenyl)-ethyl]-1-methyl-benzimidazol-5-yl-carboxylic Acid-N-[2-(N,N-dimethylamino)-ethyl]-N-methyl-amide:

The synthesis is carried out analogously to step f (Example 1) by reacting 5 mmol of 2-[2-(4-cyanophenyl)-ethyl]-1-methyl-benzimidazol-5-yl-carboxylic acid with N,N,N'-trimethylethylenediamine. The product is crystallised from ethyl acetate/diethyl ether.

Yield: 62%; melting point: 130–132° C.;

b) 2-[2-(4-Amidinophenyl)-ethyl]-1-methyl-benzimidazol-5-yl-carboxylic Acid-N-[2-(N,N-dimethylamino)-ethyl]-N-methyl-amide-dihydrochloride:

The reaction was carried out starting from 6 mmol of 2-[2-(4-cyanophenyl)-ethyl]-1-methyl-benzimidazol-5-yl-carboxylic acid-N-[2-(N,N-dimethylamino)-ethyl]-N-methyl-amide analogously to Example 1, step g. The product is obtained by crystallisation from acetone and is washed with cold ethanol/diethylether.

Yield: 71%; melting point: >220° C. (dihydrochloride); mass: calc.: [406], found: [M+H]$^+$ 407, [2M+H]$^+$ 814; $^1$H-NMR (250 MHz, DMSO-d6): δ [ppm]=10.70 (1H, s, H+); 9.38, 9.21 (4H, 2 s, —C(=NH$_2^+$)NH$_2$); 7.89–7.25 (7H, m, aryl-H); 3.80, 3.33 (4H, 2 m, N—CH$_2$—CH$_2$—) (3H, s, aryl-N—CH3); 3.26 (4H, m, aryl-CH$_2$—CH$_2$—); 2.99 (3H, s, CO—N—CH$_3$); 2.80 (6H, s, N—(CH$_3$)$_2$).

EXAMPLE 4

2-[2-(4-Amidinophenyl)-ethyl]-1-methyl-benzimidazol-5-yl-carboxylic Acid-N-(4-amidino-benzyl)-N-methyl-amide-trihydrochloride

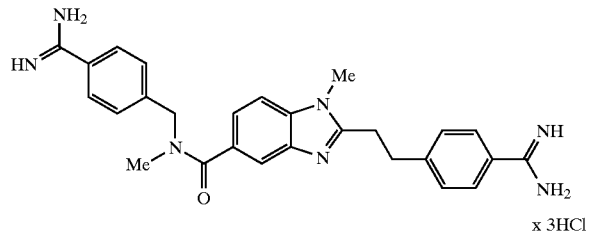

a) 2-[2-(4-Cyanophenyl)-ethyl]-1-methyl-benzimidazol-5-yl-carboxylic Acid-N-(4-cyanobenzyl)-N-methyl-amide:

The synthesis is carried out analogously to step f (Example 1) by reacting 10 mmol of 2-[2-(4-cyanophenyl)-ethyl]-1-methyl-benzimidazol-5-yl-carboxylic acid with N-(4-cyanobenzyl)-N-methylamine. Yield: 81%; melting point: 138–140° C.;

b) 2-[2-(4-Amidinophenyl)-ethyl]-1-methyl-benzimidazol-5-yl-carboxylic Acid-N-(4-amidino-benzyl)-N-methyl-amide-trihydrochloride:

The reaction was carried out starting from 7 mmol of 2-[2-(4-cyanophenyl)-ethyl]-1-methyl-benzimidazol-5-yl-carboxylic acid-N-(4-cyanobenzyl)-N-methyl-amide analogously to Example 1, step g. The product is obtained by crystallisation from acetone and is washed with cold ethanol/diethylether.

Yield: 68%; melting point: >220° C. (trihydrochloride); mass: calc.: [467], found: [M+H]$^+$ 468; $^1$H-NMR (250 MHz, DMSO-d6): δ [ppm]=10.2 (1H, broad, H$^+$); 9.52, 9.47, 9.36, 9.31 (8H, 4 s, 2—C(=NH$_2$$^+$)NH$_2$); 8.00–7.20 (11H, m, aryl-H); 4.77 (2H, s, N—CH$_2$—); 3.78 (3H, s, aryl-N—CH$_3$); 3.26 (4H, s, aryl-CH$_2$—CH$_2$—); 2.95 (3H, s, CO—N—CH$_3$).

EXAMPLE 5

2-[2-(4-Amidinophenyl)-ethyl]-1-methyl-benzimidazol-5-yl-carboxylic Acid-N-(4-amidino-benzyl)-N-ethoxycarbonylmethyl-amide-dihydrochloride

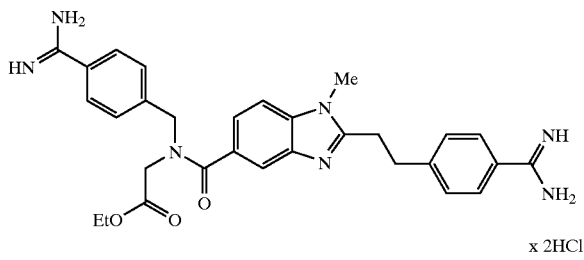

a) 2-[2-(4-Cyanophenyl)-ethyl]-1-methyl-benzimidazol-5-yl-carboxylic Acid-N-(4-cyanobenzyl)-N-ethoxycarbonylmethyl-amide:

The synthesis is carried out analogously to step f (Example 1) by reacting 9 mmol of 2-[2-(4-cyanophenyl)-ethyl]-1-methyl-benzimidazol-5-yl-carboxylic acid with N-(4-cyanobenzyl)-N-ethoxycarbonylmethyl-amine. The crude product is purified by chromatography on silica gel (dichloromethane:ethanol=25:1). Yield: 62%; yellow oil;

b) 2-[2-(4-Amidinophenyl)-ethyl]-1-methyl-benzimidazol-5-yl-carboxylic Acid-N-(4-amidino-benzyl)-N-ethoxycarbonylmethyl-amide-dihydrochloride:

The reaction was carried out starting from 4.5 mmol of 2-[2-(4-cyanophenyl)-ethyl]-1-methyl-benzimidazol-5-yl-carboxylic acid-N-(4-cyanobenzyl)-N-ethoxycarbonylmethyl-amide analogously to Example 1, step g. The product is obtained by chromatography on silica gel (dichloromethane:ethanol=4:1).

Yield: 89%; solid foam; mass: calc.: [539], found: [M+H]$^+$ 540; $^1$H-NMR (250 MHz, DMSO-d6): δ [ppm]= 9.63, 9.54, 9.44, 9.38 (8H, s, 2 C(=NH$_2$$^+$)NH$_2$); 8.13–7.30 (11H, m, aryl-H); 4.83 (2H, s, N—CH$_2$-aryl); 4.19 (2H, s N—CH$_2$—C=O); 3.81 (3H, s, aryl-N—H$_3$); 3.89 (2H, q, J=7.2 Hz, —O—CH$_2$—); 3.30 (4H, s, aryl-CH$_2$—CH$_2$—); 1.07 (3H, t, J=7.2 Hz, —O—CH$_2$–CH$_3$).

EXAMPLE 6

2-[2-(4-Amidinophenyl)-ethyl]-1-methyl-benzimidazol-5-yl-carboxylic Acid-N-(4-dimethylaminobenzyl)-N-methyl-amide-hydrochloride

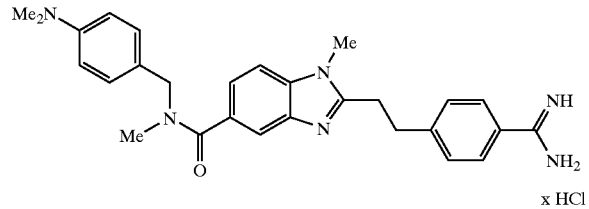

a) 2-[2-(4-Cyanophenyl)-ethyl]-1-methyl-benzimidazol-5-yl-carboxylic Acid-N-(4-dimethylaminobenzyl)-N-methyl-amide:

The synthesis is carried out analogously to step f (Example 1) by reacting 2.3 mmol of 2-[2-(4-cyanophenyl)-ethyl]-1-methyl-benzimidazol-5-yl-carboxylic acid with N-(4-dimethylaminobenzyl)-N-methyl-amine. The crude product is purified by chromatography on silica gel (dichloromethane:ethanol=98:2). Yield: 77%;

b) 2-[2-(4-Amidinophenyl)-ethyl]-1-methyl-benzimidazol-5-yl-carboxylic Acid-N-(4-dimethylaminobenzyl)-N-methyl-amide-hydrochloride:

The reaction was carried out starting from 2-[2-(4-cyanophenyl)-ethyl]-1-methyl-benzimidazol-5-yl-carboxylic acid-N-(4-dimethylaminobenzyl)-N-methyl-amide analogously to Example 1, step g. The product is obtained by chromatography on silica gel (dichloromethane:methanol=9:1). Yield: 62%; solid foam; mass: calc.: [468], found: [M+H]$^+$ 469; $^1$H-NMR (250 MHz, DMSO-d6): δ [ppm]=9.33, 9.12 (4H, 2 s, C(=NH$_2$$^+$)NH$_2$); 7.89–6.66 (11H, m, aryl-H); 4.49 (2H, s, N—CH$_2$—); 3.75 (3H, s, aryl-N—CH$_3$); 3.27 (4H, s, aryl-CH$_2$—CH$_2$—); 2.88 (6H, s, N—(CH$_3$)$_2$); 2.85 (3H, s, CO—N—CH$_3$);.

EXAMPLE 7

2-[2-(4-Amidinophenyl)-ethyl]-1-methyl-benzimidazol-5-yl-carboxylic Acid-N-(2-amidinoethyl)-N-methyl-amide-dihydrochloride

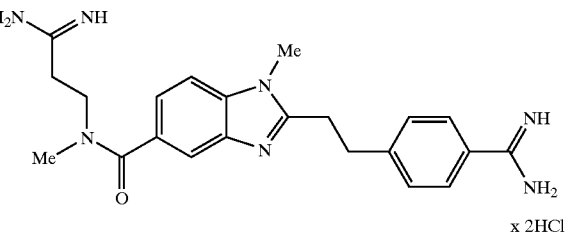

a) 2-[2-(4-Cyanophenyl)-ethyl]-1-methyl-benzimidazol-5-yl-carboxylic Acid-N-(2-cyanoethyl)-N-methyl-amide:

The synthesis is carried out analogously to step f (Example 1) by reacting 4 mmol of 2-[2-(4-cyanophenyl)-ethyl]-1-methyl-benzimidazol-5-yl-carboxylic acid with N-(2-cyanoethyl)-N-methyl-amine. Yield: 61%; melting point: 150–152° C.;

b) 2-[2-(4-Amidinophenyl)-ethyl]-1-methyl-benzimidazol-5-yl-carboxylic Acid-N-(2-amidinoethyl)-N-methyl-amide-dihydrochloride:

The reaction was carried out starting from 2 mmol of 2-[2-(4-cyanophenyl)-ethyl]-1-methyl-benzimidazol-5-yl-carboxylic acid-N-(2-cyanoethyl)-N-methyl-amide analogously to Example 1, step g. The product is obtained by chromatography on silica gel (dichloromethane:methanol= 7:3). Yield: 67%; solid foam; mass: calc.: [405], found: [M+H]$^+$ 406; $^1$H-NMR (250 MHz, CD$_3$OD): δ [ppm]=7.70 (7H, m, aryl-H); 3.88, 2.81 (4H, m, N—CH$_2$—CH$_2$—); 3.71 (3H, s, aryl-N—CH$_3$); 3.29 (4H, s, aryl-CH$_2$—CH$_2$—); 3.08 (3H, s, CO—N—CH$_3$).

EXAMPLE 8

2-[2-(4-Amidinophenyl)-ethyl]-1-methyl-benzimidazol-5-yl-carboxylic Acid-N-(2-amidinoethyl)-N-(quinolin-3-yl-methyl)-amide-dihydrochloride

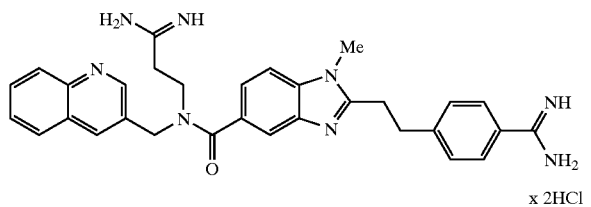

x 2HCl a) 3-(quinolin-3-yl-methyl-amino)-propionitrile:

1.3 mL of acrylonitrile in 4 mL ethanol are added dropwise to a well stirred solution of 3-aminomethyl-quinoline (3.0 g, 19 mmol) in 10 mL of ethanol maintained at not more than 30° C. over a period of about 0.5 h. The mixture is kept for 16 h at ambient temperature, refluxed for 1 h and the solvent is distilled off in vacuo. The residue is chromatographed over silica gel (dichloromethane:methanol 50:1). Yield: 3.0 g (75%); yellow oil;

b) 2-[2-(4-cyanophenyl)-ethyl]-1-methyl-benzimidazol-5-yl-carboxylic Acid-N-(2-cyanoethyl)-N-(quinolin-3-yl-methyl)-amide:

The synthesis is carried out analogously to step f (Example 1) by reacting 5 mmol of 2-[2-(4-cyanophenyl)-ethyl]-1-methyl-benzimidazol-5-yl-carboxylic acid with 3-(quinolin-3-yl-methyl-amino)-propionitrile. The crude product obtained is further reacted directly without any more purification.

c) 2-[2-(4-Amidinophenyl)-ethyl]-1-methyl-benzimidazol-5-yl-carboxylic Acid-N-(2-amidinoethyl)-N-quinolin-3-yl-methyl)-amide-dihydrochloride The reaction was carried out starting from 5 mmol of 2-[2-(4-cyanophenyl)-ethyl]1-methyl-benzimidazol-5-yl-carboxylic acid-N-(2-cyanoethyl)-N-(quinolin-3-yl-methyl)-amide analogously to Example 1, step g. The product is obtained by chromatography on silica gel (dichloromethane:methanol=3:1) or by crystallisation from methanol/acetone.

Yield: 46%; melting point: >220° C.; mass: calc.: [532.65], found: [M+H]$^+$ 533, [M+2H]$^{2+}$ 267; $^1$H-NMR (250 MHz, DMSO-d6): δ [ppm]=7.75–7.40 (13H, m, aryl-H); 5.00 (2H, s, N—CH$_2$-Ph); 4.00, 2.94 (4H, 2 m, N—CH$_2$—CH$_2$—N); 3.86 (3H, s, aryl-N—CH$_3$); 3.41 (4H, s, aryl-CH$_2$—CH$_2$—).

EXAMPLE 9

2-[2-(4-Amidinophenyl)-ethyl]-1-methyl-benzimidazol-5-yl -carboxylic Acid-N-(2-amidinoethyl)-N-benzyl-amide-dihydrochloride

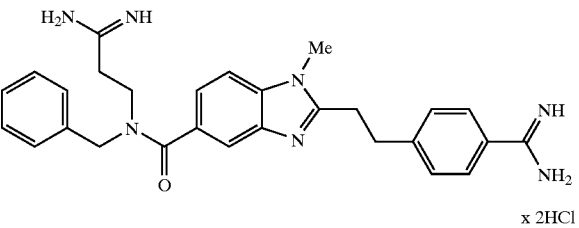

x 2HCl a) 2-[2-(4-Cyanophenyl)-ethyl]-1-methyl-benzimidazol-5-yl-carboxylic Acid-N-(2-cyanoethyl)-N-benzyl-amide:

The synthesis is carried out starting from 4.4 mmol of 2-[2-(4-cyanophenyl)-ethyl]-1-methyl-benzimidazol-5-yl-carboxylic acid by reaction with 3-(benzylamino)-propionitrile analogously to Example 1, step f. The product is purified by crystallisation from ethyl acetate/diethylether.

Yield: 89%. melting point: 140–148° C.

b) 2-[2-(4-Amidinophenyl)-ethyl]-1-methyl-benzimidazol-5-yl-carboxylic Acid-N-(2-amidinoethyl)-N-benzyl-amide-dihydrochloride:

Starting from 2-[2-(4-cyanophenyl)-ethyl]-1-methyl-benzimidazol-5-yl-carboxylic acid-N-(2-cyanoethyl)-N-benzyl-amide; Yield: 56%; melting point: >220° C.; mass: calc.: [481,60] found: [M+H]$^+$ 482, [M+2H]$^{2+}$ 242; $^1$H-NMR (250 MHz, DMSO-d6): δ [ppm]=9.38, 9.26, 9.20, 8.81 (8H, 4 s, 2 C(=NH$_2^+$)NH$_2$); 7.83–7.07 (12H, m, aryl-H); 4.63 (2H, s, N—CH$_2$-Ph); 3.67 (3H, s, aryl-N—CH$_3$); 3.68, 2.76 (4H, 2 m, N—CH$_2$—CH$_2$—N); 3.24 (4H, s, aryl-CH$_2$—CH$_2$).

EXAMPLE 10

2-[2-(4-Amidinophenyl)-ethyl]-1-methyl-benzimidazol-5-yl-carboxylic Acid-N-(2-amidinoethyl)-N-(3-pyridylmethyl)-amide-dihydrochloride

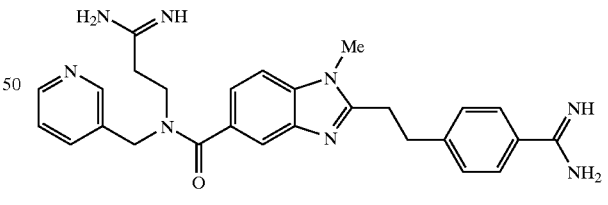

x 2HCl a) 2-[2-(4-cyanophenyl)-ethyl]-1-methyl-benzimidazol-5-yl-carboxylic Acid-N-(2-cyanoethyl)-N-(3-pyridylmethyl)-amide:

The synthesis is carried out analogously to step f (Example 1) by reacting 4.4 mmol of 2-[2-(4-cyanophenyl)-ethyl]-1-methyl-benzimidazol-5-yl-carboxylic acid with 3-(3-pyridyl-methyl-amino)-propionitrile. The crude product obtained is further reacted directly without any more purification.

b) 2-[2-(4-Amidinophenyl)-ethyl]-1-methyl-benzimidazol-5-yl-carboxylic Acid-N-(2-amidinoethyl)-N-(3-pyridylmethyl)-amide-dihydrochloride:

Starting from 2-[2-(4-cyanophenyl)-ethyl]-1-methyl-benzimidazol-5-yl-carboxylic acid-N-(2-cyanoethyl)-N-(3-pyridylmethyl)-amide the synthesis is carried out analogously to Example 1 (step g). The product is purified by chromatography over silica gel (dichloromethane:methanol 7:3) and/or crystallisation from methanol/acetone with water.

Yield: 25%; melting point: 225–228° C.; mass: calc.: [482] found: [M+H]$^+$ 483, [M+2H]$^{2+}$ 242; $^1$H-NMR (250 MHz, DMSO-d6): δ [ppm]=9.41, 9.27, 9.19, 8.77 (8H, 4 s, 2 C($=$NH$_2^+$)NH$_2$); 8.62–7.29 (11H, m, aryl-/pyridyl-H); 4.71 (2H, s, N—CH$_2$-Ph); 3.78 (3H, s, aryl-N—CH$_3$); 3.72, 2.78 (4H, 2 m, N—CH$_2$—CH$_2$); 3.29 (4H, s, aryl-CH$_2$—CH$_2$—).

EXAMPLE 11

2-[2-(4-Amidinophenyl)-ethyl]-1-methyl-benzimidazol-5-yl-carboxylic Acid-N-(2-amidinoethyl)-N-iso-butyl-amide-dihydrochloride

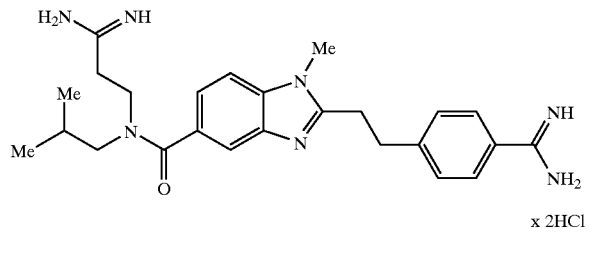

x 2HCl a) 3-(i-Butylamino)-propionitrile

The preparation is carried out starting from 40 mmol of iso-butylamine analogously to step a (Example 8). The product obtained is used directly in the next step without any further purification. Yield: 99%;

b) 2-[2-(4-cyanophenyl)-ethyl]-1-methyl-benzimidazol-5-yl-carboxylic Acid-N-(2-cyanoethyl)-N-iso-butyl-amide:

The synthesis is carried out starting from 2-[2-(4-cyanophenyl)-ethyl]-1-methyl-benzimidazol-5-yl-carboxylic acid chloride by reaction with 3-(i-butylamino)-propionitrile analogously to Example 2, step b. The product is further reacted directly, without being purified.

c) 2-[2-(4-Amidinophenyl)-ethyl]-1-methyl-benzimidazol-5-yl-carboxylic Acid-N-(2-amidinoethyl)-N-iso-butyl-amide-dihydrochloride:

Starting from 2-[2-(4-cyanophenyl)-ethyl]-1-methyl-benzimidazol-5-yl-carboxylic acid-N-(2-cyanoethyl)-N-iso-butyl-amide the synthesis is carried out analogously to the instructions in Example 1 (step g). Yield: 43%; melting point: 204–210° C.; mass: calc.: [447] found: [M+H]$^+$ 448; $^1$H-NMR (250 MHz, DMSO-d6): δ [ppm]=9.56, 9.42, 9.36, 8.96 (8H, 4 s, 2 C($=$NH$_2^+$)NH$_2$); 8.32–7.27 (7H, m, aryl-H); 3.88, 2.79 (4H, 2 m, N—CH$_2$—CH$_2$); 3.35 (2H, m, N—CH$_2$—CH); 3.32 (4H, s, aryl-CH$_2$—CH$_2$—); 1.89 (1H, m, N—CH$_2$—CH); 0.68 (6H, m, CH(CH$_3$)$_2$).

EXAMPLE 12

2-[2-(4-Amidinophenyl)-ethyl]-1-methyl-benzimidazol-5-yl-carboxylic Acid-N-(3-phenylpropyl)-amide-hydrochloride

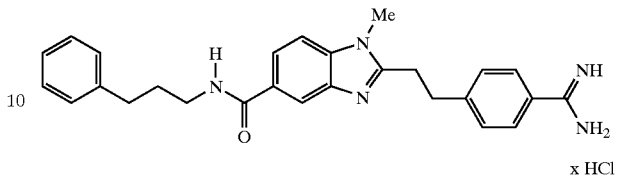

x HCl a) 2-[2-(4-Cyanophenyl)-ethyl]-1-methyl-benzimidazol-5-yl-carboxylic Acid-N-(3-phenylpropyl)-amide:

The synthesis is carried out starting from 6.2 mmol of 2-[2-(4-cyanophenyl)-ethyl]-1-methyl-benzimidazol-5-yl-carboxylic acid by reaction with 3-phenylpropylamine analogously to Example 1, step f. The product is further reacted directly, without being purified. Yield: 89%;

b) 2-[2-(4-Amidinophenyl)-ethyl]-1-methyl-benzimidazol-5-yl-carboxylic Acid-N-(3-phenylpropyl)-amide-hydrochloride:

Starting from 5.4 mmol of 2-[2-(4-cyanophenyl)-ethyl]-1-methyl-benzimidazol-5-yl-carboxylic acid-N-(3-phenylpropyl)-amide the synthesis is carried out analogously to the instructions in Example 1 (step g). The product is purified by chromatography over silica gel (dichloromethane:methanol 9:1). Yield: 56%; amorphous solid; mass: calc. [439,56], found: [M+H]$^+$ 4400; $^1$H-NMR (250 MHz, DMSO-d6): δ [ppm]=9.53, 9.33 (4H, 2 s, C($=$NH$_2^+$)NH$_2$); 8.65 (1H, t, J=5.2 Hz, NHCO); 8.32–7.22 (12H, m, aryl-H); 3.82 (3H, s, aryl-N—CH$_3$); 3.41, 2.70, 1.88 (6H, 3 m, N—CH$_2$—CH$_2$—CH$_2$—); 3.33 (4H, s, aryl-CH$_2$—CH$_2$—).

EXAMPLE 13

2-[2-(4-Amidinophenyl)-ethyl]-1-methyl-benzimidazol-5-yl-carboxylic Acid-N-(3,3-diphenylpropyl)-amide-hydrochloride

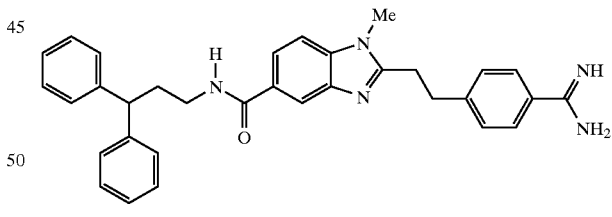

x HCl a) 2-[2-(4-cyanophenyl)-ethyl]-1-methyl-benzimidazol-5-yl-carboxylic Acid-N-(3,3-diphenylpropyl)-amide:

The synthesis is carried out starting from 6.2 mmol of 2-[2-(4-cyanophenyl)-ethyl]-1-methyl-benzimidazol-5-yl-carboxylic acid by reaction with 3,3-diphenylpropylamine analogously to Example 1, step f. The product is further reacted directly, without being purified. Yield: 81%;

b) 2-[2-(4-Amidinophenyl)-ethyl]-1-methyl-benzimidazol-5-yl-carboxylic Acid-N-(3,3-diphenylpropyl)-amide-hydrochloride:

Starting from 5 mmol of 2-[2-(4-cyanophenyl)-ethyl]-1-methyl-benzimidazol-5-yl-carboxylic acid-N-(3,3- diphenylpropyl)-amide the synthesis is carried out analogously to the instructions in Example 1 (step g). The product is purified by chromatography over silica gel (dichloromethane:methanol 95:5).

Yield: 43%; melting point: 185° C.; mass: calc. [515], found: [M+H]+ 516 1H-NMR (250 MHz, DMSO-d6): δ [ppm]=8.63 (1H, t, J=6.2 Hz, NHCO); 8.32–7.25 (17H, m, aryl-H); 7.79 (4 h, broad, c(=NH2+)NH2); 4.15 (1H, t, J=6.8 Hz, —CHPh2); 381 (3H, s, aryl-N—CH3); 3.32 (4H, s, aryl-CH2—CH2—); 3.26, 2.36 (4H, 2 m, N—CH2—CH2—).

EXAMPLE 14

2-[2-(4-Amidinophenyl)-ethyl]-1-methyl-benzimidazol-5-yl-carboxylic Acid-(N'-phenyl-piperazide)-hydrochloride

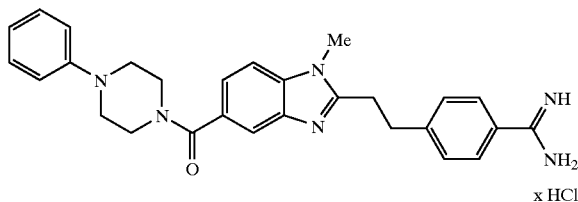

a) 2-[2-(4-cyanophenyl)-ethyl]-1-methyl-benzimidazol-5-yl-carboxylic Acid-(N'-phenyl-piperazide):

The synthesis is carried out starting from 6.2 mmol of 2-[2-(4-cyanophenyl)-ethyl]-1-methyl-benzimidazol-5-yl-carboxylic acid by reaction with N-phenylpiperazine analogously to Example 1, step f. The product is further reacted directly, without any more purification. Yield: 86%;

b) 2-[2-(4-Amidinophenyl)-ethyl]-1-methyl-benzimidazol-5-yl-carboxylic Acid-(N'-phenyl-piperazide)-hydrochloride:

Starting from 5.4 mmol of 2-[2-(4-cyanophenyl)-ethyl]-1-methyl-benzimidazol-5-yl-carboxylic acid-(N'-phenyl-piperazide) the synthesis is carried out analogously to the instructions in Example 1 (step g). The product is purified by chromatography over silica gel (dichloromethane:methanol 95:5). Yield: 47%; amorphous solid; mass: calc.: [466,59], found: [M+H]+ 467; 1H-NMR (250 MHz, DMSO-d6): δ [ppm]=9.41, 9.22 (4H, 2 s, C(=NH2+)NH2); 7.89–6.79 (12H, m, aryl-H); 3.80 (3H, s, aryl-N—CH3); 3.69, 3.19 (8H, 2 m, piperazinyl); 3.29 (4H, s, aryl-CH2—CH2—).

EXAMPLE 15

2-[2-(4-Amidinophenyl)-ethyl]-1-methyl-benzimidazol-5-yl-carboxylic Acid-[N'-(2-methyl-phenyl)-diazepide]-hydrochloride

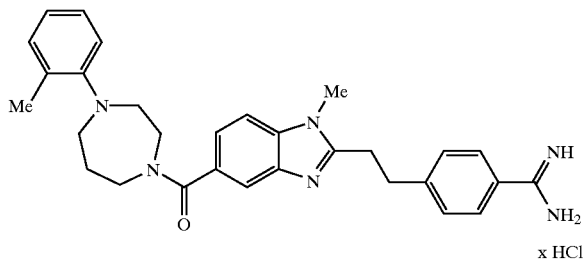

a) 2-[2-(4-cyanophenyl)-ethyl]-1-methyl-benzimidazol-5-yl-carboxylic acid-[N'-(2-methyl-phenyl)-diazepide]:

The synthesis is carried out starting from 6.2 mmol of 2-[2-(4-cyanophenyl)-ethyl]-1-methyl-benzimidazol-5-yl-carboxylic acid by reaction with N-(2-methylphenyl)-diazepine analogously to Example 1, step f. The product is further reacted directly, without being purified.

1H-NMR (250 MHz, CDCl3): δ [ppm]=7.87–6.90 (11H, m, aryl-H); 3.96, 3.65, 3.11, 2.31, 1.94 (10H, 5 m, diazacycloheptyl); 3.62 (3H, s, N—CH3); 3.34, 3.27 (4H, 2 m, aryl-CH2CH2); 2.81 (3H, s, aryl-N—CH3).

b) 2-[2-(4-Amidinophenyl)-ethyl]-1-methyl-benzimidazol-5-yl-carboxylic Acid-[N'-(2-methyl-phenyl)-diazepide]-hydrochloride:

Starting from 2.5 mmol of 2-[2-(4-cyanophenyl)-ethyl]-1-methyl-benzimidazol-5-yl-carboxylic acid-[N'-(2-methyl-phenyl)-diazepide] the synthesis is carried out analogously to the instructions in Example 1 (step g). The product is purified by chromatography over silica gel (dichloromethane:methanol 95:5).

Yield: 48%; amorphous solid; mass: calc.: [494], found: [M+H]+ 495; 1H-NMR (250 MHz, DMSO-d6): δ [ppm]= 9.42, 9.21 (4H, 2 s, C(=NH2+)NH2); 7.92–6.87 (11H, m, aryl-H); 3.84–1.65 (10H, 5 m, diazacycloheptane); 3.78 (3H, s, aryl-N—CH3); 3.30 (4H, s, aryl-CH2—CH2—); 2.21 (3H, s, aryl-CH3).

EXAMPLE 16

2-[2-(4-Amidinophenyl)-ethyl]-1-methyl-benzimidazol-5-yl-carboxylic Acid-N-(4-amidinobenzyl)-N-(3-phenylpropyl)-amide-dihydrochloride

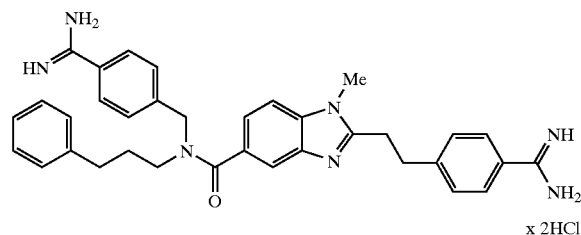

a) (4-Cyanobenzyl)-(3-phenyl-propyl)-amine:

3-phenylpropylamine (2.5 g, 18.5 mmol), 4-cyanobenzaldehyde (2.2 g, 16.8 mmol) and 0.22 mL acetic acid in 130 mL dichloromethane are combined with 11.0 g of Na[BH(OAc)3] (51.9 mmol) with stirring. The mixture is stirred for 1 h at RT, the dichloromethane is distilled off, taken up in ethyl acetate, combined with water and made acidic with dilute hydrochloric acid. Once the development of gas is no longer visible, the mixture is made alkaline with 4 N aqueous sodium hydroxide solution, the amine is extracted into the organic phase and the organic phase is washed with water and dried. The solvent is distilled off in vacuo and the crude product remaining (according to 1H-NMR: 079381, 85%) is chromatographed over silica gel (dichloromethane:petroleum ether 9:1 to dichloromethane).

Yield: 3.6 g (78%).

b) 2-[2-(4-Cyanophenyl)-ethyl]-1-methyl-benzimidazol-5-yl-carboxylic Acid-N-(4-cyanobenzyl)-N-(3-phenylpropyl)-amide:

The synthesis is carried out starting from 15.2 mmol of 2-[2-(4-cyanophenyl)-ethyl]-1-methyl-benzimidazol-5-yl-carboxylic acid by reaction with (4-cyanobenzyl)-(3-phenyl-propyl)-amine analogously to Example 1, step f. The product is further reacted directly, without being purified. Yield: >90%;

c) 2-[2-(4-Amidinophenyl)-ethyl]-1-methyl-benzimidazol-5-yl-carboxylic Acid-N-(4-amidinobenzyl)-N-(3-phenylpropyl)-amide-dihydrochloride:

Starting from 7.4 mmol of 2-[2-(4-cyanophenyl)-ethyl]-1-methyl-benzimidazol-5-yl-carboxylic acid-N-(4-cyanobenzyl)-N-(3-phenylpropyl)-amide the synthesis is carried out analogously to the instructions in Example 1 (step g). The product is purified by chromatography over silica gel (dichloromethane:methanol 95:5–9:1).

Yield: 18%; amorphous solid; mass: calc.: [571] found: [M+H]+ 572; 1H-NMR (250 MHz, CD3OD): δ [ppm]= 7.88–6.70 (16H, m, aryl-H); 3.75 (5H, s, N—CH2, aryl-N—CH3); 3.34 (4H, s, aryl-CH2—CH2—); 3.50–1.68 (6H, m, N—CH2—CH2—CH2).

EXAMPLE 17

2-[2-(4-Amidinophenyl)-ethyl]-1-methyl-benzimidazol-5-yl-carboxylic Acid-N-(4-amidinobenzyl)-N-(3,3-diphenylpropyl)-amide-dihydrochloride

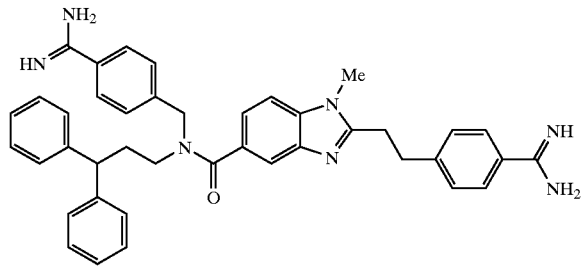

x 2HCl a) (4-Cyanobenzyl)-(3-phenyl-propyl)-amine:

The reaction is carried out analogously to the procedure described in Example 16 (step a) starting from 18.5 mmol of 3,3-diphenylpropylamine. Yield: 65%;

b) 2-[2-(4-Cyanophenyl)-ethyl]-1-methyl-benzimidazol-5-yl-carboxylic Acid-N-(4-cyanobenzyl)-N-(3,3-diphenylpropyl)-amide:

The synthesis is carried out starting from 12.1 mmol of 2-[2-(4-cyanophenyl)-ethyl]-1-methyl-benzimidazol-5-yl-carboxylic acid by reaction with (4-cyanobenzyl)-(3,3-diphenyl-propyl)-amine analogously to Example 1, step f. The product is further reacted directly, without any more purification. Yield: >90%;

c) 2-[2-(4-Amidinophenyl)-ethyl]-1-methyl-benzimidazol-5-yl-carboxylic Acid-N-(4-amidinobenzyl)-N-(3,3-diphenylpropyl)-amide-dihydrochloride:

Starting from 5.4 mmol of 2-[2-(4-cyanophenyl)-ethyl]-1-methyl-benzimidazol-5-yl-carboxylic acid-N-(4-cyanobenzyl)-N-(3,3-diphenylpropyl)-amide the synthesis is carried out analogously to the instructions in Example 1 (step g). The product is purified by chromatography over silica gel (dichloromethane:methanol 85:15).

Yield: 26%; amorphous solid; mass: calc.: [647], found: [M+H]+ 648; [M+2H]2+ 325; 1H-NMR (250 MHz, CD3OD): δ [ppm]=7.85–6.81 (21H, m, aryl-H); 3.80 (3H, s, aryl-N—CH3); 4.16–2.13 (11H, m, aryl-CH2—CH2, N—CH2, N—CH2—CH2—CH).

EXAMPLE 18

2-[2-(4-Amidinophenyl)-ethyl]-1-methyl-benzimidazol-5-yl-carboxylic Acid-N-methyl-N-(3-pyridyl)-amide-hydrochloride

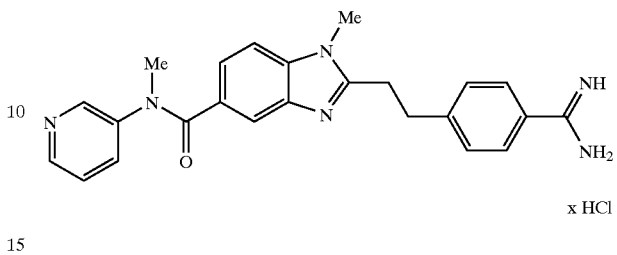

x HCl a) 2-[2-(4-Cyanophenyl)-ethyl]-1-methyl-benzimidazol-5-yl-carboxylic acid-N-methyl-N-(3-pyridyl)-amide:

The synthesis is carried out starting from 10 mmol of 2-[2-(4-cyanophenyl)-ethyl]-1-methyl-benzimidazol-5-yl-carboxylic acid chloride by reaction with N-methyl-N-(3-pyridyl)-amine analogously to Example 2, step b. The product is further reacted directly, without any more purification.

b) 2-[2-(4-Amidinophenyl)-ethyl]-1-methyl-benzimidazol-5-yl-carboxylic Acid-N-methyl-N-(3-pyridyl)-amide-hydrochloride:

Starting from 5 mmol of 2-[2-(4-cyanophenyl)-ethyl]-1-methyl-benzimidazol-5-yl-carboxylic acid-N-methyl-N-(3-pyridyl)-amide the synthesis is carried out analogously to the instructions in Example 1 (step g). The product is purified by chromatography over silica gel (dichloromethane:methanol 4:1).

Yield: 22%; melting point: >220° C.; mass: calc.: [412], found: [M+H]+ 413, [2M+H]+ 825; 1H-NMR (250 MHz, DMSO-d6): δ [ppm]=9.30 (4H, s, C(=NH2+)NH2); 8.40–7.10 (11H, m, aryl-/pyridyl-H); 3.69 (3H, s, aryl-N—CH3); 3.42 (3H, s, CO—N—CH3); 3.21 (4H, s, aryl-CH2—CH2—).

EXAMPLE 19

2-[2-(4-Amidinophenyl)-ethyl]-1-methyl-benzimidazol-5-yl-carboxylic Acid-N-[2-N',N'-dibenzylamino)ethyl]-N-phenyl-amide-dihydrochloride

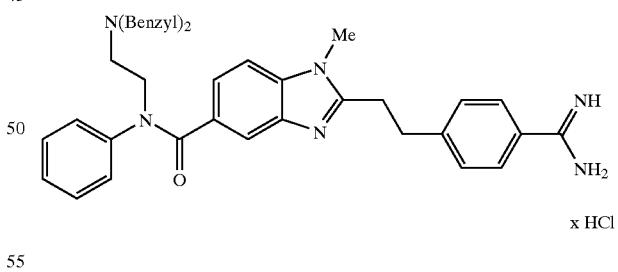

x HCl a) N,N-dibenzyl-N'-phenyl-ethylenediamine is obtained from
N,N-dibenzylethanolamine-hydrochloride by reaction with SOCl2 in chloroform and subsequent nucleophilic substitution with aniline.

b) 2-[2-(4-cyanophenyl)-ethyl]-1-methyl-benzimidazol-5-yl-carboxylic Acid-N-[2-N',N'-dibenzylamino)ethyl]-N-phenyl-amide:

The synthesis is carried out starting from 10.4 mmol of 2-[2-(4-cyanophenyl)-ethyl]-1-methyl-benzimidazol-5-yl-carboxylic acid chloride by reaction with N,N-dibenzyl- N'-phenylethylenediamine analogously to Example 2, step b. The product is obtained by crystallisation from diethylether. Yield: 92%;

c) 2-[2-(4-Amidinophenyl)-ethyl]-1-methyl-benzimidazol-5-yl-carboxylic Acid-N-[2-N',N'-dibenzylamino)ethyl]-N-phenyl-amide-dihydrochloride:

Starting from 8.3 mmol of 2-[2-(4-cyanophenyl)-ethyl]-1-methyl-benzimidazol-5-yl-carboxylic acid-N-[2-N',N'-dibenzylamino)ethyl]-N-phenyl-amide the synthesis is carried out analogously to the instructions in Example 1 (step g). The product is purified by chromatography over silica gel (dichloromethane:methanol 95:5).

Yield: 70%; amorphous solid; mass: calc.: [620], found: [M+H]$^+$ 621, [M+2H]$^{2+}$ 311; $^1$H-NMR (250 MHz, DMSO-d6): δ [ppm]=9.34, 9.13 (4H, 2 s, C(=NH$_2^+$)NH$_2$); 7.84–6.90 (22H, m, aryl-H); 4.05, 2.66 (4H, 2 t, J=6.2 Hz, N—CH$_2$—CH$_2$—N); 3.67 (3H, s, aryl-N—CH$_3$); 3.57 (4H, s, N-(CH$_2$-Ph)$_2$); 3.20 (4H, s, aryl-CH$_2$—CH$_2$—).

EXAMPLE 20

2-[2-(4-Amidinophenyl)-ethyl]-1-methyl-benzimidazol-5-yl-carboxylic Acid-N-(2-amidinoethyl)-N-(2-naphthyl)-amide-dihydrochloride

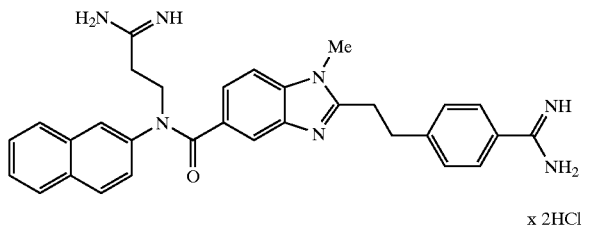

x 2HCl a) 3-(β-Naphthyl-amino)propionitrile:

The reaction is carried out starting from 24 mmol of 2-amino-naphthaline analogously to EXAMPLE 22 (step a). The N-cyanoethyl-N-formylnaphthylamine is purified by crystallisation from ethanol (Yield: 68%; melting point: 82–84° C.). The end product is recrystallised from ethanol (Yield: 68%).

melting point: 96–98° C.;

b) 2-[2-(4-Cyanophenyl)-ethyl]-1-methyl-benzimidazol-5-yl-carboxylic Acid-N-(2-cyanoethyl)-N-(2-naphthyl)-amide:

The synthesis is carried out starting from 3.8 mmol of 2-[2-(4-cyanophenyl)-ethyl]-1-methyl-benzimidazol-5-yl-carboxylic acid chloride by reaction with 3-(-naphthyl-amino)propionitrile analogously to Example 2, step b. The product is obtainable by crystallisation from ethyl acetate. Yield: 50%; melting point: 196–98° C.; $^1$H-NMR (250 MHz, DMSO-d6): δ [ppm]=7.85–7.12 (14H, m, aryl-H); 4.19, 2.89 (4H, 2 m, N—CH$_2$—CH$_2$); 3.55 (3H, s, aryl-N—CH$_3$); 3.08 (4H, s, aryl-CH$_2$—CH$_2$—).

c) 2-[2-(4-Amidinophenyl)-ethyl]-1-methyl-benzimidazol-5-yl-carboxylic Acid-N-(2-amidinoethyl)-N-(2-naphthyl)-amide-dihydrochloride:

Starting from 1.9 mmol of 2-[2-(4-cyanophenyl)-ethyl]-1-methyl-benzimidazol-5-yl-carboxylic acid-N-(2-cyanoethyl)-N-(2-naphthyl)-amide the title compound is synthesised analogously to Example 1 (step g).

Yield: 55%; amorphous solid; mass: calc.: [517], found: [M+H]$^+$ 518; $^1$H-NMR (250 MHz, CD$_3$OD): δ [ppm]= 7.80–7.12 (14H, m, aryl-H); 4.39, 2.89 (4H, 2 m, N—CH$_2$—CH$_2$); 3.55 (3H, s, aryl-N—CH$_3$); 3.15 (4H, s, aryl-CH$_2$—CH$_2$—).

EXAMPLE 21

2-[2-(4-Amidinophenyl)-ethyl]-1-methyl-benzimidazol-5-yl-carboxylic Acid-N-(2-amidinoethyl)-N-phenyl-amide-dihydrochloride

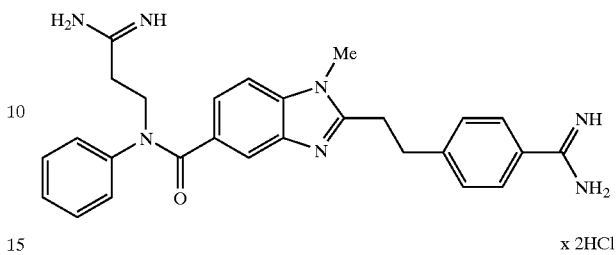

x 2HCl a) 2-[2-(4-Cyanophenyl)-ethyl]-1-methyl-benzimidazol-5-yl-carboxylic Acid-N-(2-cyanoethyl)-N-phenyl-amide:

The synthesis is carried out starting from 6.6 mmol of 2-[2-(4-cyanophenyl)-ethyl]-1-methyl-benzimidazol-5-yl-carboxylic acid chloride by reaction with 3-phenylamino-propionitrile analogously to Example 2, step b. The product can be obtained by crystallisation from ethyl acetate. Yield: 70%; melting point: 188–190° C.;

b) 2-[2-(4-Amidinophenyl)-ethyl]-1-methyl-benzimidazol-5-yl-carboxylic Acid-N-(2-amidinoethyl)-N-phenyl-amide-dihydrochloride:

Starting from 4.1 mmol of 2-[2-(4-cyanophenyl)-ethyl]-1-methyl-benzimidazol-5-yl-carboxylic acid-N-(2-cyanoethyl)-N-phenyl-amide the reaction takes place analogously to Example 1, step g. Yield: 62%; amorphous solid; mass: calc.: [467], found: [M+H]$^+$ 468; $^1$H-NMR (250 MHz, DMSO-d6): δ [ppm]=9.48, 9.30, 8,97, 8.60 (8H, 4 s, 2 C(=NH$_2^+$)NH$_2$); 8.00, 7.13 (12H, m, aryl-H); 2.82 (4H, 2 t, J=6.2 Hz, N—CH$_2$—CH$_2$—); 3.71 (3H, s, aryl-N—CH$_3$); 3.22 (4H, s, aryl-CH$_2$—CH$_2$—).

EXAMPLE 22

2-[2-(4-Amidinophenyl)-ethyl]-1-methyl-benzimidazol-5-yl-carboxylic Acid-N-(2-amidinoethyl)-N-(3-ethyl-phenyl)-amide-dihydrochloride

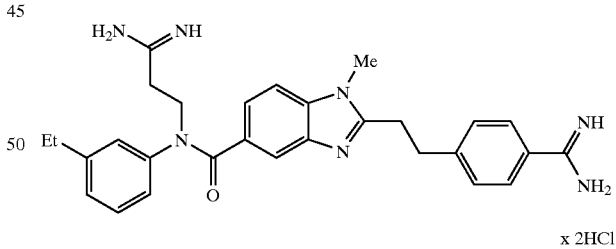

x 2HCl a) 3-(3-Ethylphenyl-amino)-propionitrile:

6.1 g (50 mmol) of 3-ethylaniline are heated in 5 mL of formic acid for 5 h to 100–120° C. and, after cooling, combined with 100 mL ethyl acetate. The mixture is then washed with dilute aqueous hydrochloric acid and with dilute aqueous sodium hydroxide solution. The organic phase is dried over magnesium sulphate and the solvent is distilled off in vacuo. The residue remaining (6.7 g of N-formyl-3-ethylaniline) is taken up in 4.6 mL of acrylonitrile, combined with powdered sodium hydroxide (0.2 g), stirred for 6 h at 80–90° C. and kept at ambient temperature for 16 h. It is diluted with 100 mL of ethyl acetate and washed with water. It is then dried over magnesium sulphate and the solvent is distilled off in vacuo. The residue (8.7 g of N-formyl-3-(3-ethylphenyl-amino)-propionitrile) is taken up in 22.5 mL of acetonitrile, combined with 22.5 mL of aqueous hydrochloric acid (5N) and stirred for 5 h at 80–90° C. It is diluted with 100 mL of ethyl acetate, poured onto water and made alkaline with sodium hydroxide. The organic phase is washed with water, dried over magnesium sulphate and the solvent is distilled off in vacuo. The pure product is obtained by chromatography over silica gel (hexane:ethyl acetate 9:1). Yield: 6.0 g (69%)

b) 2-[2-(4-Cyanophenyl)-ethyl]-1-methyl-benzimidazol-5-yl-carboxylic Acid-N-(2-cyanoethyl)-N-(3-ethyl-phenyl)-amide:

The synthesis is carried out starting from 4.5 mmol of 2-[2-(4-cyanophenyl)-ethyl]-1-methyl-benzimidazol-5-yl-carboxylic acid chloride by reaction with 3-(3-ethylphenyl-amino)-propionitrile analogously to Example 2, step b. The product can be obtained by crystallisation from ethyl acetate. Melting point: 122–124° C.;

c) 2-[2-(4-Amidinophenyl)-ethyl]-1-methyl-benzimidazol-5-yl-carboxylic Acid-N-(2-amidinoethyl)-N-(3-ethyl-phenyl)-amide-dihydrochloride:

Starting from 4.5 mmol of 2-[2-(4-cyanophenyl)-ethyl]-1-methyl-benzimidazol-5-yl-carboxylic acid-N-(2-cyanoethyl)-N-(3-ethyl-phenyl)-amide the reaction takes place analogously to Example 1, step g.

Yield: 43%; amorphous solid; mass: calc.: [495] found: [M+H]$^+$ 496, [M+2H]$^{2+}$ 249; $^1$H-NMR (250 MHz, DMSO-d6): δ [ppm]=9.47, 9.30, 9.27, 8.87 (8H, 4 s, 2 C(=NH$_2^+$) NH$_2$); 7.94–6.96 (11H, m, aryl-H); 4.22, 2.82 (4H, 2 m, N—CH$_2$—CH$_2$); 3H, s, aryl-N—CH$_3$); 3.21 (4H, s, aryl-CH$_2$—CH$_2$—); 2.51 (2H, q, J=7.6 Hz, —Ph—CH$_2$—CH$_3$); 1.01 (3H, t, J=7.6 Hz, —Ph—CH$_2$—CH$_3$).

EXAMPLE 23

2-[2-(4-Amidinophenyl)-ethyl]-1-methyl-benzimidazol-5-yl-carboxylic Acid-N-(2-amidinoethyl)-N-(3-phenoxy-phenyl)-amide-dihydrochloride

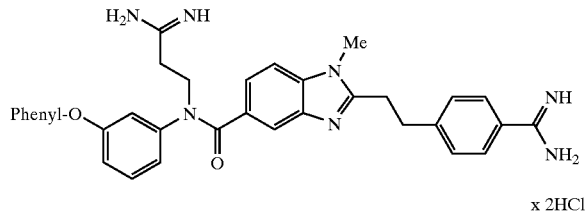

a) 3-(3-Phenoxyphenyl-amino)-propionitrile:

The reaction takes place analogously to the synthesis according to Example 22, step a, starting from 3-phenoxyaniline. The product is purified by crystallisation of the hydrochloride from ethyl acetate with ethereal hydrochloric acid solution.

Yield: 72; melting point: 141–146° C. (hydrochloride)

b) 2-[2-(4-Cyanophenyl)-ethyl]-1-methyl-benzimidazol-5-yl-carboxylic Acid-N-(2-cyanoethyl)-N-(3-phenoxy-phenyl)-amide:

The synthesis is carried out starting from 4.5 mmol of 2-[2-(4-cyanophenyl)-ethyl]-1-methyl-benzimidazol-5-yl-carboxylic acid chloride by reaction with 43-(3-phenoxyphenyl-amino)-propionitrile analogously to Example 2, step b. The product can be obtained by crystallisation from ethyl acetate/diethylether. Melting point: 125–127° C.; $^1$H-NMR (250 MHz, CDCl$_3$): δ [ppm]= 7.70–6.53 (16H, m, aryl-H); 4.16, 2.82 (4H, 2 t, J=7.5 Hz, N—CH$_2$—CH$_2$); 3.55 (3H, s, aryl-N—CH$_3$); 3.28, 3.15 (4H, 2 m, aryl-CH$_2$—CH$_2$).

c) 2-[2-(4-Amidinophenyl)-ethyl]-1-methyl-benzimidazol-5-yl-carboxylic Acid-N-(2-amidinoethyl)-N-(3-phenoxy-phenyl)-amide-dihydrochloride:

Starting from 4.5 mmol of 2-[2-(4-cyanophenyl)-ethyl]-1-methyl-benzimidazol-5-yl-carboxylic acid-N-(2-cyanoethyl)-N-(3-phenoxy-phenyl)-amide the reaction takes place analogously to Example 1, step g. Yield: 23%; amorphous solid; mass: calc.: [559] found: [M+H]$^+$ 560; $^1$H-NMR (250 MHz, CD$_3$OD): δ [ppm]=7.75–6.40(16H, m, aryl-H); 4.30, 2.76 (4H, 2 m, N—CH$_2$—CH$_2$); 3.73 (3H, s, aryl-N—CH$_3$); 3.30 (4H, s, aryl-CH$_2$—CH$_2$—).

EXAMPLE 24

2-[2-(4-Amidinophenyl)-ethyl]-1-methyl-benzimidazol-5-yl-carboxylic Acid-N-(2-amidinoethyl)-N-(2-phenylethyl)-amide-dihydrochloride

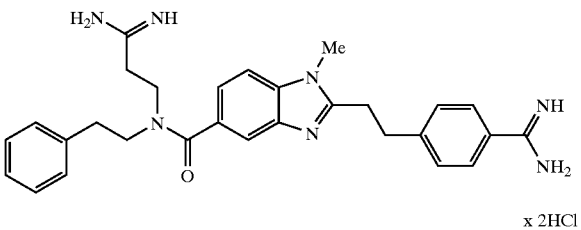

a) 3-(Phenethylamino)-propionitrile

The preparation is carried out analogously to Example 8 (step a) starting from 19 mmol of phenethylamine. Yield: 79%;

b) 2-[2-(4-Cyanophenyl)-ethyl]-1-methyl-benzimidazol-5-yl-carboxylic Acid-N-(2-cyanoethyl)-N-(2-phenylethyl)-amide:

The synthesis is carried out starting from 4.5 mmol of 2-[2-(4-cyanophenyl)-ethyl]-1-methyl-benzimidazol-5-yl-carboxylic acid chloride by reaction with 3-(phenethylamino)-propionitrile analogously to Example 2, step b. The product can be obtained by crystallisation from ethyl acetate/diethylether. Melting point: 132–133° C.;

c) 2-[2-(4-Amidinophenyl)-ethyl]-methyl-benzimidazol-5-yl-carboxylic Acid-N-(2-amidinoethyl)-N-(2-phenylethyl)-amide-dihydrochloride Starting from 3.8 mmol of 2-[2-(4-cyanophenyl)-ethyl]-1-methyl-benzimidazol-5-yl-carboxylic acid-N-(2-cyanoethyl)-N-(2-phenylethyl)-amide the reaction takes place analogously to Example 1, step g. The purification is carried out by chromatography over silica gel (dichloromethane:methanol 4:1–7:3) and/or crystallisation from methanol/acetone with water. Yield: 52%; melting point: 185–190° C.; mass: calc.: [495] found: [M+H]$^+$ 496; $^1$H-NMR (250 MHz, DMSO-d6): δ [ppm]=9.38, 9.26, 9.19, 8.77 (8H, 4 s, 2 C(=NH$_2^+$)NH$_2$);7.84–6.83 (12H, m, aryl-H); 3.84, 2.78 (4H, 2 m, N—CH$_2$—CH$_2$); s, aryl-N—CH$_3$); 3.46, 2.78 (4H, 2 m, N—CH$_2$—CH$_2$-Ph); 3.26 (4H, s, aryl-CH$_2$–CH$_2$)

EXAMPLE 25

2-[2-(4-Amidinophenyl)-ethyl]-1-methyl-
benzimidazol-5-yl-carboxylic Acid-N-(2-
amidinoethyl)-N-cyclooctyl-amide-dihydrochloride

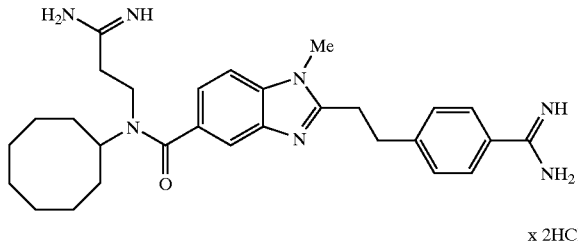

x 2HCl a) 2-[2-(4-Cyanophenyl)-ethyl]-1-methyl-benzimidazol-5-yl-carboxylic Acid-N-(2-cyanoethyl)-N-cyclooctyl-amide:

The synthesis is carried out starting from 4.5 mmol of 2-[2-(4-cyanophenyl)-ethyl]-1-methyl-benzimidazol-5-yl-carboxylic acid chloride by reaction with 3-(cyclooctylamino)-propionitrile analogously to Example 2, step b. The product can be obtained by crystallisation from ethyl acetate. Melting point: 181–183° C.;

b) 2-[2-(4-Amidinophenyl)-ethyl]-1-methyl-benzimidazol-5-yl-carboxylic Acid-N-(2-amidinoethyl)-N-cyclooctyl-amide-dihydrochloride:

Starting from 3.8 mmol of 2-[2-(4-cyanophenyl)-ethyl]-1-methyl-benzimidazol-5-yl-carboxylic acid-N-(2-cyanoethyl)-N-cyclooctyl-amide the reaction takes place analogously to Example 1, step g. The purification is carried out by chromatography over silica gel (dichloromethane:methanol 4:1) and/or crystallisation from methanol/acetone with water.

Yield: 47%; melting point: 200–210° C.; mass: calc.: [501] found: [M+H]$^+$ 502; $^1$H-NMR (250 MHz, DMSO-d6): δ [ppm]=9.33, 9.18, 9.13, 8.77 (8H, 4 s, 2 C(=NH$_2^+$)NH$_2$); 7.82–7.01 (8H, m, aryl-H); 3.88 (1H, m, N—CH-cyclooctyl); 3.74 (3H, s, aryl-N—CH$_3$); 3.58, 2.79 (4H, 2 m, N—CH$_2$—CH$_2$); 3.24 (4H, s, aryl-CH$_2$—CH$_2$—); 1.95–0.74 (14H, m, cyclooctyl).

EXAMPLE 26

2-[2-(4-Amidinophenyl)-ethyl]-1-methyl-
benzimidazol-5-yl-carboxylic Acid-N-(2-
amidinoethyl)-N-(4-methyl-phenyl)-amide-
dihydrochloride

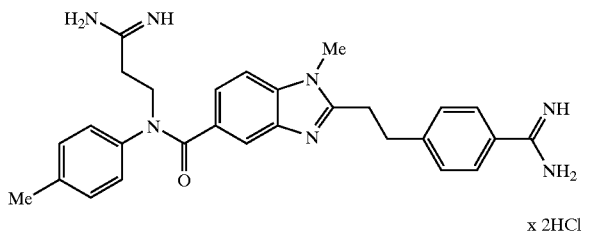

x 2HCl a) 3-(p-Toluyl-amino)-propionitrile:

The reaction takes place analogously to the synthesis according to Example 22, step a, starting from 4-methylaniline. The product is purified by chromatography over silica gel (hexane:ethyl acetate 9:1) and/or crystallisation from hexane.

Yield: 69%;

b) 2-[2-(4-Cyanophenyl)-ethyl]-1-methyl-benzimidazol-5-yl-carboxylic Acid-N-(2-cyanoethyl)-N-(4-methyl-phenyl)-amide:

The synthesis is carried out starting from 4.5 mmol of 2-[2-(4-cyanophenyl)-ethyl]-1-methyl-benzimidazol-5-yl-carboxylic acid chloride by reacting 3-(p-toluyl-amino)-propionitrile analogously to Example 2, step b. The product can be obtained by crystallisation from ethyl acetate/diethylether. Melting point: 149–152° C.;

c) 2-[2-(4-Amidinophenyl)-ethyl]-1-methyl-benzimidazol-5-yl-carboxylic Acid-N-(2-amidinoethyl)-N-(4-methyl-phenyl)-amide-dihydrochloride:

Starting from 2-[2-(4-cyanophenyl)-ethyl]-1-methyl-benzimidazol-5-yl-carboxylic acid-N-(2-cyanoethyl)-N-(4-methyl-phenyl)-amide the reaction takes place analogously to Example 1, step g. Yield: 44%; melting point: 222–225° C.; mass: calc.: [481] found: [M+H]$^+$ 482; $^1$H-NMR (250 MHz, DMSO-d6): δ [ppm]=9.41, 9.25, 9.18, 8.80 (8H, 4 s, 2 C(=NH$_2^+$)NH$_2$); 7.89–7.01 (11 H, m, aryl-H); 4.15, 2.78 (4H, 2 m, N—CH$_2$—CH$_2$); 3.67 (3H, s, aryl-N—CH$_3$); 3.18 (4H, s, aryl-CH$_2$—CH$_2$—); 2.20 (3H, s, aryl-C$\underline{H}_3$).

EXAMPLE 27

2-[2-(4-Amidinophenyl)-ethyl]-1-methyl-
benzimidazol-5-yl-carboxylic Acid-N-(2-
amidinoethyl)-N-iso-propyl-amide-dihydrochloride

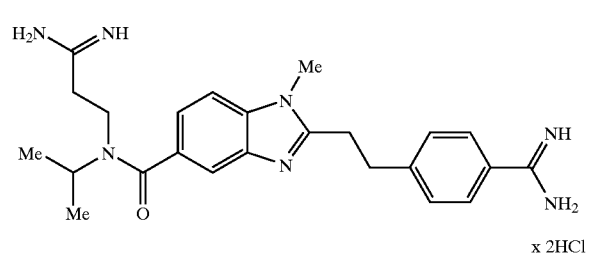

x 2HCl a) 3-(i-propylamino)-propionitrile:

The synthesis is carried out analogously to Example 8 (step a) starting from 40 mmol of isopropylamine. The product obtained is reacted further directly with no additional purification. Yield: 89%;

b) 2-[2-(4-Cyanophenyl)-ethyl]-1-methyl-benzimidazol-5-yl-carboxylic Acid-N-(2-cyanoethyl)-N-iso-propyl-amide:

The synthesis is carried out starting from 3.1 mmol of 2-[2-(4-cyanophenyl)-ethyl]-1-methyl-benzimidazol-5-yl-carboxylic acid chloride by reaction with 3-(i-propylamino)-propionitrile analogously to Example 2, step b. The product can be obtained by crystallisation from ethyl acetate/diethylether and is used directly in the next step.

c) 2-[2-(4-Amidinophenyl)-ethyl]-1-methyl-benzimidazol-5-yl-carboxylic Acid-N-(2-amidinoethyl)-N-iso-propyl-amide-dihydrochloride:

Starting from 3.1 mmol of 2-[2-(4-cyanophenyl)-ethyl]-1-methyl-benzimidazol-5-yl-carboxylic acid-N-(2-cyanoethyl)-N-iso-propyl-amide the reaction takes place analogously to Example 1, step g. The product is purified by chromatography over silica gel (dichloromethane:methanol 4:1–7:3) and/or crystallisation from methanol/acetone with water. Yield: 59%; melting point: 195–200° C.; mass: calc.: [433] found: [M+H]$^+$ 434; $^1$H-NMR (250 MHz, DMSO-d6): δ [ppm]=9.93, 9.22, 9.20, 8.80 (8H, 4 s, 2 C(=NH$_2^+$)NH$_2$);

7.89–7.19 (7H, m, aryl-H); 3.39 (1H, m, N—CH-Me₂); 3.65, 2.74 (4H, 2 m, N—CH₂—CH₂); 3.78 (3H, s, aryl-N—CH₃); 3.29 (4H, s, aryl-CH₂—CH₂—); 1.12 (6H, d, J=6.7 Hz, CH(CH₃)₂).

EXAMPLE 28

Ethyl 2-{2-[2-(4-Amidinophenyl)-ethyl]-1-methyl-benzimidazol-5-yl-carbonylamino}-3-(4-amidinophenyl)-propionate

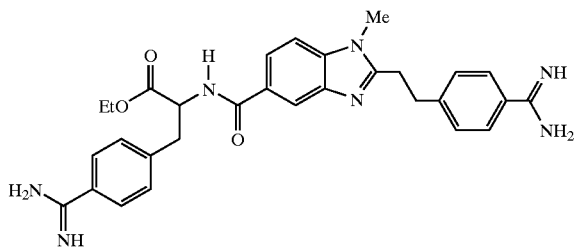

a) ethyl 2-{2-[2-(4-cyanophenyl)-ethyl]-1-methyl-benzimidazol-5-yl-carbonylamino}-3-(4-cyanophenyl)-propionate:

The synthesis is carried out starting from 5 mmol of 2-[2-(4-cyanophenyl)-ethyl]-1-methyl-enzimidazol-5-yl-carboxylic acid by reaction with ethyl 2-amino-3-(4-cyanophenyl)-propionate analogously to Example 1, step f. The product is chromatographed over silica gel (dichloromethane:methanol 50:1). Yield: 92%; ¹H-NMR (250 MHz, DMSO-d6): δ [ppm]=8.26–7.37 (11H, m, aryl-H); 6.87 (1H, m, NHCO); 5.23 (1H, m, NH—CH—); 4.32 (2H, q, J=7.5 Hz, —O—CH₂); 3.86 (3H, s, OCH₃); 3.78 (3H, s, aryl-N—CH₃); 3.56–3.19 (6H, m, aryl-CH₂, aryl-CH₂—CH₂—); 1.31 (3H, t, J=7.5 Hz, —O—CH₂—CH₃).

b) Ethyl 2-{2-[2-(4-Amidinophenyl)-ethyl]-1-methyl-benzimidazol-5-yl-carbonylamino}-3-(4-amidinophenyl)-propionate:

Starting from 5 mmol of ethyl 2-{2-[2-(4-cyanophenyl)-ethyl]-1-methyl-benzimidazol-5-yl-carbonylamino}-3-(4-cyanophenyl)-propionate the synthesis is carried out analogously to the instructions in Example 1 (step g). The product is purified by crystallisation from ethanol/ethyl acetate. Yield: 70%; ¹H-NMR (250 MHz, DMSO-d6): δ [ppm]= 9.27, 9.24, 9.06, 9.03 (8H, 4 s, 2 C(=NH₂⁺)NH₂); 8.81 (1H, m, NHCO); 8.10–6.90 (11H, m, aryl-H); 4.71 (1H, m, NH—CH); 4.08 (2H, q, J=7.5 Hz, —O—CH₂); 3.72 (3H, s, aryl-N—CH₃); 3.50–3.18 (2H, m, aryl-CH₂); 3.24 (4H, s, aryl-CH₂—CH₂—); 1.16 (3H, t, J=7.5 Hz, —O—CH₂—CH₃).

EXAMPLE 29

Ethyl 2-{2-[2-(4-Amidinophenyl)-ethyl]-1-methyl-benzimidazol-5-yl-carbonyl-(methylamino)}-3-(4-amidinophenyl)-propionate-formate

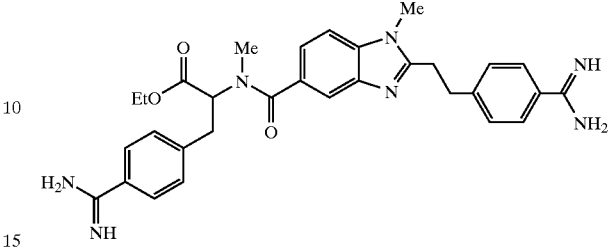

a) Ethyl 2-{2-[2-(4-Cyanophenyl)-ethyl]-1-methyl-benzimidazol-5-yl-carbonyl-(methylamino)}-3-(4-cyanophenyl)-propionate:

The synthesis is carried out starting from 7 mmol of 2-[2-(4-cyanophenyl)-ethyl]-1-methyl-benzimidazol-5-yl-carboxylic acid by reaction with ethyl 2-methylamino-3-(4-cyanophenyl)-propionate analogously to Example 1, step f. The product is chromatographed over silica gel (dichloromethane:methanol 20:1).

Yield: 61%; ¹H-NMR (250 MHz, CDCl₃): δ [ppm]= 7.83–7.23 (11H, m, aryl-H); 5.47 (1H, m, N—CH); 4.38 (2H, m, —O—CH₂—); 3.69 (3H, s, aryl-N—CH₃); 3.38, 3.22 (4H, 2 m, aryl-CH₂—CH₂—CH₂); 3.12 (2H, m, aryl-CH₂—CH—); 2.91 (3H, s, CO—N—CH₃); 1.35 (3H, t, —O—CH₂—CH₃).

b) Ethyl 2-{2-[2-(4-Amidinophenyl)-ethyl]-1-methyl-benzimidazol-5-yl-carbonyl-(methylamino)}-3-(4-amidinophenyl)-propionate:

Starting from 2.8 mmol of ethyl 2-{2-[2-(4-cyanophenyl)-ethyl]-1-methyl-benzimidazol-5-yl-carbonyl-(methylamino)}-3-(4-cyanophenyl)-propionate the synthesis is carried out analogously to the instructions in Example 1 (step g). The product is chromatographed over silica gel (acetonitrile:dichloromethane:formic acid:water 75:20:7.5:5). Yield: 36%; melting point: 230° C.; mass: calc.: [539]/[553], found: [M+H]⁺ 540, [M+H]⁺ 554; ¹H-NMR (250 MHz, DMSO-d6): δ [ppm]=8.17 (1H, s, HCOOH); 8.03–6.94 (11H, m, aryl-H); 5.37 (1H, m, N—CH—); 4.35 (2H, m, —O—CH₂—); 3.90 (3H, s, aryl-N—CH₃); 3.52, 3.39 (4H, 2 m, aryl-CH₂—CH₂—); 2.87 (3H, s, CO—N—CH₃); 3.48 (2H, m, aryl-CH₂—CH—); 1.35 (3H, m, —O—CH₂—CH₃).

EXAMPLE 30

2-{2-[2-(4-Amidinophenyl)-ethyl]-1-methyl-benzimidazol-5-yl-carbonylamino}-3-(4-amidinophenyl)-propionic Acid-diformate

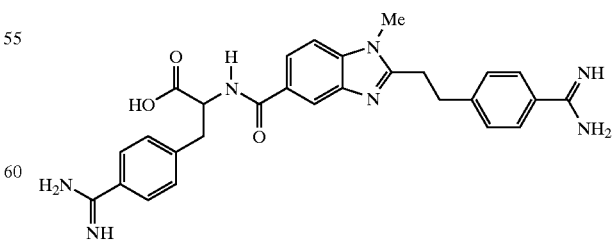

After saponification of ethyl 2-{2-[2-(4-amidinophenyl)-ethyl]-1-methyl-benzimidazol-5-yl-carbonylamino}-2-(4- amidinobenzyl)-propionate (Example 28; 1.55 g, 2.5 mmol) with excess aqueous sodium hydroxide solution (1N) in methanol in a ratio of 1:2 at ambient temperature over 16 h, a quantity of aqueous hydrochloric acid solution (1N) corresponding to the amount of sodium hydroxide added is put in and after the solvent has been distilled off in vacuo the residue is chromatographed over silica gel (acetonitrile:dichloromethane:formic acid:water 75:20:7.5:5).

Yield: 0.55 g (36%); melting point: 165° C.; mass: calc.: [511], found: [M+H]$^+$ 512; $^1$H-NMR (250 MHz, CD$_3$OD): δ [ppm]=8.07 (2H, s, HCOOH); 7.95–7.32 (11H, m, aryl-H); 4.90 (1H, m, NH—CH); 3.69 (3H, s, aryl-N—CH$_3$); 3.55–3.12 (6H, m, aryl-CH$_2$—CH$_2$, aryl-CH$_2$).

EXAMPLE 31

2-{2-[2-(4-Amidinophenyl)-ethyl]-1-methyl-benzimidazol-5-yl-carbonyl-methylamino}-3-(4-amidinophenyl)-propionic Acid-formate

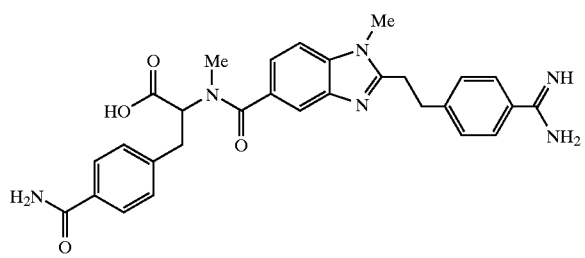

The reaction takes place analogously to the procedure described in Example 30 starting from ethyl 2-{2-[2-(4-amidinophenyl)-ethyl]-1-methyl-benzimidazol-5-yl-carbonyl-(methylamino)}-3-(4-amidinophenyl)-propionate (Example 29, 1.7 mmol). The product is obtained by crystallisation from dichloromethane/methanol. Yield: >90%; melting point: 255° C.; mass: calc.: [525], found: [M+H]$^+$ 526; $^1$H-NMR (250 MHz, DMSO-d6): δ [ppm]=10.20 (1H, s, COOH); 8.61 (1H, s, HCOOH); 8.09–6.77 (17H, m, 2 C(=NH)NH$_2$, aryl-H); 5.37 (1H, m, N—CH—); 3.78 (3H, s, aryl-N—CH$_3$); 3.33 (4H, s, aryl-CH$_2$—CH$_2$—); 2.98 (3H, s, CO—N—CH$_3$).

EXAMPLE 32

2-{2-[2-(4-Amidinophenyl)-ethyl]-1-methyl-benzimidazol-5-yl-carboxylic Acid-[N-(4-amidinobenzyl)-N-carboxymethyl-amide]-diacetate

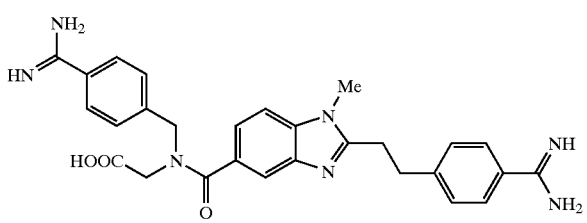

The reaction takes place analogously to the procedure described in Example 30 starting from the corresponding ethyl ester (4.4 mmol).

Yield. 48%; mass: calc. [511], found: [M+H]$^+$ 512, [M+2H]$^{2+}$ 256; $^1$H-NMR (250 MHz, DMSO-d6/CD$_3$OD): δ [ppm]=8.17–7.44 (11H, m, aryl-H); 4.65 (2H, s, N—CH$_2$); 4.09 (2H, s, N—CH$_2$—C=O); 3.82 (3H, s, aryl-N—CH$_3$); 3.57, 3.32 (4H, 2 m, aryl-CH$_2$—CH$_2$—); 1.86 (6H, s, CH$_3$—COO).

EXAMPLE 33

2-{2-[4-(Amino-hydroximino-methyl)phenyl]-ethyl}-1-methyl-benzimidazol-5-yl-carboxylic Acid-N-[2-(N',N'-dimethylamino)-ethyl]-N-methyl-amide

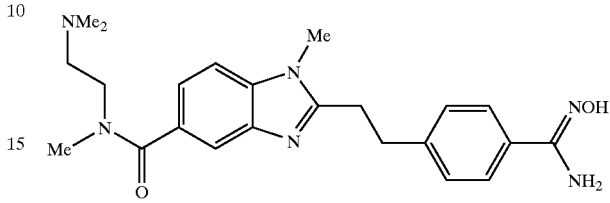

1.0 g (2.8 mmol) of 2-[2-(4-cyanophenyl)-ethyl]-1-methyl-benzimidazol-5-yl-carboxylic acid-[(N',N'-dimethylaminoethyl)-N-methyl-amide] (obtainable according to Example 3, step a), NH$_2$OH.HCl (0.83 g) and Na$_2$CO$_3$ (0.65 g) in 50 mL methanol are refluxed for 3 h. More NH$_2$OH.HCl (0.4 g) and Na$_2$CO$_3$.(0.3 g) are added. After 1 h refluxing the MeOH is distilled off, the residue is mixed to a slurry in water, filtered, washed with water and dried.

Yield: 59%. $^1$H-NMR (250 MHz, DMSO-d6): δ [ppm]= 9.58 (1H, s, OH); 7.56–7.18 (7H, m, aryl-H); 5.77 (2H, s, NH$_2$); 3.72 (3H, s, aryl-N—CH$_3$); 3.18 (6H, m, aryl-CH$_2$—CH$_2$—; N—CH$_2$—); 2.98 (3H, s, CO—N—CH$_3$); 2.43 (2H, m, Me$_2$-N—CH$_2$—); 2.16, 2.00 (6H, 2 s, N—(CH$_3$)$_2$);

EXAMPLE 34

2-{2-[2-(4-(Amidinophenyl)-ethyl]-1-methyl-benzimidazol-5-yl-carbonylamino}-6-acetylamino-hexanoic Acid-formate

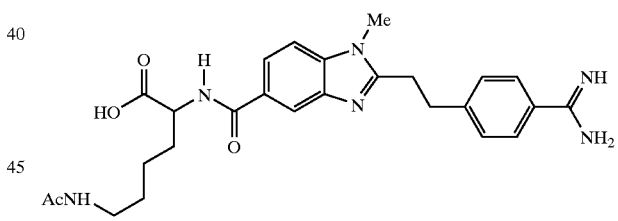

a) Benzyl 2-{2-[2-(4-Cyanophenyl)-ethyl]-1-methyl-benzimidazol-5-yl-carbonylamino}-6-benzyloxycarbonyl-amino-hexanoate:

The synthesis is carried out starting from 5 mmol of 2-[2-(4-cyanophenyl)-ethyl]-1-methyl-benzimidazol-5-yl-carboxylic acid by reaction with benzyl 2-amino-6-benzyloxycarbonyl-amino-hexanoate analogously to Example 1, step f. The product is chromatographed over silica gel (dichloromethane:methanol 50:1).

Yield: 66%;

b) Benzyl 2-{2-[2-(4-(Amino-hydroximino-methyl)-phenyl)-ethyl]-1-methyl-benzimidazol-5-yl-carbonylamino}-6-benzyloxycarbonylamino-hexanoate:

Starting from 3 mmol of benzyl 2-{2-[2-(4-cyanophenyl)-ethyl]-1-methyl-benzimidazol-5-yl-carbonylamino}-6-benzyloxycarbonyl-amino-hexanoate the synthesis is carried out analogously to the instructions in Example 33. Potassium tert. butoxide is used as the base. The product is chromatographed over silica gel (dichloromethane:methanol 20:1). Yield: 75%;

c) 2-{2-[2-(4-(Amidinophenyl)-ethyl]-1-methyl-benzimidazol-5-yl-carbonylamino}-6-acetylamino-hexanoic Acid-formate:

1.4 g (2 mmol) of benzyl 2-{2-[2-(4-(amino-hydroximino-methyl)-phenyl)-ethyl]-1-methyl-benzimidazol-5-yl-carbonylamino}-6-benzyloxycarbonylamino-hexanoate are taken up in 10 mL acetic acid and 2 mL acetanhydride and kept at ambient temperature for 16 h. The solvent is distilled off in vacuo and the residue remaining is hydrogenated in 40 mL methanol in the presence of 5% Pd/C (0.6 g) at normal pressure. The catalyst is filtered off, the filtrate is evaporated down and the residue is chromatographed over silica gel (acetonitrile:dichloromethane:formic acid:water 75:20:7.5:5).

Yield: 0.4 g (35%); melting point: 158° C.; mass: calc.: [492], found: [M+H]$^+$ 493; $^1$H-NMR (250 MHz, CD$_3$OD): δ [ppm]=8.27 (1H, s, HCOOH); 8.01–7.55 (7H, m, aryl-H); 4.66 (1H, m, N—CH—); 3.78 (3H, s, aryl-N—CH$_3$); 3.42–3.26 (4H, s, aryl-CH$_2$—CH$_2$—); 3.23 (2H, m, —N—CH$_2$—); 2.02–1.58 (6H, m, —N—CH$_2$—CH$_2$—CH$_2$—CH$_2$—); 1.92 (3H, s, NH—CO—CH$_3$).

EXAMPLE 35

2-{2-[2-(4-(Amidinophenyl)-ethyl]-1-methyl-benzimidazol-5-yl-carbonylamino}-2-(4-acetylaminomethyl-phenyl)-propionic Acid

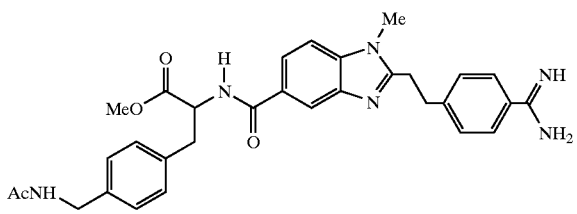

a) Methyl 2-{2-[2-(4-(Cyanophenyl)-ethyl]-1-methyl-benzimidazol-5-yl-carbonylamino}-3-[4-benzyloxycarbonylaminomethyl-phenyl]-propionate:

The synthesis is carried out starting from 1.2 mmol of 2-[2-(4-cyanophenyl)-ethyl]-1-methyl-benzimidazol-5-yl-carboxylic acid by reaction with methyl 2-amino-3-[4-benzyloxycarbonylaminomethyl-phenyl]-propionate analogously to Example 1, step f. The product is chromatographed over silica gel (dichloromethane:methanol 50:1). Yield: 90%;

b) Methyl 2-{2-[2-(4-(Amino-hydroximino-methyl)-phenyl)-ethyl]-1-methyl-benzimidazol-5-yl-carbonylamino}-3-[4-benzyloxycarbonylaminomethyl-phenyl]-propionate:

Starting from 1 mmol of methyl 2-{2-[2-(4-(cyanophenyl)-ethyl]-1-methyl-benzimidazol-5-yl-carbonylamino}-3-[4-benzyloxycarbonylaminomethyl-phenyl]-propionate the synthesis is carried out analogously to the instructions in Example 33. Potassium tert. butoxide is used as the base. The product is chromatographed over silica gel (dichloromethane:methanol 20:1). Yield: 74%; $^1$H-NMR (250 MHz, DMSO-d6): δ [ppm]=9.57 (1H, s, OH); 8.79 (1H, d, J=7.5 Hz, NH—CH—); 7.79 (1H, t, J=6.5 Hz, NH—CH$_2$—); 8.18–7.13 (16H, m, aryl-H); 5.76 (2H, s, NH$_2$); 5.04 (2H, s, O—CH$_2$—); 4.65 (1H, m, NH—CH—); 4.17 (1H, d, J=6.5 Hz, NH—CH$_2$—); 3.71 (3H, s, —OCH$_3$); 3.66 (3H, s, aryl-N—CH$_3$); 3.39 (4H, m, aryl-CH$_2$—CH$_2$—); 3.18 (2H, m, aryl-CH$_2$—).

c) 2-{2-[2-(4-(Amidinophenyl)-ethyl]-1-methyl-benzimidazol-5-yl-carbonylamino}-2-(4-acetylaminomethyl-phenyl)-propionic Acid:

Starting from 0.7 mmol of methyl 2-{2-[2-(4-(amino-hydroximino-methyl)-phenyl)-ethyl]-1-methyl-benzimidazol-5-yl-carbonylamino{3-[4-benzyloxycarbonylaminomethyl-phenyl]-propionate the synthesis is carried out analogously to the instructions in Example 34 (last step).

mass: calc.: [492], found: [M+H]$^+$ 493; $^1$H-NMR (250 MHz, DMSO-d6): δ [ppm]=10.1 (3H, broad, C(=NH)NH$_2$); 8.89 (1H, d, J=7.6 Hz, NH—CH); 8.40 (1H, t, J=5.8 Hz, NH—CH$_2$); 8.23–7.14 (11H, m, aryl-H); 4.69 (1H, m, CH—CH$_2$—); 4.24 (2H, d, J=5.8 Hz, NH—CH$_2$); 3.78 (3H, s, OCH$_3$); 3.69 (3H, s, aryl-N—CH$_3$); 3.29 (4H, s, aryl-CH$_2$—CH$_2$—); 3.15 (2H, m, CH—CH$_2$—); 1.86 (3H, s, CO CH$_3$).

EXAMPLE 36

2-[2-(4-Amidinophenyl)-ethyl]-1-methyl-benzimidazol-5-yl-carboxylic Acid-[N-(2-(N'-benzylamino)-ethyl)-N-cyclohexyl-amide]-dihydrochloride:

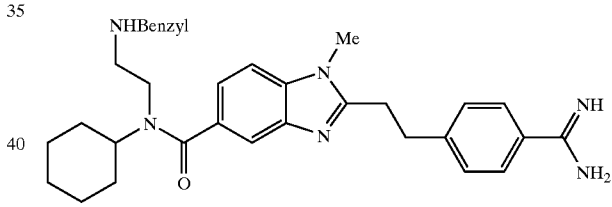

4.0 g (5.7 mmol) of 2-[2-(4-amidinophenyl)-ethyl]-1-methyl-benzimidazol-5-yl-carboxyl acid-N-(2-(N',N'-dibenzylamino)-ethyl)-N-cyclohexyl-amide (Example 2) are hydrogenated in 100 mL methanol in the presence of 5% Pd/C at normal pressure and 40–60° C. The catalyst is filtered off, the filtrate is evaporated down and the residue is chromatographed over silica gel (dichloromethane/methanol 9:1–7:3).

Yield: 0.6 g (17%). mass: calc.: [536], found: [M+H]$^+$ 537, [M+2H]$^{2+}$ 269; $^1$H-NMR (250 MHz, DMSO-d6): δ [ppm]=9.34, 9.80 (4H, 2 s, C(=NH$_2^+$)NH$_2$); 7.84–7.10 (12H, m, aryl-H); 4.14, 3.09 (4H, 2 m, N—CH$_2$—CH$_2$—N); 3.76 (3H, s, aryl-N—CH$_3$); 3.70 (2H, s, N—CH$_2$-Ph); 3.47 (1H, m, N-cyclohexyl-H); 3.26 (4H, s, aryl-CH$_2$—CH$_2$—); 1.92–0.54 (10H, m, cyclohexyl).

The following was also obtained from the same reaction mixture:

EXAMPLE 37

2-[2-(4-Amidinophenyl)-ethyl]-1-methyl-benzimidazol-5-yl-carboxylic Acid-[N-(2-amino-ethyl)-N-cyclohexyl-amide]-dihydrochloride:

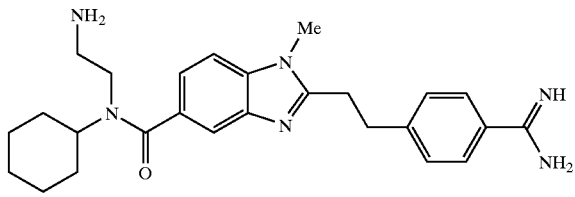

Yield: 0.4 g (13%); mass: calc.: [446], found: [M+H]447, [M+2H]$^{2+}$ 224; $^1$H-NMR (250 MHz, DMSO-d6): δ [ppm]= 8.56 (4H, broad, C(=NH$_2$$^+$)NH$_2$); 7.66–6.98 (7H, m, aryl-H); 3.57 (3H, s, aryl-N—CH$_3$); 3.45, 2.78 (4H, 2 m, N—CH$_2$—CH$_2$—N); 3.35 (1H, m, N-cyclohexyl-H); 3.07 (4H, s, aryl-CH$_2$—CH$_2$—); 1.49 (2H, s, NH$_2$); 1.65–0.55 (10H, m, cyclohexyl).

EXAMPLE 38

2-[2-(4-Amidinophenyl)-ethyl]-1-methyl-benzimidazol-5-yl-carboxylic Acid-N-(2-phenylamino-ethyl)-amide-dihydrochloride

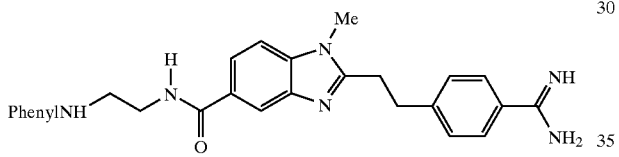

Using a procedure analogous to Example 36, starting from 2-[2-(4-amidinophenyl)-ethyl]-1-methyl-benzimidazol-5-yl-carboxylic acid-[N-(2-(N',N'-dibenzylamino)-ethyl)-N-phenyl-amide] (Example 19), Example 38 was isolated.

Yield: 7%; mass: calc. [440], found: [M+H]$^+$ 441, [M+2H]$^{2+}$ 221; $^1$H-NMR (250 MHz, DMSO-d6): δ [ppm]= 8.20–6.57 (12H, m, aryl-H); 3.78 (3H, s, aryl-N—CH$_3$); 3.51, 3.26 (4H, 2 m, N—CH$_2$—CH$_2$—N); 3.32 (4H, s, aryl-CH$_2$—CH$_2$—).

EXAMPLE 39

2-[2-(4-aminomethyl-phenyl)-ethyl]-1-methyl-benzimidazol-5-yl-carboxylic Acid-N-(2-phenylamino-ethyl)-amide-trihydrochloride

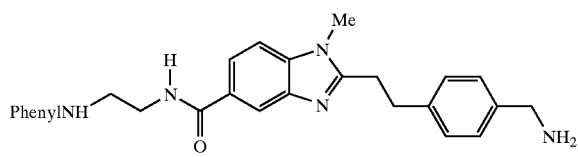

a) 2-[2-(4-cyanophenyl)-ethyl]-1-methyl-benzimidazol-5-yl-carboxylic Acid-N-(2-phenylamino-ethyl)-amide:

The synthesis is carried out starting from 8.2 mmol of 2-[2-(4-cyanophenyl)-ethyl]-1-methyl-benzimidazol-5-yl-carboxylic acid by reaction with N-phenylethylenediamine analogously to Example 1, step f. The product is obtained by crystallisation from ethyl acetate/diethylether and optionally recrystallised from acetonitrile. Yield: 86%; melting point: 161–163° C.; $^1$H-NMR (250 MHz, CDCl$_3$): δ [ppm]= 8.24–6–67 (12H, m, aryl-H); 4.21 (1H, broad, NHCO); 3.79, 3.36 (4H, 2 m, N—CH$_2$-CH$_2$—N); 3.66 (3H, s, aryl-N—CH$_3$); 3.66, 3.21 (4H, 2 m, aryl-CH$_2$—CH$_2$—); 1.89 (1H, broad, Ph-<u>NH</u>).

b) 2-[2-(4-aminomethyl-phenyl)-ethyl]-1-methyl-benzimidazol-5-yl-carboxylic acid-[N-(2-phenylamino-ethyl)-amide]: 2.0 g (4.7 mmol) of 2-[2-(4-cyanophenyl)-ethyl]-1-methyl-benzimidazol-5-yl-carboxylic acid-N-(2-phenylamino-ethyl)-amide are hydrogenated in 100 mL methanol in the presence of about 2.5 g methanol-moistened Raney nickel at ambient temperature under normal pressure. The catalyst is filtered off, washed with methanol and the solvent is distilled off in vacuo. The residue is chromatographed over silica gel (dichloromethane:methanol 85:1), the trihydrochloride is crystallised from ethanol/acetone with conc. hydrochloric acid.

Yield: 1.5 g (59%); melting point: >220° C.; mass: calc.: [427], found: [M+H]$^+$ 428; $^1$H-NMR (250 MHz, DMSO-d6): δ [ppm]=8.51 (1H, t, J=5.5 Hz, NHCO); 8.15–6.44 (12H, m, aryl-H); 5.71 (1H, t, J=5.5 Hz, —<u>NH</u>-Ph); 3.68 (3H, s, aryl-N—CH$_3$); 3.65 (2H, s, —N—<u>CH</u>$_2$-Ph); 3.44, 3.12 (4H, 2 m, N—CH$_2$—CH$_2$—N); 3.22, 3.16 (4H, 2 m, aryl-CH$_2$—CH$_2$—); 3.35 (2H, broad, NH$_2$).

EXAMPLE 40

2-[2-(4-Aminomethyl-phenyl)-ethyl]-1-methyl-benzimidazol-5-yl-carboxylic Acid-N-(3,3-diphenylpropyl)-amide-dihydrochloride:

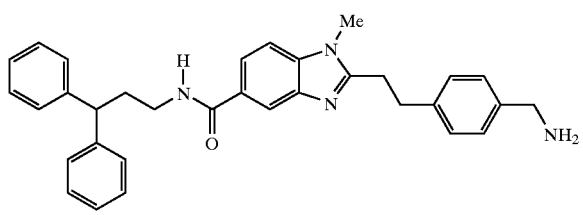

Starting from 2.8 mmol of 2-[2-(4-cyanophenyl)-ethyl]-1-methyl-benzimidazol-5-yl-carboxylic acid-N-(3,3-diphenylpropyl)-amide (Example 13, step b) the synthesis is carried out in accordance with the method according to Example 39, step b. The reaction is carried out in the presence of 8 g of ammonia at 5 bar and 60° C. The residue is chromatographed over silica gel (dichloromethane:methanol 95:5–9:1).

Yield: 23%; melting point: 140° C.; mass: calc.: [502], found: [M+H]$^+$ 503; $^1$H-NMR (250 MHz, DMSO-d6): δ [ppm]=8.99 (1H, t, J=5.4 Hz, NHCO); 8.67 (3H, broad NH$_3$$^+$); 8.50–7.29 (17H, m, aryl-H); 4.29, 4.15, 2.52 (5H, 3 m, N—CH$_2$—CH$_2$—CH); 4.06 (2H, s, —<u>CH</u>$_2$—NH$_2$); 3.68 (3H, s, aryl-N—CH$_3$); 3.63, 3.39 (4H, 2 m, aryl-CH$_2$—CH$_2$).

EXAMPLE 41

2-[2-(4-Aminomethyl-phenyl)-ethyl]-1-methyl-benzimidazol-5-yl-carboxylic Acid-[N'-(2-methyl-phenyl)-diazepide]-hydrochloride

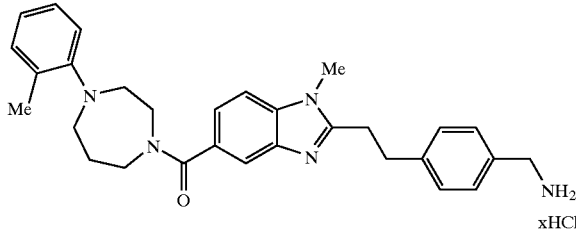

xHCl

Starting from 2.5 mmol of 2-[2-(4-cyanophenyl)-ethyl]-1-methyl-benzimidazol-5-yl-carboxylic acid-[N'-(2-methyl-phenyl)-diazepide] (Example 15, step b) the synthesis is carried out in accordance with the method according to Example 39, step b. The reaction is carried out in the presence of 8 g of ammonia at 5 bar and 60° C. The residue is chromatographed over silica gel (dichloromethane:methanol 9:1).

Yield: 48%; mass: calc.: [481], found: [M+H]$^+$ 482; $^1$H-NMR (250 MHz, CD$_3$OD): δ [ppm]=8.13–7.24 (1H, m, aryl-H); 4.10 (2H, s, —CH$_2$—NH$_2$); 3.95 (3H, s, aryl-N—CH$_3$); 2.63 (3H, s, aryl-CH$_3$); 4.06–2.49 (10H, m, diazacycloheptanyl).

EXAMPLE 42

2-[2-(4-aminomethyl-phenyl)-ethyl]-1-methyl-benzimidazol-5-yl-carboxylic Acid-N-(4-aminomethyl-benzyl)-N-(3-phenylpropyl)-amide-dihydrochloride:

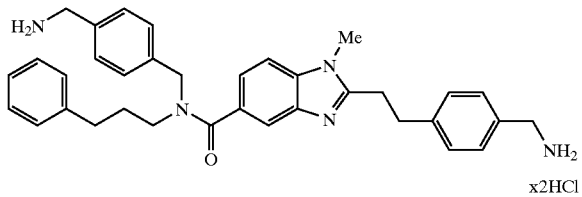

x2HCl

Starting from 7.8 mmol of 2-[2-(4-cyanophenyl)-ethyl]-1-methyl-benzimidazol-5-yl-carboxylic acid-N-(4-cyanobenzyl)-N-(3-phenylpropyl)-amide (Example 12, step b) the synthesis is carried out in accordance with the method according to Example 39, step b.

The reaction is carried out in the presence of 8 g of ammonia at 5 bar and 60° C. The residue is chromatographed over silica gel (dichloromethane:methanol 95:5–85:15).

Yield: 42%; mass: calc.: [545], found: [M+H]$^+$ 546; $^1$H-NMR (250 MHz, DMSO-d6): δ [ppm]=8.76 (6H, s, 2—NH$_3^+$); 8.15–6.93 (16H, m, aryl-H); 4.68 (2H, s, N—CH$_2$-Ph); 4.08, 4.02 (4H, 2 s, CH$_2$—NH$_2$); 3.96 (3H, s, aryl-N—CH$_3$); 3.34 (4H, s, aryl-CH$_2$—CH$_2$—); 3.16–1.64 (6H, m, N—CH$_2$—CH$_2$—CH$_2$—).

EXAMPLE 43

2-[2-(4-Aminomethyl-phenyl)-ethyl]-1-methyl-benzimidazol-5-yl-carboxylic Acid-N-(4-aminomethylbenzyl)-N-(3,3-diphenylpropyl)-amide-dihydrochloride:

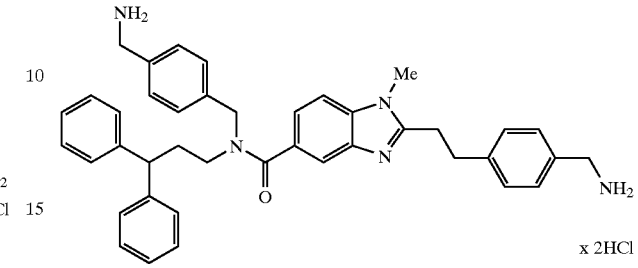

x 2HCl

Starting from 8.3 mmol of 2-[2-(4-cyanophenyl)-ethyl]-1-methyl-benzimidazol-5-yl-carboxylic acid-N-(4-cyanobenzyl)-N-(3,3-diphenylpropyl)-amide (Example 17, step b) the synthesis is carried out in accordance with the method according to Example 39, step b. The reaction is carried out in the presence of 10 g of ammonia at 5 bar and 60° C. The residue is chromatographed over silica gel (dichloromethane:methanol 9:1–4:1). Yield: 36%; melting point: 140° C.; mass: calc.: [621], found: [M+H]$^+$ 622, [M+2H]$^{2+}$ 312; $^1$H-NMR (250 MHz, DMSO-d6): δ [ppm]= 8.51 (6H, broad, —NH$_3^+$); 7.74–7.08 (21H, m, aryl-H); 4.66 (2H, s, N—CH$_2$—); 4.02, 4.00 (4H, 2 s, CH$_2$—NH$_2$); 3.84 (3H, s, aryl-N—CH$_3$); 3.84, 3.41, 2.24 (5H, 3 m, N—CH$_2$—CH$_2$—CH).

EXAMPLE 44

2-{2-[4-(Amino-hydroximino-methyl)phenyl]-ethyl}-1-methyl-benzimidazol-5-yl-carboxylic acid-[N'-(2-methylphenyl)-piperazide]

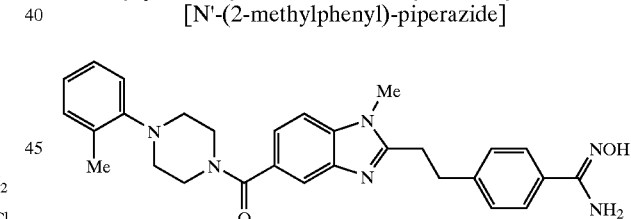

a) 2-[2-(4-Cyanophenyl)-ethyl]-1-methyl-benzimidazol-5-yl-carboxylic Acid-[N'-(2-methyl-phenyl)-piperazide]:

The synthesis is carried out starting from 7.5 mmol of 2-[2-(4-cyanophenyl)-ethyl]-1-methyl-benzimidazol-5-yl-carboxylic acid chloride by reaction with N-(2-methylphenyl)piperazine analogously to Example 1, step f. The product is chromatographed over silica gel (dichloromethane:methanol 50:1). Yield: 58%;

b) 2-{2-[4-(amino-hydroximino-methyl)phenyl]-ethyl}-1-methyl-benzimidazol-5-yl-carboxylic acid-[N'-(2-methylphenyl)-piperazide]:

Starting from 5.4 mmol of 2-[2-(4-cyanophenyl)-ethyl]-1-methyl-benzimidazol-5-yl-carboxylic acid-[N'-(2-methyl-phenyl)-piperazide] the synthesis is carried out analogously to the instructions in Example 33. Potassium tert. butoxide is used as the base. The product is chromatographed over silica gel (dichloromethane:methanol 20:1). mass: calc.: [496], found: [M+H]+ 497; 1H-NMR (250 MHz, DMSO-d6): δ [ppm]=9.59 (1H, s, OH); 7.66–6.90 (11H, m, aryl-H); 5.76 (2H, s, —NH2); 3.71 (3H, s, N—CH3); 3.67 (4H, m —CH2—CH2-Ph); 3.17, 2.84 (8H, 2 m, piperazinyl); 2.26 (3H, s, aryl-N—CH3).

EXAMPLE 45

2-{2-[4-(Amino-hydroximino-methyl)phenyl]-ethyl}-1-methyl-benzimidazol-5-yl-carboxylic Acid-[N'-(3-methylphenyl)-piperazide]

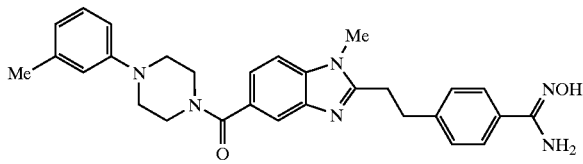

a) 2-[2-(4-Cyanophenyl)-ethyl]-1-methyl-benzimidazol-5-yl-carboxylic Acid-[N'-(3-methyl-phenyl)-piperazide]:

The synthesis is carried out starting from 7.5 mmol of 2-[2-(4-cyanophenyl)-ethyl]-1-methyl-benzimidazol-5-yl-carboxylic acid chloride by reaction with N-(3-methylphenyl)piperazine analogously to Example 1, step f. The product is chromatographed over silica gel (dichloromethane:methanol 50: 1). Yield: 88%;

b) 2-{2-[4-(Amino-hydroximino-methyl)phenyl]-ethyl}-1-methyl-benzimidazol-5-yl-carboxylic Acid-[N'-(3-methylphenyl)-piperazide]:

Starting from 6.4 mmol of 2-[2-(4-cyanophenyl)-ethyl]-1-methyl-benzimidazol-5-yl-carboxylic acid-[N'-(3-methyl-phenyl)-piperazide] the synthesis is carried out analogously to the instructions in Example 33. Potassium tert. butoxide is used as the base. The product is chromatographed over silica gel (dichloromethane:methanol 20:1). mass: : calc.: [496], found: [M+H]+ 497; 1H-NMR (250 MHz, DMSO-d6): δ [ppm]=9.56 (1H, s, OH); 7.66–6.90 (11H, m, aryl-H); 5.76 (2H, s, NH2); 3.72 (3H, s, N—CH3); 3.64 (4H, m, —CH2—CH2-Ph); 3.17 (8H, m, piperazinyl); 2.25 (3H, s, aryl-N—CH3).

EXAMPLE 46

2-{2-[4-(Amino-hydroximino-methyl)phenyl]-ethyl}-1-methyl-benzimidazol-5-yl-carboxylic Acid-(N'-benzyl-piperazide)

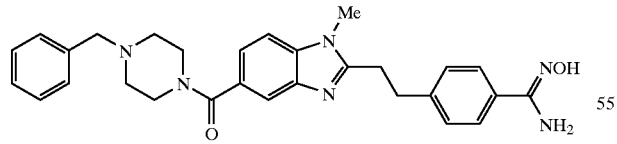

a) 2-[2-(4-Cyanophenyl)-ethyl]-1-methyl-benzimidazol-5-yl-carboxylic Acid-(N'-benzyl-piperazide):

The synthesis is carried out starting from 7.5 mmol of 2-[2-(4-cyanophenyl)-ethyl]-1-methyl-benzimidazol-5-yl-carboxylic acid chloride by reaction with N-benzylpiperazine analogously to Example 1, step f. The product is chromatographed over silica gel (dichloromnethane:methanol 50:1). Yield: 91%;

b) 2-{2-[4-(Amino-hydroximino-methyl)phenyl]-ethyl }-1-methyl-benzimidazol-5-yl-carboxylic Acid-(N'-benzyl-piperazide):

Starting from 6.6 mmol of 2-[2-(4-cyanophenyl)-ethyl]-1-methyl-benzimidazol-5-yl-carboxylic acid-(N'-benzyl-piperazide) the synthesis is carried out analogously to the instructions in Example 33. Potassium tert. butoxide is used as the base. The product is chromatographed over silica gel (dichloromethane:methanol 20:1).

mass: calc.: [496], found: [M+H]+ 497, [M+2H]2+ 249; 1H-NMR (250 MHz, DMSO-d6): δ [ppm]=9.56 (1H, s, OH); 7.62–7.16 (12H, m, aryl-H); 5.76 (2H, s, NH2); 3.70 (3H, s, N—CH3); 3.50 (2H, s, N—CH2-Ph); 3.39 (4H, m, —CH2—CH2-Ph); 3.16, 2.39 (8H, 2 m, piperazinyl).

The following compounds were also obtained analogously to the processes described hereinbefore:

EXAMPLE 47
2-[2-(4-Amidinophenyl)-ethyl]-1-methyl-benzimidazol-5-yl-carboxylic Acid-[N'-(3-methylphenyl)-piperazide]

EXAMPLE 48
2-[2-(4-Amidinophenyl)-ethyl]-1-methyl-benzimidazol-5-yl-carboxylic Acid-[N'-(3-ethoxyphenyl)-piperazide]

EXAMPLE 49
2-[2-(4-Amidinophenyl)-ethyl]-1-methyl-benzimidazol-5-yl-carboxylic Acid-[N '-(3-isopropyloxyphenyl)-piperazide]

EXAMPLE 50
2-[2-(4-Amidinophenyl)-ethyl]-1-methyl-benzimidazol-5-yl-carboxylic Acid-[N'-(cyclopentyl)-piperazide]

EXAMPLE 51
2-[2-(4-Amidinophenyl)-ethyl]-1-methyl-benzimidazol-5-yl-carboxylic Acid-[N'-(2-methylphenyl)-piperazide]

EXAMPLE 52
2-[2-(4-Amidinophenyl)-ethyl]-1-methyl-benzimidazol-5-yl-carboxylic Acid-[N'-(2-pyridyl)-piperazide]

EXAMPLE 53
2-[2-(4-Amidinophenyl)-ethyl]-1-methyl-benzimidazol-5-yl-carboxylic Acid-[N'-(2-methoxyphenyl)-piperazide]

EXAMPLE 54
2-[2-(4-Amidinophenyl)-ethyl]-1-methyl-benzimidazol-5-yl-carboxylic Acid-[N'-(2-ethoxyphenyl)-piperazide]

EXAMPLE 55
2-[2-(4-Amidinophenyl)-ethyl]-1-methyl-benzimidazol-5-yl-carboxylic Acid-[N'-benzyl-piperazide]

EXAMPLE 56
2-{2-[4-(Amino-methoxycarbonylimino-methyl)phenyl]-ethyl}-1-methyl-benzimidazol-5-yl-carboxylic Acid-N-phenyl-N-[3-amino-3-methoxycarbonylimino-propyl]-amide

EXAMPLE 57
2-(2-[4-(Amino-hydroximino-methyl)phenyl]-ethyl}-1-methyl-benzimidazol-5-yl-carboxylic Acid-[N '-(3-hydroxyphenyl)-piperazide]

EXAMPLE 58
2-{2-[4-(Amino-methoxycarbonylimino-methyl)phenyl]-ethyl)}-1-methyl-benzimidazol-5-yl-carboxylic Acid-N-(2-phenylethyl)-N-[3-amino-3-methoxycarbonylimino-propyl]-amide

EXAMPLE 59
2-{2-[4-(Amino-hydroximino-methyl)phenyl]-ethyl}-1-methyl-benzimidazol-5-yl-carboxylic acid-[N'-(2-pyridyl)-piperazide]

EXAMPLE 60

2-{2-[4-(Amino-hydroximino-methyl)phenyl]-ethyl}-1-methyl-benzimidazol-5-yl-carboxylic Acid-[N'-(cyclohexyl)-piperazide]

EXAMPLE 61

2-{2-[4-(Amino-hydroximino-methyl)phenyl]-ethyl}-1-methyl-benzimidazol-5-yl-carboxylic Acid-[N'-(cyclopentyl)-piperazide]

EXAMPLE 62

2-{2-[4-(Amino-hydroximino-methyl)phenyl]-ethyl}-1-methyl-benzimidazol-5-yl-carboxylic Acid-[N'-(2-ethoxy-phenyl)-piperazide]

EXAMPLE 63

2-{2-[4-(Amino-hydroximino-methyl)phenyl]-ethyl}-1-methyl-benzimidazol-5-yl-carboxylic Acid-[N'-(3-methoxy-phenyl)-piperazide]

EXAMPLE 64

2-{2-[4-(Amino-hydroximino-methyl)phenyl]-ethyl}-1-methyl-benzimidazol-5-yl-carboxylic Acid-[N'-(3-isopropyloxy-phenyl)-piperazide]

EXAMPLE 65

2-{2-[4-(Amino-hydroximino-methyl)phenyl]-ethyl}-1-methyl-benzimidazol-5-yl-carboxylic Acid-[N'-(3-ethoxy-phenyl)-piperazide]

EXAMPLE 66

2-{2-[4-(Amino-hydroximino-methyl)phenyl]-ethyl}-1-methyl-benzimidazol-5-yl-carboxylic Acid-N-phenyl-N-[3-amino-3-hydroxyimino-propyl]-amide

EXAMPLE 67

2-{2-[4-(Amino-hydroximino-methyl)phenyl]-ethyl}-1-methyl-benzimidazol-5-yl-carboxylic Acid-N-(2-phenylethyl)-N-[3-amino-3-hydroxyimino-propyl]-amide

EXAMPLE 68

2-{2-[4-(Amino-hydroximino-methyl)phenyl]-ethyl}-1-methyl-benzimidazol-5-yl-carboxylic Acid-[N'-(cyclohexyl)-piperazide]

General operating method for synthesising compounds of general formula (I) on the solid phase:
a) Reductive Amination:

A suspension of 0.06 mmol of the amine coupled to the trityl resin and 300 µm of a 1:1 (v/v) solution of tetramethyl orthoformate/dichloromethane is combined with 500 µl of a 0.12 M solution of the aldehydes $R^4$—CHO in tetramethyl orthoformate/dichloromethane (1:1 v/v) and shaken for 2 h at ambient temperature. Then the resin is filtered off and washed twice each with 1.5 ml of dichloromethane, dimethylformamide and dichloromethane.

The resin is suspended in 300 µl dichloromethane, combined with 1200 µl of a 0.167 M solution of sodium triacetoxyborohydride in dichloromethane and shaken for 12 hat ambient temperature. The resin is filtered off and washed twice each with 1.5 ml water, dimethylformiamide/water 7:3 (v/v), dimethylformamide/water/acetic acid 90:10:5 (v/v/v), dimethylformamide/water 9:1 (v/v), dimethylformamide, dichloromethane.

b) Acylation with 4-Chloro-3-nitro-benzoylchloride:

The resin, suspended in 500 µl diisopropylethylamine solution (20% in dichloromethane), is combined with 1000 µl of a 0.2 M solution of 4-chloro-3-nitro-benzoylchloride in dichloromethane and shaken for 12 h at ambient temperature. It is then filtered off and washed 3 times with 1.5 ml dichloromethane and 1-methyl-2-pyrrolidone.

c) Nucleophilic Substitution:

The resin, suspended in 500 µl diisopropylethylamine solution in 1-methyl-2-pyrrolidone (20% v/v). is combined with 1000 µl of a 0.1 M solution of an amine $R^1$—$NH_2$ in 1-methyl-2-pyrrolidone and heated to 85° C. for 12 h. After cooling to ambient temperature the resin is filtered off and washed 3 times with 1.5 ml of 1-methyl-2-pyrrolidone and dimethylformamide.

d) Reduction of the Nitro Group:

The resin is suspended in 500 µl dimethylformamide, combined with 1000 µl 1.0 M $SnCl_2$ solution in dimethylformamide and shaken for 48 h at ambient temperature. Then the resin is filtered off and washed twice with 1.5 ml dimethylformamide, dioxane, methanol/$NH_4OH$ 98:2 (v/v), aqueous methanol (80%), methanol and tetrahydrofuran.

e) Oxidative Cyclisation to Obtain the Benzimidazole:

The resin is suspended in 500 µl of tetrahydrofuran, combined with 1000 µl of 0.1M solution of an aldehyde $R^2$—$C_6H_4$—$CH_2CH_2$—CHO solution in THF and shaken for 48 h at ambient temperature in oxygen from the air. Then the resin is filtered off and washed 5 times with 1.5 ml tetrahydrofuran, dichloromethane/methanol 95/5 and dichloromethane.

f) Cleaving the Product from the Resin:

The resin is shaken with 1000 µl of trifluoroacetic acid, 10% v/v in dichloromethane, for 1 h at ambient temperature and suction filtered. Then the resin remaining is again combined with 500 µl of trifluoroacetic acid, 10% v/v in dichloromethane, suction filtered, and the combined filtrates are evaporated down in vacuo. After the resin residue has been treated with 1000 µl of dichloromethane/methanol 95:5 the mixture is shaken for 1 h at ambient temperature and filtered off. The filtrates and the residues obtained are combined and evaporated to dryness in vacuo.

The Tables which follow list other compounds of general formula (I) synthesised according to the invention. These may be obtained both analogously to the preceding Examples 1–68 and also according to the solid phase synthesis method described above.

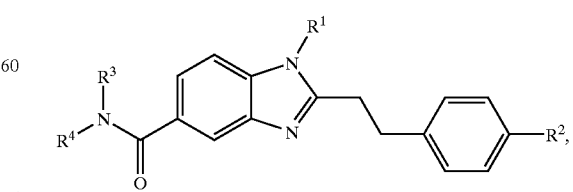

(I)

TABLE 1

Compounds of general formula (I) according to the invention wherein the following definitions apply:

—R²: —C(=NH)NH₂; —R³: 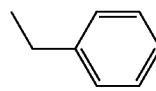 ; —R⁴: 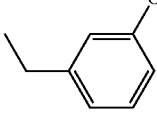

| Ex. | —R¹ | calc. [M] | found* | Found# | Chemical name |
|---|---|---|---|---|---|
| 69 | n-decyl- | 686 | — | 343 | 2-[2-(4-amidinophenyl)ethyl]-1-n-decyl-benzimidazol-5-yl-carboxylic acid-N-[4-(amino-methyl)-benzyl]-N-(3-methoxy-benzyl)-amide |
| 70 |  | 632 | 633 | 317 | 2-[2-(4-amidinophenyl)ethyl]-1-(3-ethoxy-propyl)-benzimidazol-5-yl-carboxylic acid-N-[4-(amino-methyl)-benzyl]-N-(3-methoxybenzyl)-amide |
| 71 |  | 715 | 716 | 358 | 2-[2-(4-amidinophenyl)ethyl]-1-(3-di-n-butylaminopropyl)-benzimidazol-5-yl-carboxylic acid-N-[4-(amino-methyl)-benzyl]-N-(3-methoxybenzyl)-amide |
| 72 | 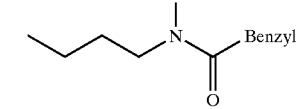 | 721 | — | — | 2-[2-(4-amidinophenyl)ethyl]-1-[3-(benzylcarbonylamino)-propyl]-benzimidazol-5-yl-carboxylic acid-N-[4-(amino-methyl)-benzyl]-N-(3-methoxybenzyl)-amide |
| 73 | 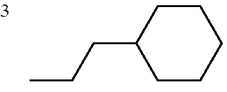 | 656 | 657 | 329 | 2-[2-(4-amidinophenyl)ethyl]-1-(2-cyclohexylethyl)-benzimidazol-5-yl-carboxylic acid-N-[4-(amino-methyl)-benzyl]-N-(3-methoxybenzyl)-amide |
| 74 | 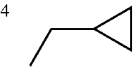 | 600 | 601 | — | 2-[2-(4-amidinophenyl)ethyl]-1-cyclopropylmethyl-benzimidazol-5-yl-carboxylic acid-N-[4-(amino-methyl)-benzyl]-N-(3-methoxybenzyl)-amide |
| 75 | 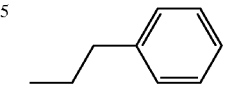 | 650 | — | 326 | 2-[2-(4-amidinophenyl)ethyl]-1-(2-phenyl-ethyl)-benzimidazol-5-yl-carboxylic acid-N-[4-(amino-methyl)-benzyl]-N-(3-methoxybenzyl)-amide |
| 76 | 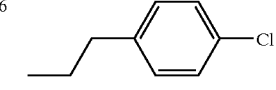 | 684 | — | — | 2-[2-(4-amidinophenyl)ethyl]-1-[2-(4-chlorophenyl)ethyl]-benzimidazol-5-yl-carboxylic acid-N-[4-(amino-methyl)-benzyl]-N-(3-methoxybenzyl)-amide |
| 77 | 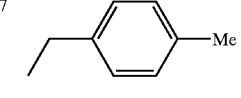 | 650 | — | 326 | 2-[2-(4-amidinophenyl)ethyl]-1-(4-methylbenzyl)-benzimidazol-5-yl-carboxylic acid-N-[4-(amino-methyl)-benzyl]-N-(3-methoxybenzyl)-amide |
| 78 | 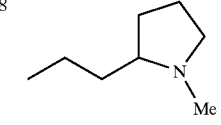 | 657 | 658 | 329 | 2-[2-(4-amidinophenyl)ethyl]-1-[2-(1-methylpyrrolidin-2-yl)-ethyl]-benzimidazol-5-yl-carboxylic acid-N-[4-(amino-methyl)-benzyl]-N-(3-methoxybenzyl)-amide |
| 79 | 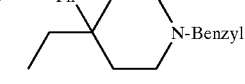 | 809 | — | — | 2-[2-(4-amidinophenyl)ethyl]-1-[(1-benzyl-4-phenyl-piperidin-4-yl)-methyl]-benzimidazol-5-yl-carboxylic acid-N-[4-(amino-methyl)-benzyl]-N-(3-methoxybenzyl)-amide |
| 80 | 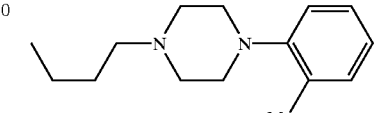 | 762 | 763 | 381 | 2-[2-(4-amidinophenyl)ethyl]-1-{3-[4-(2-methylphenyl)-piperazin-1-yl]-propyl}-benzimidazol-5-yl-carboxylic acid-N-[4-(amino-methyl)-benzyl]-N-(3-methoxybenzyl)-amide |

TABLE 1-continued

Compounds of general formula (I) according to the invention wherein the following definitions apply:

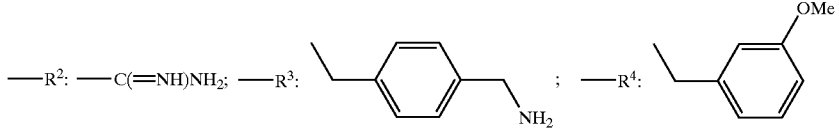

| Ex. | —R¹ | calc. [M] | found* | Found# | Chemical name |
|---|---|---|---|---|---|
| 81 | (propyl-morpholine) | 673 | — | — | 2-[2-(4-amidinophenyl)ethyl]-1-[3-(morpholin-4-yl)-propyl]-benzimidazol-5-yl-carboxylic acid-N-[4-(amino-methyl)-benzyl]-N-(3-methoxybenzyl)-amide |
| 82 | (tetrahydrofuran-2-ylmethyl) | 630 | 631 | — | 2-[2-(4-amidinophenyl)ethyl]-1-(tetrahydrofuran-2-yl-methyl)-benzimidazol-5-yl-carboxylic acid-N-[4-(amino-methyl)-benzyl]-N-(3-methoxybenzyl)-amide |
| 83 | (thiophen-2-ylmethyl) | 642 | — | — | 2-[2-(4-amidinophenyl)ethyl]-1-(2-thiophenyl-methyl)-benzimidazol-5-yl-carboxylic acid-N-[4-(amino-methyl)-benzyl]-N-(3-methoxybenzyl)-amide |
| 84 | (1,3-benzodioxol-5-ylmethyl) | 680 | 681 | 641 | 2-[2-(4-amidinophenyl)ethyl]-1-(1,3-benzodioxol-5-yl-methyl)-benzimidazol-5-yl-carboxylic acid-N-[4-(amino-methyl)-benzyl]-N-(3-methoxybenzyl)-amide |

*[M + H]⁺;
[M + 2H]²⁺

TABLE 2

Compounds of general formula (I) according to the invention wherein the following definitions apply:

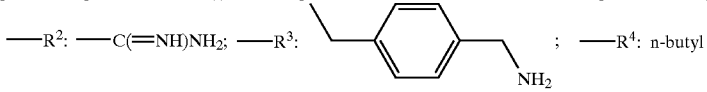

| Ex. | —R¹ | calc. [M] | found* | found# | Chemical name |
|---|---|---|---|---|---|
| 85 | n-decyl- | 622 | 623 | 311 | 2-[2-(4-amidinophenyl)ethyl]-1-n-decyl-benzimidazol-5-yl-carboxylic acid-N-[4-(amino-methyl)-benzyl]-N-n-butyl-amide |
| 86 | —(CH₂)₃—OEt | 568 | 569 | 276 | 2-[2-(4-amidinophenyl)ethyl]-1-(3-ethoxypropyl)-benzimidazol-5-yl-carboxylic acid-N-[4-(amino-methyl)-benzyl]-N-n-butyl-amide |
| 87 | —(CH₂)₃—N(n-Butyl)₂ | 651 | 652 | 326 | 2-[2-(4-amidinophenyl)ethyl]-1-(3-di-n-butylaminopropyl)-benzimidazol-5-yl-carboxylic acid-N-[4-(amino-methyl)-benzyl]-N-n-butyl-amide |
| 88 | —(CH₂)₃—NH—C(O)—Benzyl | 657 | — | — | 2-[2-(4-amidinophenyl)ethyl]-1-3-(benzylcarbonylamino)-propyl]-benzimidazol-5-yl-carboxylic acid-N-[4-(amino-methyl)-benzyl]-N-n-butyl-amide |
| 89 | —(CH₂)₂—cyclohexyl | 592 | — | — | 2-[2-(4-amidinophenyl)ethyl]-1-(2-cyclohexylethyl)-benzimidazol-5-yl-carboxylic acid-N-[4-(amino-methyl)-benzyl]-N-n-butyl-amide |

TABLE 2-continued

Compounds of general formula (I) according to the invention wherein the following definitions apply:

—R²: —C(=NH)NH₂; —R³: 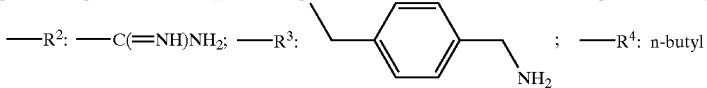 ; —R⁴: n-butyl

| Ex. | —R¹ | calc. [M] | found* | found# | Chemical name |
|---|---|---|---|---|---|
| 90 | cyclopropylmethyl | 536 | — | — | 2-[2-(4-amidinophenyl)ethyl]-1-cyclopropylmethyl-benzimidazol-5-yl-carboxylic acid-N-[4-(amino-methyl)-benzyl]-N-n-butyl-amide |
| 91 | phenylethyl | 586 | — | — | 2-[2-(4-amidinophenyl)ethyl]-1-(2-phenylethyl)-benzimidazol-5-yl-carboxylic acid-N-[4-(amino-methyl)-benzyl]-N-n-butyl-amide |
| 92 | 4-chlorophenylethyl | 620 | — | — | 2-[2-(4-amidinophenyl)ethyl]-1-[2-(4-chlorophenyl)ethyl]-benzimidazol-5-yl-carboxylic acid-N-[4-(amino-methyl)-benzyl]-N-n-butyl-amide |
| 93 | 4-methylbenzyl-ethyl | 586 | — | — | 2-[2-(4-amidinophenyl)ethyl]-1-(4-methylbenzyl)-benzimidazol-5-yl-carboxylic acid-N-[4-(amino-methyl)-benzyl]-N-n-butyl-amide |
| 94 | 1-methylpyrrolidin-2-yl-ethyl | 593 | 594 | — | 2-[2-(4-amidinophenyl)ethyl]-1-[2-(1-methylpyrrolidin-2-yl)-ethyl]-benzimidazol-5-yl-carboxylic acid-N-[4-(amino-methyl)-benzyl]-N-n-butyl-amide |
| 95 | 1-benzyl-4-phenyl-piperidin-4-yl-methyl | 745 | — | — | 2-[2-(4-amidinophenyl)ethyl]-1-[(1-benzyl-4-phenyl-piperidin-4-yl)-methyl]-benzimidazol-5-yl-carboxylic acid-N-[4-(amino-methyl)-benzyl]-N-n-butyl-amide |
| 96 | 3-[4-(2-methylphenyl)-piperazin-1-yl]-propyl | 698 | — | — | 2-[2-(4-amidinophenyl)ethyl]-1-{3-[4-(2-methylphenyl)-piperazin-1-yl]-propyl}-benzimidazol-5-yl-carboxylic acid-N-[4-(amino-methyl)-benzyl]-N-n-butyl-amide |
| 97 | 3-(morpholin-4-yl)-propyl | 609 | — | — | 2-[2-(4-amidinophenyl)ethyl]-1-[3-(morpholin-4-yl)-propyl]-benzimidazol-5-yl-carboxylic acid-N-[4-(amino-methyl)-benzyl]-N-n-butyl-amide |
| 98 | tetrahydrofuran-2-yl-methyl | 566 | — | — | 2-[2-(4-amidinophenyl)ethyl]-1-(tetrahydrofuran-2-yl-methyl)-benzimidazol-5-yl-carboxylic acid-N-[4-(amino-methyl)-benzyl]-N-n-butyl-amide |
| 99 | 2-thiophenyl-methyl | 578 | — | 290 | 2-[2-(4-amidinophenyl)ethyl]-1-(2-thiophenyl-methyl)-benzimidazol-5-yl-carboxylic acid-N-[4-(amino-methyl)-benzyl]-N-n-butyl-amide |
| 100 | 1,3-benzodioxol-5-yl-methyl | 616 | — | 309 | 2-[2-(4-amidinophenyl)ethyl]-1-(1,3-benzodioxol-5-yl-methyl)-benzimidazol-5-yl-carboxylic acid-N-[4-(amino-methyl)-benzyl]-N-n-butyl-amide |

*[M + H]⁺;
[M + 2H]²⁺

TABLE 3

Compounds of general formula (I) according to the invention wherein the following definitions apply:

—R²: —C(=NH)NH₂; —R³: 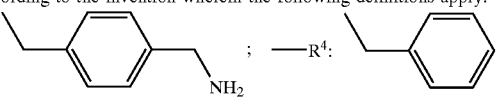 ; —R⁴: 

| Ex. | —R¹ | calc. [M] | found* | found# | Chemical name |
|---|---|---|---|---|---|
| 101 | n-decyl- | 656 | 657 | 329 | 2-[2-(4-amidinophenyl)ethyl]-1-n-decyl-benzimidazol-5-yl-carboxylic acid-N-[4-(amino-methyl)-benzyl]-N-benzyl-amide |
| 102 | 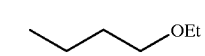 | 602 | 603 | — | 2-[2-(4-amidinophenyl)ethyl]-1-(3-ethoxypropyl)-benzimidazol-5-yl-carboxylic acid-N-[4-(amino-methyl)-benzyl]-N-benzyl-amide |
| 103 | 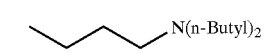 | 685 | 686 | 343 | 2-[2-(4-amidinophenyl)ethyl]-1-(3-di-n-butylaminopropyl)-benzimidazol-5-yl-carboxylic acid-N-[4-(amino-methyl)-benzyl]-N-benzyl-amide |
| 104 | 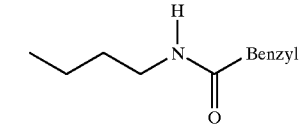 | 691 | — | — | 2-[2-(4-amidinophenyl)ethyl]-1-[3-(benzylcarbonylamino)-propyl]-benzimidazol-5-yl-carboxylic acid-N-[4-(amino-methyl)-benzyl]-N-benzyl-amide |
| 105 | 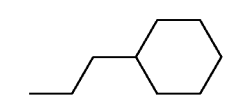 | 626 | — | — | 2-[2-(4-amidinophenyl)ethyl]-1-(2-cyclohexylethyl)-benzimidazol-5-yl-carboxylic acid-N-[4-(amino-methyl)-benzyl]-N-benzyl-amide |
| 106 | 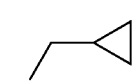 | 570 | — | — | 2-[2-(4-amidinophenyl)ethyl]-1-cyclopropylmethyl-benzimidazol-5-yl-carboxylic acid-N-[4-(amino-methyl)-benzyl]-N-benzyl-amide |
| 107 | 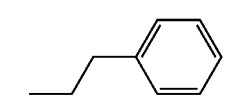 | 620 | 621 | — | 2-[2-(4-amidinophenyl)ethyl]-1-(2-phenylethyl)-benzimidazol-5-yl-carboxylic acid-N-[4-(amino-methyl)-benzyl]-N-benzyl-amide |
| 108 | 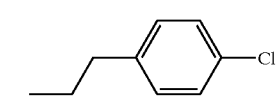 | 654 | — | — | 2-[2-(4-amidinophenyl)ethyl]-1-[2-(4-chlorophenyl)ethyl]-benzimidazol-5-yl-carboxylic acid-N-[4-(amino-methyl)-benzyl]-N-benzyl-amide |
| 109 | 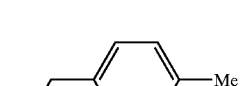 | 620 | 621 | — | 2-[2-(4-amidinophenyl)ethyl]-1-(4-methylbenzyl)-benzimidazol-5-yl-carboxylic acid-N-[4-(amino-methyl)-benzyl]-N-benzyl-amide |
| 110 | 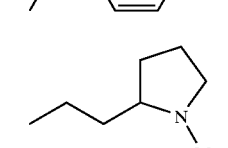 | 627 | 628 | 314 | 2-[2-(4-amidinophenyl)ethyl]-1-[2-(1-methylpyrrolidin-2-yl)-ethyl]-benzimidazol-5-yl-carboxylic acid-N-[4-(amino-methyl)-benzyl]-N-benzyl-amide |
| 111 | 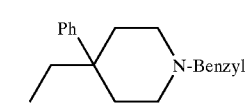 | 779 | — | 391 | 2-[2-(4-amidinophenyl)ethyl]-1-[(1-benzyl-4-phenyl-piperidin-4-yl)-methyl]-benzimidazol-5-yl-carboxylic acid-N-[4-(amino-methyl)-benzyl]-N-benzyl-amide |
| 112 | 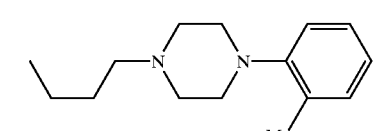 | 732 | 733 | 367 | 2-[2-(4-amidinophenyl)ethyl]-1-{3-[4-(2-methylphenyl)-piperazin-1-yl]-propyl}-benzimidazol-5-yl-carboxylic acid-N-[4-(amino-methyl)-benzyl]-N-benzyl-amide |

TABLE 3-continued

Compounds of general formula (I) according to the invention wherein the following definitions apply:

—R²: —C(=NH)NH₂; —R³: 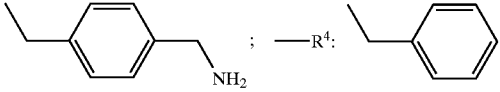 ; —R⁴: 

| Ex. | —R¹ | calc. [M] | found* | found# | Chemical name |
|---|---|---|---|---|---|
| 113 | 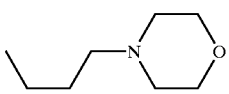 | 643 | — | — | 2-[2-(4-amidinophenyl)ethyl]-1-[3-(morpholin-4-yl)-propyl]-benzimidazol-5-yl-carboxylic acid-N-[4-(amino-methyl)-benzyl]-N-benzyl-amide |
| 114 | 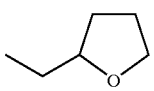 | 600 | 601 | — | 2-[2-(4-amidinophenyl)ethyl]-1-(tetrahydrofuran-2-yl-methyl)-benzimidazol-5-yl-carboxylic acid-N-[4-(amino-methyl)-benzyl]-N-benzyl-amide |
| 115 | 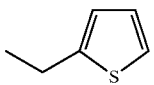 | 612 | 613 | — | 2-[2-(4-amidinophenyl)ethyl]-1-(2-thiophenyl-methyl)-benzimidazol-5-yl-carboxylic acid-N-[4-(amino-methyl)-benzyl]-N-benzyl-amide |
| 116 | 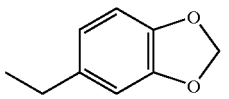 | 650 | 651 | 326 | 2-[2-(4-amidinophenyl)ethyl]-1-(1,3-benzodioxol-5-yl-methyl)-benzimidazol-5-yl-carboxylic acid-N-[4-(amino-methyl)-benzyl]-N-benzyl-amide |

*[M + H]⁺;
[M + 2H]²⁺

TABLE 4

Compounds of general formula (I) according to the invention wherein the following definitions apply:

—R²: —C(=NH)NH₂; —R³: 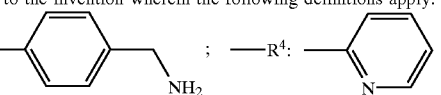 ; —R⁴: 

| Ex. | —R¹ | calc. [M] | found* | found# | Chemical name |
|---|---|---|---|---|---|
| 117 | n-decyl- | 657 | 658 | 329 | 2-[2-(4-amidinophenyl)ethyl]-1-n-decyl-benzimidazol-5-yl-carboxylic acid-N-[4-(amino-methyl)-benzyl]-N-(2-pyridyl)-amide |
| 118 | 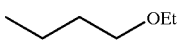 | 603 | 604 | 302 | 2-[2-(4-amidinophenyl)ethyl]-1-(3-ethoxypropyl)-benzimidazol-5-yl-carboxylic acid-N-[4-(amino-methyl)-benzyl]-N-(2-pyridyl)-amide |
| 119 | 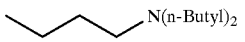 | 686 | — | 344 | 2-[2-(4-amidinophenyl)ethyl]-1-(3-di-n-butylaminopropyl)-benzimidazol-5-yl-carboxylic acid-N-[4-(amino-methyl)-benzyl]-N-(2-pyridyl)-amide |
| 120 | 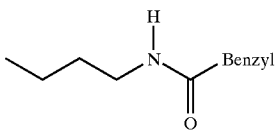 | 692 | — | — | 2-[2-(4-amidinophenyl)ethyl]-1-[3-(benzylcarbonylamino)-propyl]-benzimidazol-5-yl-carboxylic acid-N-[4-(amino-methyl)-benzyl]-N-(2-pyridyl)-amide |
| 121 | 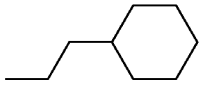 | 627 | 628 | 314 | 2-[2-(4-amidinophenyl)ethyl]-1-(2-cyclohexylethyl)-benzimidazol-5-yl-carboxylic acid-N-[4-(amino-methyl)-benzyl]-N-(2-pyridyl)-amide |

TABLE 4-continued

Compounds of general formula (I) according to the invention wherein the following definitions apply:

—R²: —C(=NH)NH₂;  —R³: 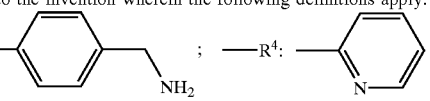 ;  —R⁴: 

| Ex. | —R¹ | calc. [M] | found* | found# | Chemical name |
|---|---|---|---|---|---|
| 122 | 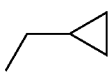 | 571 | — | 286 | 2-[2-(4-amidinophenyl)ethyl]-1-cyclopropylmethyl-benzimidazol-5-yl-carboxylic acid-N-[4-(amino-methyl)-benzyl]-N-(2-pyridyl)-amide |
| 123 | 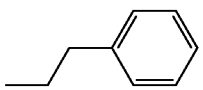 | 621 | — | 311 | 2-[2-(4-amidinophenyl)ethyl]-1-(2-phenylethyl)-benzimidazol-5-yl-carboxylic acid-N-[4-(amino-methyl)-benzyl]-N-(2-pyridyl)-amide |
| 124 | 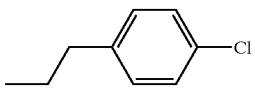 | 655 | — | 329 | 2-[2-(4-amidinophenyl)ethyl]-1-[2-(4-chlorophenyl)ethyl]-benzimidazol-5-yl-carboxylic acid-N-[4-(amino-methyl)-benzyl]-N-(2-pyridyl)-amide |
| 125 | 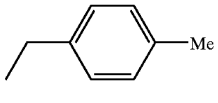 | 621 | — | 311 | 2-[2-(4-amidinophenyl)ethyl]-1-(4-methylbenzyl)-benzimidazol-5-yl-carboxylic acid-N-[4-(amino-methyl)-benzyl]-N-(2-pyridyl)-amide |
| 126 | 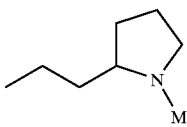 | 628 | — | 315 | 2-[2-(4-amidinophenyl)ethyl]-1-[2-(1-methylpyrrolidin-2-yl)-ethyl]-benzimidazol-5-yl-carboxylic acid-N-[4-(amino-methyl)-benzyl]-N-(2-pyridyl)-amide |
| 127 | 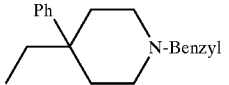 | 780 | — | — | 2-[2-(4-amidinophenyl)ethyl]-1-[(1-benzyl-4-phenyl-piperidin-4-yl)-methyl]-benzimidazol-5-yl-carboxylic acid-N-[4-(amino-methyl)-benzyl]-N-(2-pyridyl)-amide |
| 128 | 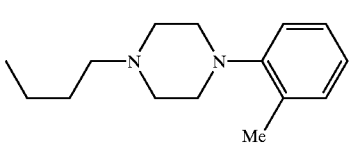 | 733 | 734 | 367 | 2-[2-(4-amidinophenyl)ethyl]-1-{3-[4-(2-methylphenyl)-piperazin-1-yl]-propyl}-benzimidazol-5-yl-carboxylic acid-N-[4-(amino-methyl)-benzyl]-N-(2-pyridyl)-amide |
| 129 | 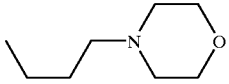 | 644 | 645 | 323 | 2-[2-(4-amidinophenyl)ethyl]-1-[3-(morpholin-4-yl)-propyl]-benzimidazol-5-yl-carboxylic acid-N-[4-(amino-methyl)-benzyl]-N-(2-pyridyl)-amide |
| 130 | 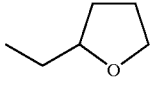 | 601 | — | 301 | 2-[2-(4-amidinophenyl)ethyl]-1-(tetrahydrofuran-2-yl-methyl)-benzimidazol-5-yl-carboxylic acid-N-[4-(amino-methyl)-benzyl]-N-(2-pyridyl)-amide |
| 131 | 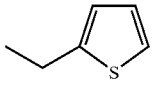 | 613 | — | 307 | 2-[2-(4-amidinophenyl)ethyl]-1-(2-thiophenyl-methyl)-benzimidazol-5-yl-carboxylic acid-N-[4-(amino-methyl)-benzyl]-N-(2-pyridyl)-amide |
| 132 | 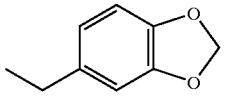 | 651 | 652 | 326 | 2-[2-(4-amidinophenyl)ethyl]-1-(1,3-benzodioxol-5-yl-methyl)-benzimidazol-5-yl-carboxylic acid-N-[4-(amino-methyl)-benzyl]-N-(2-pyridyl)-amide |

*[M + H]⁺;
[M + 2H]²⁺

TABLE 5

Compounds of general formula (I) according to the invention wherein the following definitions apply:

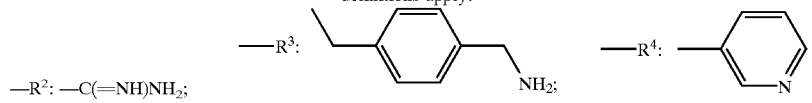

—R²: —C(=NH)NH₂;

| Ex. | —R¹ | calc. [M] | found * | found # | Chemical name |
|---|---|---|---|---|---|
| 133 | n-decyl- | 657 | 658 | 329 | 2-[2-(4-amidinophenyl)ethyl]-1-n-decyl-benzimidazol-5-yl-carboxylic acid-N-[4-(amino-methyl)-benzyl]-N-(3-pyridyl)-amide |
| 134 | ~~~OEt | 603 | 604 | 302 | 2-[2-(4-amidinophenyl)ethyl]-1-(3-ethoxypropyl)-benzimidazol-5-yl-carboxylic acid-N-[4-(amino-methyl)-benzyl]-N-(3-pyridyl)-amide |
| 135 | ~~~N(n-Butyl)₂ | 686 | 687 | 344 | 2-[2-(4-amidinophenyl)ethyl]-1-(3-di-n-butylaminopropyl)-benzimidazol-5-yl-carboxylic acid-N-[4-(amino-methyl)-benzyl]-N-(3-pyridyl)-amide |
| 136 | ~~~N(H)C(=O)Benzyl | 692 | — | 347 | 2-[2-(4-amidinophenyl)ethyl]-1-[3-(benzylcarbonylamino)-propyl]-benzimidazol-5-yl-carboxylic acid-N-[4-(amino-methyl)-benzyl]-N-(3-pyridyl)-amide |
| 137 | ~~cyclohexyl | 627 | — | 314 | 2-[2-(4-amidinophenyl)ethyl]-1-(2-cyclohexylethyl)-benzimidazol-5-yl-carboxylic acid-N-[4-(amino-methyl)-benzyl]-N-(3-pyridyl)-amide |
| 138 | ~cyclopropyl | 571 | 572 | 286 | 2-[2-(4-amidinophenyl)ethyl]-1-cyclopropylmethyl-benzimidazol-5-yl-carboxylic acid-N-[4-(amino-methyl)-benzyl]-N-(3-pyridyl)-amide |
| 139 | ~~Ph | 621 | — | 311 | 2-[2-(4-amidinophenyl)ethyl]-1-(2-phenylethyl)-benzimidazol-5-yl-carboxylic acid-N-[4-(amino-methyl)-benzyl]-N-(3-pyridyl)-amide |
| 140 | ~~C₆H₄-Cl | 655 | — | 629 | 2-[2-(4-amidinophenyl)ethyl]-1-[2-(4-chlorophenyl)ethyl]-benzimidazol-5-yl-carboxylic acid-N-[4-(amino-methyl)-benzyl]-N-(3-pyridyl)-amide |
| 141 | ~C₆H₄-Me | 621 | 622 | 311 | 2-[2-(4-amidinophenyl)ethyl]-1-(4-methylbenzyl)-benzimidazol-5-yl-carboxylic acid-N-[4-(amino-methyl)-benzyl]-N-(3-pyridyl)-amide |
| 142 | ~~(1-methylpyrrolidin-2-yl) | 628 | — | 315 | 2-[2-(4-amidinophenyl)ethyl]-1-[2-(1-methylpyrrolidin-2-yl)-ethyl]-benzimidazol-5-yl-carboxylic acid-N-[4-(amino-methyl)-benzyl]-N-(3-pyridyl)-amide |
| 143 | (1-benzyl-4-phenyl-piperidin-4-yl)methyl | 780 | — | — | 2-[2-(4-amidinophenyl)ethyl]-1-[(1-benzyl-4-phenyl-piperidin-4-yl)-methyl]-benzimidazol-5-yl-carboxylic acid-N-[4-(amino-methyl)-benzyl]-N-(3-pyridyl)-amide |
| 144 | ~~~N(piperazinyl)-C₆H₄-Me | 733 | — | 367 | 2-[2-(4-amidinophenyl)ethyl]-1-{3-[4-(2-methylphenyl)-piperazin-1-yl]-propyl}-benzimidazol-5-yl-carboxylic acid-N-[4-(amino-methyl)-benzyl]-N-(3-pyridyl)-amide |

TABLE 5-continued

Compounds of general formula (I) according to the invention wherein the following definitions apply:

—R²: —C(=NH)NH₂;  —R³: 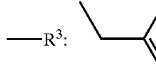  —R⁴: 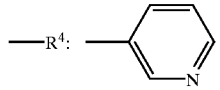

| Ex. | —R¹ | calc. [M] | found * | found # | Chemical name |
|---|---|---|---|---|---|
| 145 | 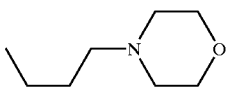 | 644 | 645 | 323 | 2-[2-(4-amidinophenyl)ethyl]-1-[3-(morpholin-4-yl)-propyl]-benzimidazol-5-yl-carboxylic acid-N-[4-(amino-methyl)-benzyl]-N-(3-pyridyl)-amide |
| 146 | 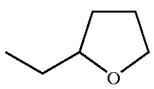 | 601 | — | 301 | 2-[2-(4-amidinophenyl)ethyl]-1-(tetrahydrofuran-2-yl-methyl)-benzimidazol-5-yl-carboxylic acid-N-[4-(amino-methyl)-benzyl]-N-(3-pyridyl)-amide |
| 147 | 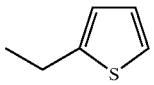 | 613 | 614 | 307 | 2-[2-(4-amidinophenyl)ethyl]-1-(2 thiophenyl-methyl)-benzimidazol-5-yl-carboxylic acid-N-[4-(amino-methyl)-benzyl]-N-(3-pyridyl)-amide |
| 148 | 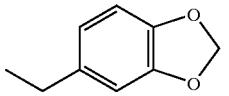 | 651 | — | 326 | 2-[2-(4-amidinophenyl)ethyl]-1-(1,3-benzodioxol-5-yl-methyl)-benzimidazol-5-yl-carboxylic acid-N-[4-(amino-methyl)-benzyl]-N-(3-pyridyl)-amide |

*[M + H]⁺;
[M + 2H]²⁺

TABLE 6

Compounds of general formula (I) according to the invention wherein the following definitions apply:

—R²: —C(=NH)NH₂;  —R³: 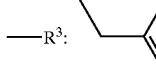  —R⁴: 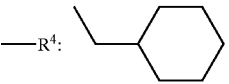

| Ex. | —R¹ | calc. [M] | found * | found # | Chemical name |
|---|---|---|---|---|---|
| 149 | n-decyl- | 662 | 663 | — | 2-[2-(4-amidinophenyl)ethyl]-1-n-decyl-benzimidazol-5-yl-carboxylic acid-N-[4-(amino-methyl)-benzyl]-N-cyclohexylmethyl-amide |
| 150 | 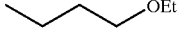 | 608 | — | — | 2-[2-(4-amidinophenyl)ethyl]-1-(3-ethoxypropyl)-benzimidazol-5-yl-carboxylic acid-N-[4-(amino-methyl)-benzyl]-N-cyclohexylmethyl-amide |
| 151 | 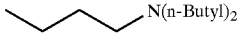 | 691 | — | 346 | 2-[2-(4-amidinophenyl)ethyl]-1-(3-di-n-butylaminopropyl)-benzimidazol-5-yl-carboxylic acid-N-[4-(amino-methyl)-benzyl]-N-cyclohexylmethyl-amide |
| 152 | 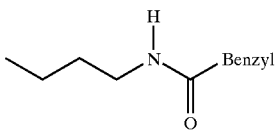 | 697 | — | — | 2-[2-(4-amidinophenyl)ethyl]-1-[3-(benzylcarbonylamino)-propyl]-benzimidazol-5-yl-carboxylic acid-N-[4-(amino-methyl)-benzyl]-N-cyclohexylmethyl-amide |

TABLE 6-continued

Compounds of general formula (I) according to the invention wherein the following definitions apply:

—R²: —C(=NH)NH₂;  —R³: 4-(aminomethyl)benzyl (CH₂-C₆H₄-CH₂NH₂);  —R⁴: cyclohexylmethyl

| Ex. | —R¹ | calc. [M] | found * | found # | Chemical name |
|---|---|---|---|---|---|
| 153 | cyclohexylethyl | 632 | −4 | — | 2-[2-(4-amidinophenyl)ethyl]-1-(2-cyclohexylethyl)-benzimidazol-5-yl-carboxylic acid-N-[4-(amino-methyl)-benzyl]-N-cyclohexylmethyl-amide |
| 154 | cyclopropylmethyl | 576 | — | — | 2-[2-(4-amidinophenyl)ethyl]-1-cyclopropylmethyl-benzimidazol-5-yl-carboxylic acid-N-[4-(amino-methyl)-benzyl]-N-cyclohexylmethyl-amide |
| 155 | 2-phenylethyl | 626 | — | — | 2-[2-(4-amidinophenyl)ethyl]-1-(2-phenylethyl)-benzimidazol-5-yl-carboxylic acid-N-[4-(amino-methyl)-benzyl]-N-cyclohexylmethyl-amide |
| 156 | 2-(4-chlorophenyl)ethyl | 660 | — | — | 2-[2-(4-amidinophenyl)ethyl]-1-[2-(4-chlorophenyl)ethyl]-benzimidazol-5-yl-carboxylic acid-N-[4-(amino-methyl)-benzyl]-N-cyclohexylmethyl-amide |
| 157 | 4-methylbenzyl | 626 | — | — | 2-[2-(4-amidinophenyl)ethyl]-1-(4-methylbenzyl)-benzimidazol-5-yl-carboxylic acid-N-[4-(amino-methyl)-benzyl]-N-cyclohexylmethyl-amide |
| 158 | 2-(1-methylpyrrolidin-2-yl)ethyl | 633 | — | — | 2-[2-(4-amidinophenyl)ethyl]-1-[2-(1-methylpyrrolidin-2-yl)-ethyl]-benzimidazol-5-yl-carboxylic acid-N-[4-(amino-methyl)-benzyl]-N-cyclohexylmethyl-amide |
| 159 | (1-benzyl-4-phenyl-piperidin-4-yl)methyl | 785 | — | — | 2-[2-(4-amidinophenyl)ethyl]-1-[(1-benzyl-4-phenyl-piperidin-4-yl)-methyl]-benzimidazol-5-yl-carboxylic acid-N-[4-(amino-methyl)-benzyl]-N-cyclohexylmethyl-amide |
| 160 | 3-[4-(2-methylphenyl)-piperazin-1-yl]propyl | 662 | 663 | — | 2-[2-(4-amidinophenyl)ethyl]-1-{3-[4-(2-methylphenyl)-piperazin-1-yl]-propyl}-benzimidazol-5-yl-carboxylic acid-N-[4-(amino-methyl)-benzyl]-N-cyclohexylmethyl-amide |
| 161 | 3-(morpholin-4-yl)propyl | 649 | — | — | 2-[2-(4-amidinophenyl)ethyl]-1-[3-(morpholin-4-yl)-propyl]-benzimidazol-5-yl-carboxylic acid-N-[4-(amino-methyl)-benzyl]-N-cyclohexylmethyl-amide |
| 162 | (tetrahydrofuran-2-yl)methyl | 606 | — | — | 2-[2-(4-amidinophenyl)ethyl]-1-(tetrahydrofuran-2-yl-methyl)-benzimidazol-5-yl-carboxylic acid-N-[4-(amino-methyl)-benzyl]-N-cyclohexylmethyl-amide |
| 163 | (thiophen-2-yl)methyl | 618 | — | — | 2-[2-(4-amidinophenyl)ethyl]-1-(2-thiophenyl-methyl)-benzimidazol-5-yl-carboxylic acid-N-[4-(amino-methyl)-benzyl]-N-cyclohexylmethyl-amide |

TABLE 6-continued

Compounds of general formula (I) according to the invention wherein the following definitions apply:

—R²: —C(=NH)NH₂;    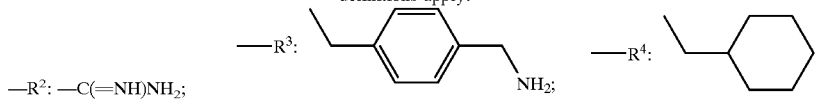

| Ex. | —R¹ | calc. [M] | found * | found # | Chemical name |
|---|---|---|---|---|---|
| 164 | 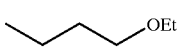 | 656 | — | — | 2-[2-(4-amidinophenyl)ethyl]-1-(1,3-benzodioxol-5-yl-methyl)-benzimidazol-5-yl-carboxylic acid-N-[4-(amino-methyl)-benzyl]-N-cyclohexylmethyl-amide |

*[M + H]⁺;
[M + 2H]²⁺

TABLE 7

Compounds of general formula (I) according to the invention wherein the following definitions apply:

—R²: —C(=NH)NH₂;    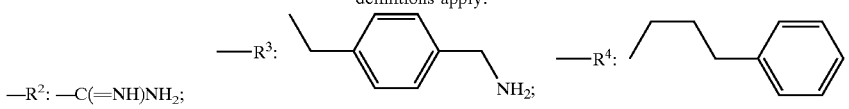

| Ex. | —R¹ | calc. [M] | found * | found # | Chemical name |
|---|---|---|---|---|---|
| 165 | n-decyl- | 684 | — | 343 | 2-[2-(4-amidinophenyl)ethyl]-1-n-decyl-benzimidazol-5-yl-carboxylic acid-N-[4-(amino-methyl)-benzyl]-N-(3-phenylpropyl)-amide |
| 166 |  OEt | 630 | — | — | 2-[2-(4-amidinophenyl)ethyl]-1-(3-ethoxypropyl)-benzimidazol-5-yl-carboxylic acid-N-[4-(amino-methyl)-benzyl]-N-(3-phenylpropyl)-amide |
| 167 | 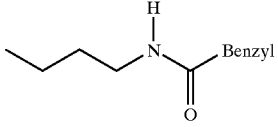 N(n-Butyl)₂ | 714 | — | — | 2-[2-(4-amidinophenyl)ethyl]-1-(3-di-n-butylaminopropyl)benzimidazol-5-yl-carboxylic acid-N-[4-(amino-methyl)-benzyl]-N-(3-phenylpropyl)-amide |
| 168 | 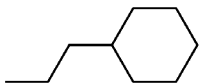 | 719 | — | — | 2-[2-(4-amidinophenyl)ethyl]-1-[3-(benzylcarbonylamino)-propyl]-benzimidazol-5-yl-carboxylic acid-N-[4-(amino-methyl)-benzyl]-N-(3-phenylpropyl)-amide |
| 169 | 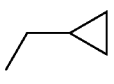 | 654 | — | — | 2-[2-(4-amidinophenyl)ethyl]-1-(2-cyclohexylethyl)-benzimidazol-5-yl-carboxylic acid-N-[4-(amino-methyl)-benzyl]-N-(3-phenylpropyl)-amide |
| 170 | 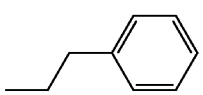 | 598 | — | — | 2-[2-(4-amidinophenyl)ethyl]-1-cyclopropylmethyl-benzimidazol-5-yl-carboxylic acid-N-[4-(amino-methyl)-benzyl]-N-(3-phenylpropyl)-amide |
| 171 | 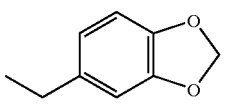 | 648 | — | — | 2-[2-(4-amidinophenyl)ethyl]-1-(2-phenylethyl)-benzimidazol-5-yl carboxylic acid-N-[4-(amino methyl)-benzyl]-N-(3-phenylpropyl)-amide |

TABLE 7-continued

Compounds of general formula (I) according to the invention wherein the following definitions apply:

—R²: —C(=NH)NH₂; —R³: 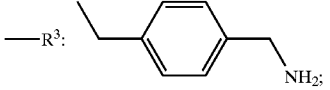 —R⁴: 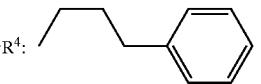

| Ex. | —R¹ | calc. [M] | found * | found # | Chemical name |
|---|---|---|---|---|---|
| 172 | 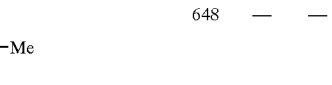 | 682 | — | — | 2-[2-(4-amidinophenyl)ethyl]-1-[2-(4-chlorophenyl)ethyl]-benzimidazol-5-yl-carboxylic acid-N-[4-(amino-methyl)-benzyl]-N-(3 phenylpropyl)-amide |
| 173 | 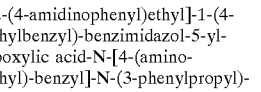 | 648 | — | — | 2-[2-(4-amidinophenyl)ethyl]-1-(4-methylbenzyl)-benzimidazol-5-yl-carboxylic acid-N-[4-(amino-methyl)-benzyl]-N-(3-phenylpropyl)-amide |
| 174 |  | 655 | — | 328 | 2-[2-(4-amidinophenyl)ethyl]-1-[2-(1-methylpyrrolidin-2-yl)-ethyl]-benzimidazol-5-yl-carboxylic acid-N-[4-(amino-methyl)-benzyl]-N-(3-phenylpropyl)-amide |
| 175 | 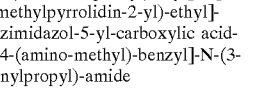 | 807 | — | — | 2-[2-(4-amidinophenyl)ethyl]-1-[(1 benzyl-4-phenyl-piperidine-4-yl)-methyl]-benzimidazol-5-yl-carboxylic acid-N-[4-(amino-methyl)-benzyl]-N-(3-phenylpropyl)-amide |
| 176 |  | 760 | — | — | 2-[2-(4-amidinophenyl)ethyl]-1-{3-[4-(2-methylphenyl)-piperazin-1-yl]-propyl}-benzimidazol-5-yl-carboxylic acid-N-[4-(amino-methyl)-benzyl]-N-(3-phenylpropyl)-amide |
| 177 | 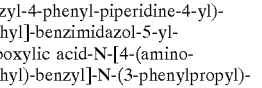 | 671 | — | 336 | 2-[2-(4-amidinophenyl)ethyl]-1-[3-(morpholin-4-yl)-propyl]-benzimidazol-5-yl-carboxylic acid-N-[4-(amino-methyl)-benzyl]-N-(3-phenylpropyl)-amide |
| 178 | 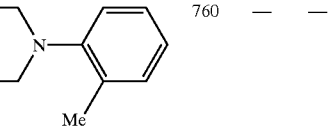 | 628 | — | — | 2-[2-(4-amidinophenyl)ethyl]-1-(tetrahydrofuran-2-yl-methyl)-benzimidazol-5-yl-carboxylic acid-N-[4-(amino-methyl)-benzyl]-N-(3-phenylpropyl)-amide |
| 179 | 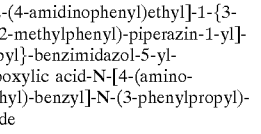 | 640 | — | — | 2-[2-(4-amidinophenyl)ethyl]-1-(2-thiophenyl-methyl)-benzimidazol-5-yl-carboxylic acid-N-[4-(amino-methyl)-benzyl]-N-(3-phenylpropyl)-amide |
| 180 |  | 678 | — | — | 2-[2-(4-amidinophenyl)ethyl]-1-(1,3-benzodioxol-5-yl-methyl)-benzimidazol-5-yl-carboxylic acid-N-[4-(amino-methyl)-benzyl]-N-(3-phenylpropyl)-amide |

*[M + H]⁺;
[M + 2H]²⁺

TABLE 8

Compounds of general formula (I) according to the invention wherein the following definitions apply:

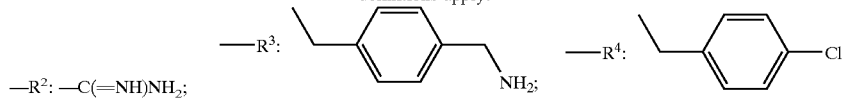

—R²: —C(=NH)NH₂;

| Ex. | —R¹ | calc [M] | found * | found # | Chemical name |
|---|---|---|---|---|---|
| 181 | n-decyl- | 690 | 691 | — | 2-[2-(4-amidinophenyl)ethyl]-1-n-decyl-benzimidazol-5-yl-carboxylic acid-N-[4-(amino-methyl)-benzyl]-N-(4-chlorbenzyl)-amide |
| 182 | ⟋⟍⟋OEt | 636 | 637 | 319 | 2-[2-(4-amidinophenyl)ethyl]-1-(3-ethoxypropyl)-benzimidazol-5-yl-carboxylic acid-N-[4-(amino-methyl)-benzyl]-N-(4-chlorbenzyl)-amide |
| 183 | ⟋⟍⟋N(n-Butyl)₂ | 719 | 720 | 360 | 2-[2-(4-amidinophenyl)ethyl]-1-(3-di-n-butylaminopropyl)-benzimidazol-5-yl-carboxylic acid-N-[4-(amino-methyl)-benzyl]-N-(4 chlorbenzyl)-amide |
| 184 | (butyl-NH-C(=O)-Benzyl) | 726 | — | — | 2-[2-(4-amidinophenyl)ethyl]-1-[3-(benzylcarbonylamino)-propyl]-benzimidazol-5-yl-carboxylic acid-N-[4-(amino-methyl)-benzyl]-N-(4-chlorbenzyl)-amide |
| 185 | (ethyl-cyclohexyl) | 644 | — | — | 2-[2-(4-amidinophenyl)ethyl]-1-(2-cyclohexylethyl)-benzimidazol-5-yl-carboxylic acid-N-[4-(amino-methyl)-benzyl]-N-(4-chlorbenzyl)-amide |
| 186 | (methyl-cyclopropyl) | 604 | 605 | — | 2-[2-(4-amidinophenyl)ethyl]-1-cyclopropylmethyl-benzimidazol-5-yl-carboxylic acid-N-[4-(amino-methyl)-benzyl]-N-(4-chlorbenzyl)-amide |
| 187 | (ethyl-phenyl) | 654 | — | — | 2-[2-(4-amidinophenyl)ethyl]-1-(2-phenylethyl)-benzimidazol-5-yl-carboxylic acid-N-[4-(amino-methyl)-benzyl]-N-(4-chlorbenzyl)-amide |
| 188 | (ethyl-4-Cl-phenyl) | 688 | — | — | 2-[2-(4-amidinophenyl)ethyl]-1-[2-(4-chlorophenyl)ethyl]-benzimidazol-5-yl-carboxylic acid-N-[4-(amino-methyl)-benzyl]-N-(4-chlorbenzyl)-amide |
| 189 | (ethyl-4-Me-phenyl) | 654 | — | — | 2-[2-(4-amidinophenyl)ethyl]-1-(4-methylbenzyl)-benzimidazol-5-yl-carboxylic acid-N-[4-(amino-methyl)-benzyl]-N-(4-chlorbenzyl)-amide |
| 190 | (ethyl-1-methylpyrrolidin-2-yl) | 661 | 662 | 331 | 2-[2-(4-amidinophenyl)ethyl]-1-[2-(1-methylpyrrolidin-2-yl)-ethyl]-benzimidazol-5-yl-carboxylic acid-N-[4-(amino-methyl)-benzyl]-N-(4-chlorbenzyl)-amide |
| 191 | (ethyl-4-Ph-4-N-benzyl-piperidine) | 766 | — | — | 2-[2-(4-amidinophenyl)ethyl]-1-[(1-benzyl-4-phenyl-piperidin-4-yl)-methyl]-benzimidazol-5-yl-carboxylic acid-N-[4-(amino-methyl)-benzyl]-N-(4-chlorbenzyl)-amide |

TABLE 8-continued

Compounds of general formula (I) according to the invention wherein the following definitions apply:

—R²: —C(=NH)NH₂;

—R³: 4-(aminomethyl)benzyl;

—R⁴: 4-chlorobenzyl

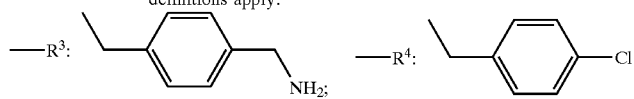

| Ex. | —R¹ | calc [M] | found * | found # | Chemical name |
|---|---|---|---|---|---|
| 192 | (butyl-piperazinyl-2-methylphenyl group) | 766 | — | 384 | 2-[2-(4-amidinophenyl)ethyl]-1-{3-[4-(2-methylphenyl)-piperazin-1-yl]-propyl}-benzimidazol-5-yl-carboxylic acid-N-[4-(amino-methyl)-benzyl]-N-(4-chlorbenzyl)-amide |
| 193 | (butyl-morpholinyl group) | 677 | — | — | 2-[2-(4-amidinophenyl)ethyl]-1-[3-(morpholin-4-yl)-propyl]-benzimidazol-5-yl-carboxylic acid-N-[4-(amino-methyl)-benzyl]-N-(4-chlorbenzyl)-amide |
| 194 | (tetrahydrofuranylmethyl) | 634 | 635 | — | 2-[2-(4-amidinophenyl)ethyl]-1-(tetrahydrofuran-2-yl-methyl)-benzimidazol-5-yl-carboxylic acid-N-[4-(amino-methyl)-benzyl]-N-(4-chlorbenzyl)-amide |
| 195 | (thiophenylmethyl) | 646 | 647 | — | 2-[2-(4-amidinophenyl)ethyl]-1-(2-thiophenyl-methyl)-benzimidazol-5-yl-carboxylic acid-N-[4-(amino-methyl)-benzyl]-N-(4-chlorbenzyl)-amide |
| 196 | (1,3-benzodioxol-5-ylmethyl) | 684 | 685 | — | 2-[2-(4-amidinophenyl)ethyl]-1-(1,3-benzodioxol-5-yl-methyl)-benzimidazol-5-yl-carboxylic acid-N-[4-(amino-methyl)-benzyl]-N-(4-chlorbenzyl)-amide |

*[M + H]⁺;
[M − 2H]²⁺

TABLE 9

Compounds of general formula (I) according to the invention wherein the following definitions apply:

—R²: —C(=NH)NH₂;

—R³: 4-(aminomethyl)benzyl;

—R⁴: 3-trifluoromethylbenzyl

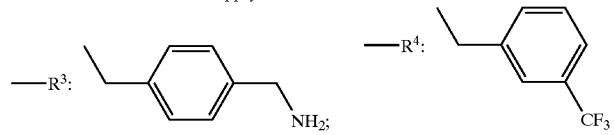

| Ex. | —R¹ | calc. [M] | found * | found # | Chemical name |
|---|---|---|---|---|---|
| 197 | n-decyl- | 724 | 725 | 363 | 2-[2-(4-amidinophenyl)ethyl]-1-n-decyl-benzimidazol-5-yl-carboxylic acid-N-[4-(amino-methyl)-benzyl]-N-(3-trifluoromethylbenzyl)-amide |
| 198 | —(CH₂)₃OEt | 670 | 671 | 336 | 2-[2-(4-amidinophenyl)ethyl]-1-(3-ethoxypropyl)-benzimidazol-5-yl-carboxylic acid-N-[4-(amino-methyl)-benzyl]-N-(3-trifluoromethylbenzyl)-amide |
| 199 | —(CH₂)₃N(n-Butyl)₂ | 753 | 754 | 377 | 2-[2-(4-amidinophenyl)ethyl]-1-(3-di-n-butylaminopropyl)-benzimidazol-5-yl-carboxylic acid-N-[4-(amino-methyl)-benzyl]-N-(3-trifluoromethylbenzyl)-amide |

TABLE 9-continued

Compounds of general formula (I) according to the invention wherein the following definitions apply:

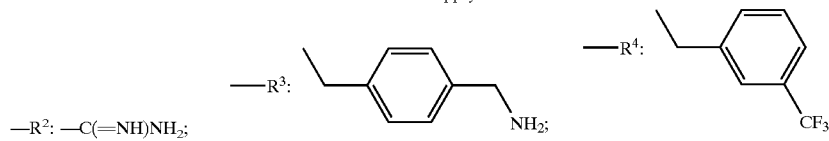

—R²: —C(=NH)NH₂;

| Ex. | —R¹ | calc. [M] | found * | found # | Chemical name |
|---|---|---|---|---|---|
| 200 | 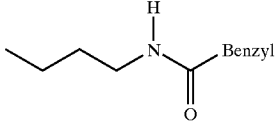 | 847 | — | 424 | 2-[2-(4-amidinophenyl)ethyl]-1-[3-(benzylcarbonylamino)-propyl]-benzimidazol-5-yl-carboxylic acid-N-[4-(amino-methyl)-benzyl]-N-(3-trifluoromethylbenzyl)-amide |
| 201 | 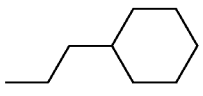 | 753 | 754 | 377 | 2-[2-(4-amidinophenyl)ethyl]-1-(2-cyclohexylethyl)-benzimidazol-5-yl-carboxylic acid-N-[4-(amino-methyl)-benzyl]-N-(3-trifluoromethylbenzyl)-amide |
| 202 | 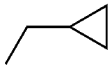 | 638 | 639 | 320 | 2-[2-(4-amidinophenyl)ethyl]-1-cyclopropylmethyl-benzimidazol-5-yl-carboxylic acid-N-[4-(amino-methyl)-benzyl]-N-(3-trifluoromethylbenzyl)-amide |
| 203 | 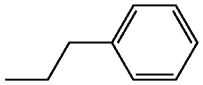 | 688 | — | — | 2-[2-(4-amidinophenyl)ethyl]-1-(2-phenylethyl)-benzimidazol-5-yl-carboxylic acid-N-[4-(amino-methyl)-benzyl]-N-(3-trifluoromethylbenzyl)-amide |
| 204 | 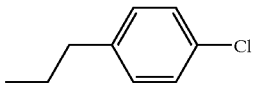 | 722 | — | 362 | 2-[2-(4-amidinophenyl)ethyl]-1-[2-(4-chlorophenyl)ethyl]-benzimidazol-5-yl-carboxylic acid-N-[4-(amino-methyl)-benzyl]-N-(3-trifluoromethylbenzyl)-amide |
| 205 | 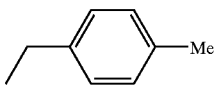 | 688 | — | 345 | 2-[2-(4-amidinophenyl)ethyl]-1-(4-methylbenzyl)-benzimidazol-5-yl-carboxylic acid-N-[4-(amino-methyl)-benzyl]-N-(3-trifluoromethylbenzyl)-amide |
| 206 | 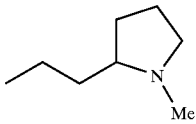 | 695 | — | 348 | 2-[2-(4-amidinophenyl)ethyl]-1-[2-(1-methylpyrrolidin-2-yl)-ethyl]-benzimidazol-5-yl-carboxylic acid-N-[4-(amino-methyl)-benzyl]-N-(3-trifluoromethylbenzyl)-amide |
| 207 | 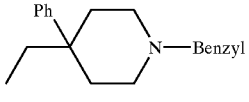 | 847 | — | 424 | 2-[2-(4-amidinophenyl)ethyl]-1-[(1-benzyl-4-phenyl-piperidin-4-yl)-methyl]-benzimidazol-5-yl-carboxylic acid-N-[4-(amino-methyl)-benzyl]-N-(3-trifluoromethylbenzyl)-amide |
| 208 | 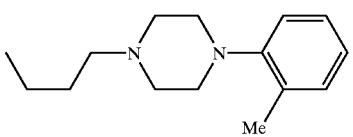 | 800 | 801 | 401 | 2-[2-(4-amidinophenyl)ethyl]-1-{3-[4-(2-methylphenyl)-piperazin-1-yl]-propyl}-benzimidazol-5-yl-carboxylic acid-N-[4-(amino-methyl)-benzyl]-N-(3-trifluoromethylbenzyl)-amide |
| 209 | 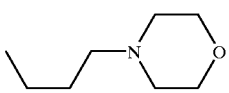 | 711 | 712 | 356 | 2-[2-(4-amidinophenyl)ethyl]-1-[3-(morpholin-4-yl)-propyl]-benzimidazol-5-yl-carboxylic acid-N-[4-(amino-methyl)-benzyl]-N-(3-trifluoromethylbenzyl)-amide |

TABLE 9-continued

Compounds of general formula (I) according to the invention wherein the following definitions apply:

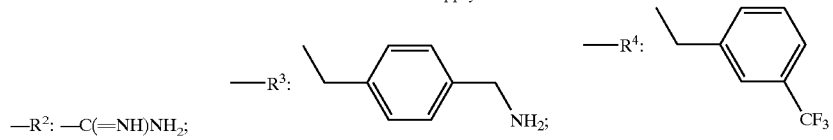

—R²: —C(=NH)NH₂;

| Ex. | —R¹ | calc. [M] | found * | found # | Chemical name |
|---|---|---|---|---|---|
| 210 | tetrahydrofuran-2-ylmethyl | 668 | 669 | 335 | 2-[2-(4-amidinophenyl)ethyl]-1-(tetrahydrofuran-2-yl-methyl)-benzimidazol-5-yl-carboxylic acid-N-[4-(amino-methyl)-benzyl]-N-(3-trifluoromethylbenzyl)-amide |
| 211 | thiophen-2-ylmethyl | 680 | 681 | — | 2-[2-(4-amidinophenyl)ethyl]-1-(2-thiophenyl-methyl)-benzimidazol-5-yl-carboxylic acid-N-[4-(amino-methyl)-benzyl]-N-(3-trifluoromethylbenzyl)-amide |
| 212 | 1,3-benzodioxol-5-ylmethyl | 718 | 719 | 340 | 2-[2-(4-amidinophenyl)ethyl]-1-(1,3-benzodioxol-5-yl-methyl)-benzimidazol-5-yl-carboxylic acid-N-[4-(amino-methyl)-benzyl]-N-(3-trifluoromethylbenzyl)-amide |

*[M + H]⁺;
[M + 2H]²⁺

TABLE 10

Compounds of general formula (I) according to the invention wherein the following definitions apply:

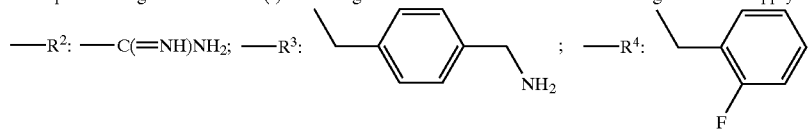

—R²: —C(=NH)NH₂;

| Ex. | —R¹ | calc. [M] | found* | found# | Chemical name |
|---|---|---|---|---|---|
| 213 | n-decyl- | 674 | 675 | 338 | 2-[2-(4-amidinophenyl)ethyl]-1-n-decyl-benzimidazol-5-yl-carboxylic acid-N-[4-(amino-methyl)-benzyl]-N-(2-fluorobenzyl)-amide |
| 214 | –(CH₂)₃–OEt | 620 | 621 | 310 | 2-[2-(4-amidinophenyl)ethyl]-1-(3-ethoxypropyl)-benzimidazol-5-yl-carboxylic acid-N-[4-(amino-methyl)-benzyl]-N-(2-fluorobenzyl)-amide |
| 215 | –(CH₂)₃–N(n-Butyl)₂ | 703 | 704 | 352 | 2-[2-(4-amidinophenyl)ethyl]-1-(3-di-n-butylaminopropyl)-benzimidazol-5-yl-carboxylic acid-N-[4-(amino-methyl)-benzyl]-N-(2-fluorobenzyl)-amide |
| 216 | –(CH₂)₃–N(H)–C(O)–CH₂–Benzyl | 709 | — | — | 2-[2-(4-amidinophenyl)ethyl]-1-[3-(benzylcarbonylamino)-propyl]-benzimidazol-5-yl-carboxylic acid-N-[4-(amino-methyl)-benzyl]-N-(2-fluorobenzyl)-amide |
| 217 | –(CH₂)₂–cyclohexyl | 644 | 645 | 323 | 2-[2-(4-amidinophenyl)ethyl]-1-(2-cyclohexylethyl)-benzimidazol-5-yl-carboxylic acid-N-[4-(amino-methyl)-benzyl]-N-(2-fluorobenzyl)-amide |

TABLE 10-continued

Compounds of general formula (I) according to the invention wherein the following definitions apply:

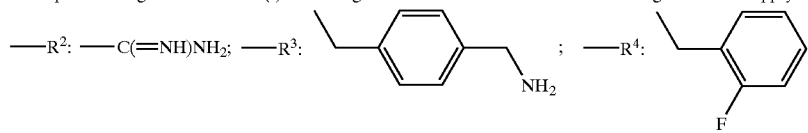

| Ex. | —R¹ | calc. [M] | found* | found# | Chemical name |
|---|---|---|---|---|---|
| 218 | 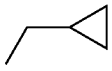 | 558 | 559 | 287 | 2-[2-(4-amidinophenyl)ethyl]-1-cyclopropylmethyl-benzimidazol-5-yl-carboxylic acid-N-[4-(amino-methyl)-benzyl]-N-(2-fluorobenzyl)-amide |
| 219 | 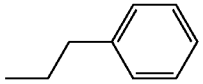 | 638 | — | — | 2-[2-(4-amidinophenyl)ethyl]-1-(2-phenylethyl)-benzimidazol-5-yl-carboxylic acid-N-[4-(amino-methyl)-benzyl]-N-(2-fluorobenzyl)-amide |
| 220 | 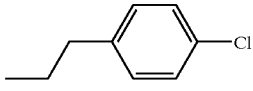 | 672 | — | — | 2-[2-(4-amidinophenyl)ethyl]-1-[2-(4-chlorophenyl)ethyl]-benzimidazol-5-yl-carboxylic acid-N-[4-(amino-methyl)-benzyl]-N-(2-fluorobenzyl)-amide |
| 221 | 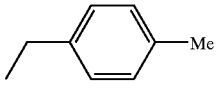 | 638 | — | — | 2-[2-(4-amidinophenyl)ethyl]-1-(4-methylbenzyl)-benzimidazol-5-yl-carboxylic acid-N-[4-(amino-methyl)-benzyl]-N-(2-fluorobenzyl)-amide |
| 222 | 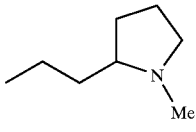 | 645 | — | 323 | 2-[2-(4-amidinophenyl)ethyl]-1-[2-(1-methylpyrrolidin-2-yl)-ethyl]-benzimidazol-5-yl-carboxylic acid-N-[4-(amino-methyl)-benzyl]-N-(2-fluorobenzyl)-amide |
| 223 | 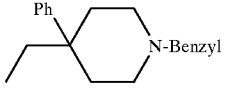 | 797 | — | 399 | 2-[2-(4-amidinophenyl)ethyl]-1-[(1-benzyl-4-phenyl-piperidin-4-yl)-methyl]-benzimidazol-5-yl-carboxylic acid-N-[4-(amino-methyl)-benzyl]-N-(2-fluorobenzyl)-amide |
| 224 | 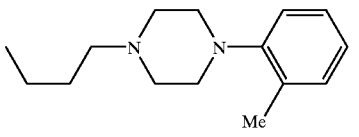 | 750 | 751 | 376 | 2-[2-(4-amidinophenyl)ethyl]-1-{3-[4-(2-methylphenyl)-piperazin-1-yl]-propyl}-benzimidazol-5-yl-carboxylic acid-N-[4-(amino-methyl)-benzyl]-N-(2-fluorobenzyl)-amide |
| 225 | 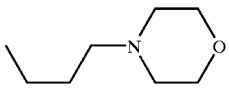 | 620 | — | — | 2-[2-(4-amidinophenyl)ethyl]-1-[3-(morpholin-4-yl)-propyl]-benzimidazol-5-yl-carboxylic acid-N-[4-(amino-methyl)-benzyl]-N-(2-fluorobenzyl)-amide |
| 226 | 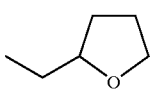 | 618 | — | — | 2-[2-(4-amidinophenyl)ethyl]-1-(tetrahydrofuran-2-yl-methyl)-benzimidazol-5-yl-carboxylic acid-N-[4-(amino-methyl)-benzyl]-N-(2-fluorobenzyl)-amide |
| 227 | 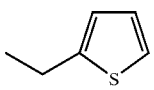 | 630 | 631 | 307 | 2-[2-(4-amidinophenyl)ethyl]-1-(2-thiophenyl-methyl)-benzimidazol-5-yl-carboxylic acid-N-[4-(amino-methyl)-benzyl]-N-(2-fluorobenzyl)-amide |

TABLE 10-continued

Compounds of general formula (I) according to the invention wherein the following definitions apply:

—R²: —C(=NH)NH₂; —R³: 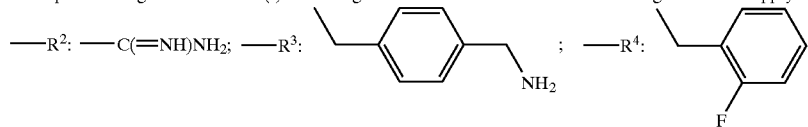 ; —R⁴: 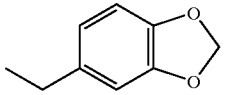

| Ex. | —R¹ | calc. [M] | found* | found# | Chemical name |
|---|---|---|---|---|---|
| 228 | 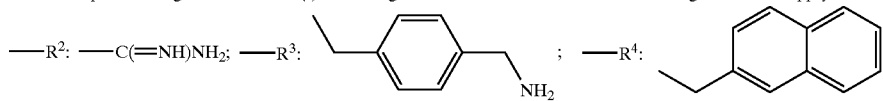 | 668 | — | — | 2-[2-(4-amidinophenyl)ethyl]-1-(1,3-benzodioxol-5-yl-methyl)-benzimidazol-5-yl-carboxylic acid-N-[4-(amino-methyl)-benzyl]-N-(2-fluorobenzyl)-amide |

*[M + H]⁺;
[M + 2H]²⁺

TABLE 11

Compounds of general formula (I) according to the invention wherein the following definitions apply:

—R²: —C(=NH)NH₂; —R³: 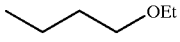 ; —R⁴: 

| Ex. | —R¹ | calc. [M] | found* | found# | Chemical name |
|---|---|---|---|---|---|
| 229 | n-decyl- | 706 | 707 | — | 2-[2-(4-amidinophenyl)ethyl]-1-n-decyl-benzimidazol-5-yl-carboxylic acid-N-[4-(amino-methyl)-benzyl]-N-(2-naphthylmethyl)-amide |
| 230 | 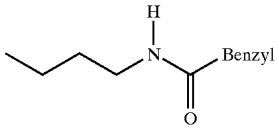 OEt | 652 | 653 | 319 | 2-[2-(4-amidinophenyl)ethyl]-1-(3-ethoxypropyl)-benzimidazol-5-yl-carboxylic acid-N-[4-(amino-methyl)-benzyl]-N-(2-naphthylmethyl)-amide |
| 231 | 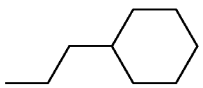 N(n-Butyl)₂ | 735 | — | 369 | 2-[2-(4-amidinophenyl)ethyl]-1-(3-di-n-butylaminopropyl)-benzimidazol-5-yl-carboxylic acid-N-[4-(amino-methyl)-benzyl]-N-(2-naphthylmethyl)-amide |
| 232 | 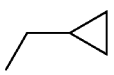 | 741 | — | — | 2-[2-(4-amidinophenyl)ethyl]-1-[3-(benzylcarbonylamino)-propyl]-benzimidazol-5-yl-carboxylic acid-N-[4-(amino-methyl)-benzyl]-N-(2-naphthylmethyl)-amide |
| 233 | 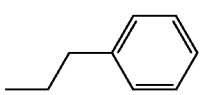 | 676 | 677 | 339 | 2-[2-(4-amidinophenyl)ethyl]-1-(2-cyclohexylethyl)-benzimidazol-5-yl-carboxylic acid-N-[4-(amino-methyl)-benzyl]-N-(2-naphthylmethyl)-amide |
| 234 | | 620 | 621 | 303 | 2-[2-(4-amidinophenyl)ethyl]-1-cyclopropylmethyl-benzimidazol-5-yl-carboxylic acid-N-[4-(amino-methyl)-benzyl]-N-(2-naphthylmethyl)-amide |
| 235 | | 670 | — | — | 2-[2-(4-amidinophenyl)ethyl]-1-(2-phenylethyl)-benzimidazol-5-yl-carboxylic acid-N-[4-(amino-methyl)-benzyl]-N-(2-naphthylmethyl)-amide |

TABLE 11-continued

Compounds of general formula (I) according to the invention wherein the following definitions apply:

—R²: —C(=NH)NH₂; —R³: 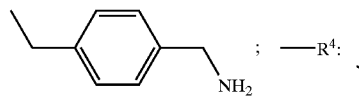 ; —R⁴: 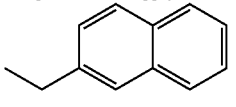

| Ex. | —R¹ | calc. [M] | found* | found# | Chemical name |
|---|---|---|---|---|---|
| 236 | 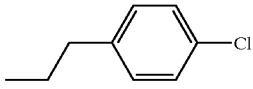 | 704 | — | 353 | 2-[2-(4-amidinophenyl)ethyl]-1-[2-(4-chlorophenyl)ethyl]-benzimidazol-5-yl-carboxylic acid-N-[4-(amino-methyl)-benzyl]-N-(2-naphthylmethyl)-amide |
| 237 | 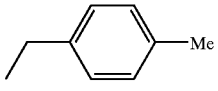 | 670 | 671 | 328 | 2-[2-(4-amidinophenyl)ethyl]-1-(4-methylbenzyl)-benzimidazol-5-yl-carboxylic acid-N-[4-(amino-methyl)-benzyl]-N-(2-naphthylmethyl)-amide |
| 238 | 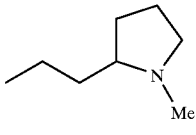 | 677 | 678 | 389 | 2-[2-(4-amidinophenyl)ethyl]-1-[2-(1-methylpyrrolidin-2-yl)-ethyl]-benzimidazol-5-yl-carboxylic acid-N-[4-(amino-methyl)-benzyl]-N-(2-naphthylmethyl)-amide |
| 239 | 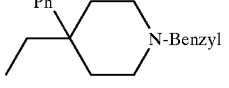 | 829 | — | 416 | 2-[2-(4-amidinophenyl)ethyl]-1-[(1-benzyl-4-phenyl-piperidin-4-yl)-methyl]-benzimidazol-5-yl-carboxylic acid-N-[4-(amino-methyl)-benzyl]-N-(2-naphthylmethyl)-amide |
| 240 | 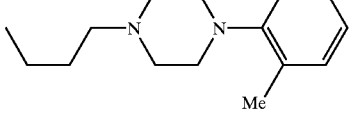 | 782 | 783 | 391 | 2-[2-(4-amidinophenyl)ethyl]-1-{3-[4-(2-methylphenyl)-piperazin-1-yl]-propyl}-benzimidazol-5-yl-carboxylic acid-N-[4-(amino-methyl)-benzyl]-N-(2-naphthylmethyl)-amide |
| 241 | 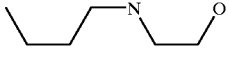 | 693 | — | 347 | 2-[2-(4-amidinophenyl)ethyl]-1-[3-(morpholin-4-yl)-propyl]-benzimidazol-5-yl-carboxylic acid-N-[4-(amino-methyl)-benzyl]-N-(2-naphthylmethyl)-amide |
| 242 | 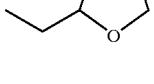 | 650 | — | — | 2-[2-(4-amidinophenyl)ethyl]-1-(tetrahydrofuran-2-yl-methyl)-benzimidazol-5-yl-carboxylic acid-N-[4-(amino-methyl)-benzyl]-N-(2-naphthylmethyl)-amide |
| 243 | 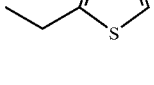 | 662 | — | — | 2-[2-(4-amidinophenyl)ethyl]-1-(2-thiophenyl-methyl)-benzimidazol-5-yl-carboxylic acid-N-[4-(amino-methyl)-benzyl]-N-(2-naphthylmethyl)-amide |
| 244 | 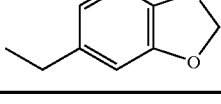 | 700 | — | — | 2-[2-(4-amidinophenyl)ethyl]-1-(1,3-benzodioxol-5-yl-methyl)-benzimidazol-5-yl-carboxylic acid-N-[4-(amino-methyl)-benzyl]-N-(2-naphthylmethyl)-amide |

*[M + H]⁺;
[M + 2H]²⁺

TABLE 12

Compounds of general formula (I) according to the invention wherein the following definitions apply:

—R²: —C(=NH)NH₂; —R³:  ; —R⁴: 

| Ex. | —R¹ | calc. [M] | found* | found# | Chemical name |
|---|---|---|---|---|---|
| 245 | n-decyl- | 638 | 639 | 320 | 2-[2-(4-amidinophenyl)ethyl]-1-n-decyl-benzimidazol-5-yl-carboxylic acid-N-(2-aminoethyl)-N-[4-(methoxycarbonyl)-benzyl]-amide |
| 246 |  | 584 | 585 | 293 | 2-[2-(4-amidinophenyl)ethyl]-1-(3-ethoxypropyl)-benzimidazol-5-yl-carboxylic acid-N-(2-aminoethyl)-N-[4-(methoxycarbonyl)-benzyl]-amide |
| 247 |  | 667 | 668 | 334 | 2-[2-(4-amidinophenyl)ethyl]-1-(3-di-n-butylaminopropyl)-benzimidazol-5-yl-carboxylic acid-N-(2-aminoethyl)-N-[4-(methoxycarbonyl)-benzyl]-amide |
| 248 |  | 673 | 674 | 337 | 2-[2-(4-amidinophenyl)ethyl]-1-[3-(benzylcarbonylamino)-propyl]-benzimidazol-5-yl-carboxylic acid-N-(2-aminoethyl)-N-[4-(methoxycarbonyl)-benzyl]-amide |
| 249 |  | 608 | 609 | 305 | 2-[2-(4-amidinophenyl)ethyl]-1-(2-cyclohexylethyl)-benzimidazol-5-yl-carboxylic acid-N-(2-aminoethyl)-N-[4-(methoxycarbonyl)-benzyl]-amide |
| 250 |  | 552 | 553 | 277 | 2-[2-(4-amidinophenyl)ethyl]-1-cyclopropylmethyl-benzimidazol-5-yl-carboxylic acid-N-(2-aminoethyl)-N-[4-(methoxycarbonyl)-benzyl]-amide |
| 251 |  | 602 | 603 | 302 | 2-[2-(4-amidinophenyl)ethyl]-1-(2-phenylethyl)-benzimidazol-5-yl-carboxylic acid-N-(2-aminoethyl)-N-[4-(methoxycarbonyl)-benzyl]-amide |
| 252 |  | 636 | 637 | 319 | 2-[2-(4-amidinophenyl)ethyl]-1-[2-(4-chlorophenyl)ethyl]-benzimidazol-5-yl-carboxylic acid-N-(2-aminoethyl)-N-[4-(methoxycarbonyl)-benzyl]-amide |
| 253 |  | 602 | 603 | 302 | 2-[2-(4-amidinophenyl)ethyl]-1-(4-methylbenzyl)-benzimidazol-5-yl-carboxylic acid-N-(2-aminoethyl)-N-[4-(methoxycarbonyl)-benzyl]-amide |
| 254 |  | 609 | 610 | 305 | 2-[2-(4-amidinophenyl)ethyl]-1-[2-(1-methylpyrrolidin-2-yl)-ethyl]-benzimidazol-5-yl-carboxylic acid-N-(2-aminoethyl)-N-[4-(methoxycarbonyl)-benzyl]-amide |
| 255 |  | 761 | — | 381 | 2-[2-(4-amidinophenyl)ethyl]-1-[(1-benzyl-4-phenyl-piperidin-4-yl)-methyl]-benzimidazol-5-yl-carboxylic acid-N-(2-aminoethyl)-N-[4-(methoxycarbonyl)-benzyl]-amide |

TABLE 12-continued

Compounds of general formula (I) according to the invention wherein the following definitions apply:

—R²: —C(=NH)NH₂; —R³: —CH₂CH₂NH₂ ; —R⁴: —CH₂-C₆H₄-C(=O)OMe

| Ex. | —R¹ | calc. [M] | found* | found# | Chemical name |
|---|---|---|---|---|---|
| 256 | 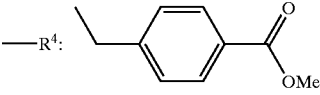 | 714 | 715 | 358 | 2-[2-(4-amidinophenyl)ethyl]-1-{3-[4-(2-methylphenyl)-piperazin-1-yl]-propyl}-benzimidazol-5-yl-carboxylic acid-N-(2-aminoethyl)-N-[4-(methoxycarbonyl)-benzyl]-amide |
| 257 | 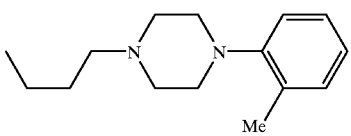 | 625 | 626 | 313 | 2-[2-(4-amidinophenyl)ethyl]-1-[3-(morpholin-4-yl)-propyl]-benzimidazol-5-yl-carboxylic acid-N-(2-aminoethyl)-N-[4-(methoxycarbonyl)-benzyl]-amide |
| 258 | 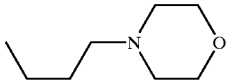 | 582 | 583 | 292 | 2-[2-(4-amidinophenyl)ethyl]-1-(tetrahydrofuran-2-yl-methyl)-benzimidazol-5-yl-carboxylic acid-N-(2-aminoethyl)-N-[4-(methoxycarbonyl)-benzyl]-amide |
| 259 | 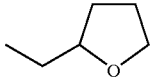 | 594 | 595 | 298 | 2-[2-(4-amidinophenyl)ethyl]-1-(2-thiophenyl-methyl)-benzimidazol-5-yl-carboxylic acid-N-(2-aminoethyl)-N-[4-(methoxycarbonyl)-benzyl]-amide |
| 260 | 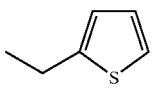 | 632 | 633 | 317 | 2-[2-(4-amidinophenyl)ethyl]-1-(1,3-benzodioxol-5-yl-methyl)-benzimidazol-5-yl-carboxylic acid-N-(2-aminoethyl)-N-[4-(methoxycarbonyl)-benzyl]-amide |

*[M + H]⁺;
[M + 2H]²⁺

TABLE 13

Compounds of general formula (I) according to the invention wherein the following definitions apply:

—R²: —C(=NH)NH₂; —R³: —CH₂CH₂NH₂; —R⁴: —CH₂-C₆H₄-OMe (3-methoxybenzyl)

| Ex. | —R¹ | calc. [M] | found* | found# | Chemical name |
|---|---|---|---|---|---|
| 261 | n-decyl- | 610 | 611 | 306 | 2-[2-(4-amidinophenyl)ethyl]-1-n-decyl-benzimidazol-5-yl-carboxylic acid-N-(2-aminoethyl)-N-(3-methoxybenzyl)-amide |
| 262 | 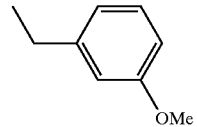 —OEt | 556 | 557 | 279 | 2-[2-(4-amidinophenyl)ethyl]-1-(3-ethoxypropyl)-benzimidazol-5-yl-carboxylic acid-N-(2-aminoethyl)-N-(3-methoxybenzyl)-amide |
| 263 | 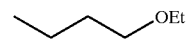 N(n-Butyl)₂ | 639 | 640 | 320 | 2-[2-(4-amidinophenyl)ethyl]-1-(3-di-n-butylaminopropyl)-benzimidazol-5-yl-carboxylic acid-N-(2-aminoethyl)-N-(3-methoxybenzyl)-amide |

TABLE 13-continued

Compounds of general formula (I) according to the invention wherein the following definitions apply:

−R²: −C(=NH)NH₂; −R³: −CH₂CH₂NH₂; −R⁴: 3-methoxy-5-ethylphenyl (OMe at one position, ethyl at other)

| Ex. | −R¹ | calc. [M] | found * | found # | Chemical name |
|---|---|---|---|---|---|
| 264 | N-butyl-N'-benzyl urea | 645 | — | 323 | 2-[2-(4-amidinophenyl)ethyl]-1-[3-(benzylcarbonylamino)-propyl]-benzimidazol-5-yl-carboxylic acid-N-(2-aminoethyl)-N-(3-methoxybenzyl)-amide |
| 265 | 2-cyclohexylethyl | 580 | 581 | 291 | 2-[2-(4-amidinophenyl)ethyl]-1-(2-cyclohexylethyl)-benzimidazol-5-yl-carboxylic acid-N-(2-aminoethyl)-N-(3-methoxybenzyl)-amide |
| 266 | cyclopropylmethyl | 524 | 525 | 263 | 2-[2-(4-amidinophenyl)ethyl]-1-cyclopropylmethyl-benzimidazol-5-yl-carboxylic acid-N-(2-aminoethyl)-N-(3-methoxybenzyl)-amide |
| 267 | 2-phenylethyl | 574 | 575 | 288 | 2-[2-(4-amidinophenyl)ethyl]-1-(2-phenylethyl)-benzimidazol-5-yl-carboxylic acid-N-(2-aminoethyl)-N-(3-methoxybenzyl)-amide |
| 268 | 2-(4-chlorophenyl)ethyl | 608 | 609 | 305 | 2-[2-(4-amidinophenyl)ethyl]-1-[2-(4-chlorophenyl)ethyl]-benzimidazol-5-yl-carboxylic acid-N-(2-aminoethyl)-N-(3-methoxybenzyl)-amide |
| 269 | 4-methylbenzyl (ethyl-linked) | 574 | 575 | 288 | 2-[2-(4-amidinophenyl)ethyl]-1-(4-methylbenzyl)-benzimidazol-5-yl-carboxylic acid-N-(2-aminoethyl)-N-(3-methoxybenzyl)-amide |
| 270 | 2-(1-methylpyrrolidin-2-yl)-ethyl | 581 | 582 | 291 | 2-[2-(4-amidinophenyl)ethyl]-1-[2-(1-methylpyrrolidin-2-yl)-ethyl]-benzimidazol-5-yl-carboxylic acid-N-(2-aminoethyl)-N-(3-methoxybenzyl)-amide |
| 271 | (1-benzyl-4-phenyl-piperidin-4-yl)-methyl | 733 | 734 | 367 | 2-[2-(4-amidinophenyl)ethyl]-1-[(1-benzyl-4-phenyl-piperidin-4-yl)-methyl]-benzimidazol-5-yl-carboxylic acid-N-(2-aminoethyl)-N-(3-methoxybenzyl)-amide |
| 272 | 3-[4-(2-methylphenyl)-piperazin-1-yl]-propyl | 686 | 687 | 344 | 2-[2-(4-amidinophenyl)ethyl]-1-{3-[4-(2-methylphenyl)-piperazin-1-yl]-propyl}-benzimidazol-5-yl-carboxylic acid-N-(2-aminoethyl)-N-(3-methoxybenzyl)-amide |
| 273 | 3-(morpholin-4-yl)-propyl | 597 | 598 | 299 | 2-[2-(4-amidinophenyl)ethyl]-1-[3-(morpholin-4-yl)-propyl]-benzimidazol-5-yl-carboxylic acid-N-(2-aminoethyl)-N-(3-methoxybenzyl)-amide |
| 274 | (tetrahydrofuran-2-yl)-methyl | 554 | 555 | 278 | 2-[2-(4-amidinophenyl)ethyl]-1-(tetrahydrofuran-2-yl-methyl)-benzimidazol-5-yl-carboxylic acid-N-(2-aminoethyl)-N-(3-methoxybenzyl)-amide |

TABLE 13-continued

Compounds of general formula (I) according to the invention wherein the following definitions apply:

–R²: –C(=NH)NH₂;   –R³: –CH₂CH₂CH₂NH₂;   –R⁴: 3-methoxy-(ethylphenyl) (with OMe)

| Ex. | –R¹ | calc. [M] | found * | found # | Chemical name |
|---|---|---|---|---|---|
| 275 | 2-ethyl-thiophene | 566 | 567 | 284 | 2-[2-(4-amidinophenyl)ethyl]-1-(2-thiophenyl-methyl)-benzimidazol-5-yl-carboxylic acid-N-(2-aminoethyl)-N-(3-methoxybenzyl)-amide |
| 276 | 5-ethyl-1,3-benzodioxole | 604 | 605 | 303 | 2-[2-(4-amidinophenyl)ethyl]-1-(1,3-benzodioxol-5-yl-methyl)-benzimidazol-5-yl-carboxylic acid-N-(2-aminoethyl)-N-(3-methoxybenzyl)-amide |

*[M + H]⁺; #[M + 2H]²⁻

TABLE 14

Compounds of general formula (I) according to the invention wherein the following definitions apply:

–R²: –C(=NH)NH₂;   –R³: –CH₂CH₂CH₂NH₂;   –R⁴: n-butyl

| Ex. | –R¹ | calc. [M] | found * | found # | Chemical name |
|---|---|---|---|---|---|
| 277 | n-decyl- | 546 | — | 274 | 2-[2-(4-amidinophenyl)ethyl]-1-n-decyl-benzimidazol-5-yl-carboxylic acid-N-(2-aminoethyl)-N-n-butyl-amide |
| 278 | –CH₂CH₂CH₂OEt | 492 | — | 247 | 2-[2-(4-amidinophenyl)ethyl]-1-(3-ethoxypropyl)-benzimidazol-5-yl-carboxylic acid-N-(2-aminoethyl)-N n-butyl-amide |
| 279 | –CH₂CH₂CH₂N(n-Butyl)₂ | 575 | — | 288 | 2-[2-(4-amidinophenyl)ethyl]-1-(3-di-n-butylaminopropyl)-benzimidazol-5-yl-carboxylic acid-N-(2-aminoethyl)-N-n-butyl-amide |
| 280 | –CH₂CH₂CH₂CH₂–NH–C(=O)–Benzyl | 581 | — | — | 2-[2-(4-amidinophenyl)ethyl]-1-[3-(benzylcarbonylamino)-propyl]-benzimidazol-5-yl-carboxylic acid-N-(2-aminoethyl)-N-n-butyl-amide |
| 281 | 2-cyclohexylethyl | 516 | — | — | 2-[2-(4-amidinophenyl)ethyl]-1-(2-cyclohexylethyl)-benzimidazol-5-yl-carboxylic acid-N-(2-aminoethyl)-N n-butyl-amide |
| 282 | cyclopropylmethyl | 460 | 461 | 231 | 2-[2-(4-amidinophenyl)ethyl]-1-cyclopropylmethyl-benzimidazol-5-yl-carboxylic acid-N-(2-aminoethyl)-N-n-butyl-amide |

TABLE 14-continued

Compounds of general formula (I) according to the invention wherein the following definitions apply:

−R²: −C(=NH)NH₂;   −R³: −CH₂CH₂−NH₂;   −R⁴: n-butyl

| Ex. | −R¹ | calc. [M] | found * | found # | Chemical name |
|---|---|---|---|---|---|
| 283 | (2-phenylethyl) | 510 | — | 256 | 2-[2-(4-amidinophenyl)ethyl)-1-(2-phenylethyl)-benzimidazol-5-yl-carboxylic acid-N-(2-aminoethyl)-N-n-butyl-amide |
| 284 | 2-(4-chlorophenyl)ethyl | 545 | — | 272 | 2-[2-(4-amidinophenyl)ethyl]-1-[2-(4-chlorophenyl)ethyl]-benzimidazol-5-yl-carboxylic acid-N-(2-aminoethyl)-N-n-butyl-amide |
| 285 | 2-(4-methylphenyl)ethyl | 510 | — | 255 | 2-[2-(4-amidinophenyl)ethyl)-1-(4-methylbenzyl)-benzimidazol-5-yl-carboxylic acid-N-(2-aminoethyl)-N-n-butyl-amide |
| 286 | 2-(1-methylpyrrolidin-2-yl)ethyl | 517 | — | 259 | 2-[2-(4-amidinophenyl)ethyl]-1-[2-(1-methylpyrrolidin-2-yl)-ethyl]-benzimidazol-5-yl-carboxylic acid-N-(2-aminoethyl)-N-n-butyl-amide |
| 287 | (1-benzyl-4-phenyl-piperidin-4-yl)methyl | 669 | — | 335 | 2-[2-(4-amidinophenyl)ethyl]-1-[(1-benzyl-4-phenyl-piperidin-4-yl)-methyl]-benzimidazol-5-yl-carboxylic acid-N-(2-aminoethyl)-N-n-butyl-amide |
| 288 | 3-[4-(2-methylphenyl)-piperazin-1-yl]propyl | 622 | — | 312 | 2-[2-(4-amidinophenyl)ethyl]-1-{3-[4-(2-methylphenyl)-piperazin-1-yl]-propyl}-benzimidazol-5-yl-carboxylic acid-N-(2-aminoethyl)-N-n-butyl-amide |
| 289 | 3-(morpholin-4-yl)propyl | 533 | — | 268 | 2-[2-(4-amidinophenyl)ethyl]-1-[3-(morpholin-4-yl)-propyl]-benzimidazol-5-yl-carboxylic acid-N-(2-aminoethyl)-N-n-butyl-amide |
| 290 | (tetrahydrofuran-2-yl)methyl | 490 | 491 | 246 | 2-[2-(4-amidinophenyl)ethyl]-1-(tetrahydrofuran-2-yl-methyl)-benzimidazol-5-yl-carboxylic acid-N-(2-aminoethyl)-N-n-butyl-amide |
| 291 | (2-thiophenyl)methyl | 502 | — | 252 | 2-[2-(4-amidinophenyl)ethyl]-1-(2-thiophenyl-methyl)-benzimidazol-5-ylcarboxylic acid-N-(2-aminoethyl)-N-n-butyl-amide |
| 292 | (1,3-benzodioxol-5-yl)methyl | 540 | — | 271 | 2-[2-(4-amidinophenyl)ethyl]-1-(1,3-benzodioxol-5-yl-methyl)-benzimidazol-5-yl-carboxylic acid-N(2-aminoethyl)-N-n-butyl-amide |

* [M + H]⁺; # [M + 2H]²⁺

TABLE 15

Compounds of general formula (I) according to the invention wherein the following definitions apply:

$-R^2$: $-C(=NH)NH_2$;  $-R^3$: $-CH_2CH_2-NH_2$;  $-R^4$: $-CH_2-C_6H_5$ (benzyl)

| Ex. | $-R^1$ | calc. [M] | found * | found # | Chemical name |
|---|---|---|---|---|---|
| 293 | n-decyl- | 580 | 581 | 291 | 2-[2-(4-amidinophenyl)ethyl]-1-n-decyl-benzimidazol-5-yl-carboxylic acid-N-(2-aminoethyl)-N-benzyl-amide |
| 294 | propyl-OEt | 526 | 527 | 264 | 2-[2-(4-amidinophenyl)ethyl]-1-(3-ethoxypropyl)-benzimidazol-5-yl-carboxylic acid-N-(2-aminoethyl)-N-benzyl-amide |
| 295 | propyl-N(n-Butyl)$_2$ | 609 | 610 | 305 | 2-[2-(4-amidinophenyl)ethyl]-1-(3-di-n-butylaminopropyl)-benzimidazol-5-yl-carboxylic acid-N-(2-aminoethyl)-N-benzyl-amide |
| 296 | propyl-NH-C(=O)-Benzyl | 615 | — | 308 | 2-[2-(4-amidinophenyl)ethyl]-1-[3-(benzylcarbonylamino)-propyl]-benzimidazol-5-yl-carboxylic acid-N-(2-aminoethyl)-N-benzyl-amide |
| 297 | ethyl-cyclohexyl | 550 | 551 | 276 | 2-[2-(4-amidinophenyl)ethyl]-1-(2-cyclohexylethyl)-benzimidazol-5-yl-carboxylic acid-N-(2-aminoethyl)-N-benzyl-amide |
| 298 | methyl-cyclopropyl | 494 | 495 | 248 | 2-[2-(4-amidinophenyl)ethyl]-1-cyclopropylmethyl-benzimidazol-5-yl-carboxylic acid-N-(2-aminoethyl)-N-benzyl-amide |
| 299 | ethyl-phenyl | 544 | 545 | 273 | 2-[2-(4-amidinopheny1)ethyl]-1-(2-phenylethyl)-benzimidazol-5-yl-carboxylic acid-N-(2-aminoethyl)-N-benzyl-amide |
| 300 | ethyl-(4-Cl-phenyl) | 578 | 579 | 290 | 2-[2-(4-amidinophenyl)ethyl]-1-[2-(4-chlorophenyl)ethyl]-benzimidazol-5-yl-carboxylic acid-N-(2-aminoethyl)-N-benzyl-amide |
| 301 | methyl-(4-Me-phenyl) | 544 | 545 | 273 | 2-[2-(4-amidinophenyl)ethyl]-1-(4-methylbenzyl)-benzimidazol-5-yl-carboxylic acid-N-(2-aminoethyl)-N-benzyl-amide |
| 302 | ethyl-(1-methylpyrrolidin-2-yl) | 551 | 552 | 276 | 2-[2-(4-amidinophenyl)ethyl]-1-[2-(1-methylpyrrolidin-2-yl)-ethyl]-benzimidazol-5-yl-carboxylic acid-N-(2-aminoethyl)-N-benzyl-amide |
| 303 | (1-benzyl-4-phenyl-piperidin-4-yl)-methyl | 703 | — | 352 | 2-[2-(4-amidinophenyl)ethyl]-1-[(1-benzyl-4-phenyl-piperidin-4-yl)-methyl]-benzimidazol-5-yl-carboxylic acid-N-(2-aminoethyl)-N-benzyl-amide |
| 304 | propyl-[4-(2-methylphenyl)-piperazin-1-yl] | 656 | 657 | 329 | 2-[2-(4-amidinophenyl)ethyl]-1-{3-[4-(2-methylphenyl)-piperazin-1-yl]-propyl}-benzimidazol-5-yl-carboxylic acid-N-(2-aminoethyl)-N-benzyl-amide |
| 305 | propyl-morpholin-4-yl | 567 | 568 | 284 | 2-[2-(4-amidinophenyl)ethyl]-1-[3-(morpholin-4-yl)-propyl]-benzimidazol-5-yl-carboxylic acid-N-(2-aminoethyl)-N-benzyl-amide |

TABLE 15-continued

Compounds of general formula (I) according to the invention wherein the following definitions apply:

−R²: —C(=NH)NH₂; −R³: ⁓⁓NH₂; −R⁴: benzyl (CH₂-phenyl)

| Ex. | −R¹ | calc. [M] | found * | found # | Chemical name |
|---|---|---|---|---|---|
| 306 | (tetrahydrofuran-2-yl-methyl) | 524 | 525 | 263 | 2-[2-(4-amidinophenyl)ethyl]-1-(tetrahydrofuran-2-yl-methyl)-benzimidazol-5-yl-carboxylic acid-N-(2-aminoethyl)-N-benzyl-amide |
| 307 | (2-thiophenyl-methyl) | 536 | 537 | 269 | 2-[2-(4-amidinophenyl)ethyl]-1-(2-thiophenyl-methyl)-benzimidazol-5-yl-carboxylic acid-N-(2-aminoethyl)-N-benzyl-amide |
| 308 | (1,3-benzodioxol-5-yl-methyl) | 574 | 575 | 288 | 2-[2-(4-amidinophenyl)ethyl]-1-(1,3-benzodioxol-5-yl-methyl)-benzimidazol-5-yl-carboxylic acid-N-(2-aminoethyl)-N-benzyl-amide |

*[M + H]⁺; #[M + 2H]²⁺

25

TABLE 16

Compounds of general formula (I) according to the invention wherein the following definitions apply:

−R²: —C(=NH)NH₂; −R³: ⁓⁓NH₂; −R⁴: CH₂-(2-pyridyl)

| Ex. | −R¹ | calc. [M] | found * | found # | Chemical name |
|---|---|---|---|---|---|
| 309 | n-decyl- | 581 | 582 | 291 | 2-[2-(4-amidinophenyl)ethyl]-1-n-decyl-benzimidazol-5-yl-carboxylic acid-N-(2-aminoethyl)-N-(2-pyridyl)-amide |
| 310 | ⁓⁓OEt | 527 | 528 | 264 | 2-[2-(4-amidinophenyl)ethyl]-1-(3-ethoxypropyl)-benzimidazol-5-yl-carboxylic acid-N-(2-aminoethyl)-N(2-pyridyl)-amide |
| 311 | ⁓⁓N(n-Butyl)₂ | 610 | 611 | 306 | 2-[2-(4-amidinophenyl)ethyl]-1-(3-di-n-butylaminopropyl)-benzimidazol-5-yl-carboxylic acid-N-(2-aminoethyl)-N-(2-pyridyl)-amide |
| 312 | ⁓⁓N(H)-C(=O)-Benzyl | 616 | 617 | 309 | 2-[2-(4-amidinophenyl)ethyl]-1-[3-(benzylcarbonylamino)-propyl]-benzimidazol-5-yl-carboxylic acid-N-(2-aminoethyl)-N-(2-pyridyl)-amide |
| 313 | (2-cyclohexylethyl) | 551 | 552 | 276 | 2-[2-(4-amidinophenyl)ethyl]-1-(2-cyclohexylethyl)-benzimidazol-5-yl-carboxylic acid-N-(2-aminoethyl)-N-(2-pyridyl)-amide |
| 314 | cyclopropylmethyl | 495 | 496 | 248 | 2-[2-(4-amidinophenyl)ethyl]-1-cyclopropylmethyl-benzimidazol-5-yl-carboxylic acid-N-(2-aminoethyl)-N-(2-pyridyl)-amide |

TABLE 16-continued

Compounds of general formula (I) according to the invention wherein the following definitions apply:

$-R^2$: —C(=NH)NH₂; $-R^3$: —CH₂CH₂—NH₂; $-R^4$: 2-ethylpyridyl

| Ex. | -R¹ | calc. [M] | found * | found # | Chemical name |
|---|---|---|---|---|---|
| 315 | 2-phenylethyl | 545 | 546 | 273 | 2-[2-(4-amidinophenyl)ethyl]-1-(2-phenylethyl)-benzimidazol-5-yl-carboxylic acid-N-(2-aminoethyl)-N-(2-pyridyl)-amide |
| 316 | 2-(4-chlorophenyl)ethyl | 579 | 580 | 291 | 2-[2-(4-amidinophenyl)ethyl]-1-[2-(4-chlorophenyl)ethyl]-benzimidazol-5-yl-carboxylic acid-N-(2-aminoethyl)-N-(2-pyridyl)-amide |
| 317 | 2-(4-methylphenyl)ethyl | 545 | 546 | 273 | 2-[2-(4-amidinophenyl)ethyl]-1-(4-methylbenzyl)-benzimidazol-5-yl-carboxylic acid-N-(2-aminoethyl)-N-(2-pyridyl)-amide |
| 318 | 2-(1-methylpyrrolidin-2-yl)ethyl | 552 | 553 | 277 | 2-[2-(4-amidinophenyl)ethyl]-1-[2-(1-methylpyrrolidin-2-yl)-ethyl]-benzimidazol-5-yl-carboxylic acid-N-(2-aminoethyl)-N-(2-pyridyl)-amide |
| 319 | (1-benzyl-4-phenyl-piperidin-4-yl)methyl | 704 | — | 353 | 2-[2-(4-amidinophenyl)ethyl]-1-[(1-benzyl-4-phenyl-piperidin-4-yl)-methyl]-benzimidazol-5-yl-carboxylic acid-N-(2-aminoethyl)-N-(2-pyridyl)-amide |
| 320 | 3-[4-(2-methylphenyl)-piperazin-1-yl]propyl | 657 | 658 | 329 | 2-[2-(4-amidinophenyl)ethyl]-1-{3-[4-(2-methylphenyl)-piperazin-1-yl]-propyl}-benzimidazol-5-yl-carboxylic acid-N-(2-aminoethyl)-N-(2-pyridyl)-amide |
| 321 | 3-(morpholin-4-yl)propyl | 568 | 569 | 285 | 2-[2-(4-amidinophenyl)ethyl]-1-[3-(morpholin-4-yl)-propyl]-benzimidazol-5-yl-carboxylic acid-N-(2-aminoethyl)-N-(2-pyridyl)-amide |
| 322 | (tetrahydrofuran-2-yl)methyl | 525 | 526 | 263 | 2-[2-(4-amidinophenyl)ethyl]-1-(tetrahydrofuran-2-yl-methyl)-benzimidazol-5-yl-carboxylic acid-N-(2-aminoethyl)-N-(2-pyridyl)-amide |
| 323 | (thiophen-2-yl)methyl | 537 | 538 | 269 | 2-[2-(4-amidinophenyl)ethyl]-1-(2-thiophenyl-methyl)-benzimidazol-5-yl-carboxylic acid-N-(2-aminoethyl)-N-(2-pyridyl)-amide |
| 324 | (1,3-benzodioxol-5-yl)methyl | 575 | 576 | 288 | 2-[2-(4-amidinophenyl)ethyl]-1-(1,3-benzodioxol-5-yl-methyl)-benzimidazol-5-yl-carboxylic acid-N-(2-aminoethyl)-N-(2-pyridyl)-amide |

*[M + H]⁺; #[M + 2H]²⁺ → *$[M + H]^+$; #$[M + 2H]^{2+}$

TABLE 17

Compounds of general formula (I) according to the invention wherein the following definitions apply:

-R²: —C(=NH)NH₂;   -R³: ~~~NH₂;   -R⁴: 3-ethylpyridyl

| Ex. | -R¹ | calc. [M] | found * | found # | Chemical name |
|---|---|---|---|---|---|
| 325 | n-decyl- | 581 | 582 | 291 | 2-[2-(4-amidinophenyl)ethyl]-1-n-decyl-benzimidazol-5-yl-carboxylic acid-N-(2-aminoethyl)-N-(3-pyridyl)-amide |
| 326 | ~~~OEt | 527 | 528 | 264 | 2-[2-(4-amidinophenyl)ethyl]-1-(3-ethoxypropyl)-benzimidazol-5-yl-carboxylic acid-N-(2-aminoethyl)-N-(3-pyridyl)-amide |
| 327 | ~~~N(n-Butyl)₂ | 610 | 611 | 306 | 2-[2-(4-amidinophenyl)ethyl]-1-(3-di-n-butylaminopropyl)-benzimidazol-5-yl-carboxylic acid-N-(2-aminoethyl)-N-(3-pyridyl)-amide |
| 328 | ~~~N(H)C(O)-Benzyl | 616 | 617 | 309 | 2-[2-(4-amidinophenyl)ethyl]-1-[3-(benzylcarbonylamino)-propyl]benzimidazol-5-yl-carboxylic acid-N-(2-aminoethyl)-N-(3-pyridyl)-amide |
| 329 | ~~~cyclohexyl | 551 | 552 | 276 | 2-[2-(4-amidinophenyl)ethyl]-1-(2-cyclohexylethyl)-benzimidazol-5-yl-carboxylic acid-N-(2-aminoethyl)-N-(3-pyridyl)-amide |
| 330 | ~~~cyclopropyl | 495 | 496 | 248 | 2-[2-(4-amidinophenyl)ethyl]-1-cyclopropylmethyl-benzimidazol-5-yl-carboxylic acid-N-(2-aminoethyl)-N-(3-pyridyl)-amide |
| 331 | ~~~phenyl | 545 | 546 | 273 | 2-[2-(4-amidinophenyl)ethyl]-1-(2-phenylethyl)-benzimidazol-5-yl-carboxylic acid-N-(2-aminoethyl)-N-(3-pyridyl)-amide |
| 332 | ~~~(4-chlorophenyl) | 579 | 580 | 291 | 2-[2-(4-amidinophenyl)ethyl]-1-[2-(4-chlorophenyl)ethyl]-benzimidazol-5-yl-carboxylic acid-N-(2-aminoethyl)-N-(3-pyridyl)-amide |
| 333 | ~~~(4-methylphenyl) | 545 | 546 | 273 | 2-[2-(4-amidinophenyl)ethyl]-1-(4-methylbenzyl)-benzimidazol-5-yl-carboxylic acid-N-(2-aminoethyl)-N-(3-pyridyl)-amide |
| 334 | ~~~(1-methylpyrrolidin-2-yl) | 552 | 553 | 277 | 2-[2-(4-amidinophenyl)ethyl]-1-[2-(1-methylpyrrolidin-2-yl)-ethyl]-benzimidazol-5-yl-carboxylic acid-N-(2-aminoethyl)-N-(3-pyridyl)-amide |
| 335 | Ph/Et-piperidin-4-yl-CH₂-N-Benzyl | 704 | — | 353 | 2-[2-(4-amidinophenyl)ethyl]-1-[(1-benzyl-4-phenyl-piperidin-4-yl)-methyl]-benzimidazol-5-yl-carboxylic acid-N-(2-aminoethyl)-N-(3-pyridyl)-amide |
| 336 | ~~~N(piperazinyl)-(2-methylphenyl) | 657 | 658 | 329 | 2-[2-(4-amidinophenyl)ethyl]-1-{3-[4-(2-methylphenyl)-piperazin-1-yl]-propyl}-benzimidazol-5-yl-carboxylic acid-N-(2-aminoethyl)-N-(3-pyridyl)-amide |

TABLE 17-continued

Compounds of general formula (I) according to the invention wherein the following definitions apply:

−R²: —C(=NH)NH₂; −R³: ─/─/─NH₂; −R⁴: 3-ethyl-pyridine

| Ex. | −R¹ | calc. [M] | found * | found # | Chemical name |
|---|---|---|---|---|---|
| 337 | propyl-morpholine | 568 | 569 | 285 | 2-[2-(4-amidinophenyl)ethyl]-1-[3-(morpholin-4-yl)-propyl]-benzimidazol-5-yl-carboxylic acid-N-(2-aminoethyl)-N-(3-pyridyl)-amide |
| 338 | (tetrahydrofuran-2-yl)methyl | 525 | 526 | 263 | 2-[2-(4-amidinophenyl)ethyl]-1-(tetrahydrofuran-2-yl-methyl)-benzimidazol-5-yl-carboxylic acid-N-(2-aminoethyl)-N-(3-pyridyl)-amide |
| 339 | 2-thiophenyl-methyl | 537 | 538 | 269 | 2-[2-(4-amidinophenyl)ethyl]-1-(2-thiophenyl-methyl)-benzimidazol-5-yl-carboxylic acid-N-(2-aminoethyl)-N-(3-pyridyl)-amide |
| 340 | 1,3-benzodioxol-5-yl-methyl | 575 | 576 | 288 | 2-[2-(4-amidinophenyl)ethyl]-1-(1,3-benzodioxol-5-yl-methyl)-benzimidazol-5-yl-carboxylic acid-N-(2-aminoethyl)-N-(3-pyridyl)-amide |

*[M + H]⁺; #[M + 2H]²⁺

TABLE 18

Compounds of general formula (I) according to the invention wherein the following definitions apply:

−R²: —C(=NH)NH₂; −R³: ─/─/─NH₂; −R⁴: cyclohexylmethyl

| Ex. | −R¹ | calc. [M] | found * | found # | Chemical name |
|---|---|---|---|---|---|
| 341 | n-decyl- | 586 | 587 | 294 | 2-[2-(4-amidinophenyl)ethyl]-1-n-decyl-benzimidazol-5-yl-carboxylic acid-N-(2-aminoethyl)-N-cyclohexylmethyl-amide |
| 342 | ─/─/─OEt | 532 | 533 | 267 | 2-[2-(4-amidinophenyl)ethyl]-1-(3-ethoxypropyl)-benzimidazol-5-yl-carboxylic acid-N-(2-aminoethyl)-N-cyclohexylmethyl-amide |
| 343 | ─/─/─N(n-Butyl)₂ | 615 | 616 | 308 | 2-[2-(4-amidinophenyl)ethyl]-1-(3-di-n-butylaminopropyl)-benzimidazol-5-yl-carboxylic acid-N-(2-aminoethyl)-N-cyclohexylmethyl-amide |
| 344 | ─/─/─NH—C(=O)—Benzyl | 621 | 622 | 311 | 2-[2-(4-amidinophenyl)ethyl]-1-[3-(benzylcarbonylamino)-propyl]-benzimidazol-5-yl-carboxylic acid-N-(2-aminoethyl)-N-cyclohexylmethyl-amide |
| 345 | 2-cyclohexylethyl | 556 | 557 | 279 | 2-[2-(4-amidinophenyl)ethyl]-1-(2-cyclohexylethyl)-benzimidazol-5-yl-carboxylic acid-N-(2-aminoethyl)-N-cyclohexylmethyl-amide |

TABLE 18-continued

Compounds of general formula (I) according to the invention wherein the following definitions apply:

–R²: —C(=NH)NH₂; –R³: ⁀NH₂ ; –R⁴: (cyclohexylmethyl)

| Ex. | –R¹ | calc. [M] | found * [M+H]⁺ | found # [M+2H]²⁺ | Chemical name |
|---|---|---|---|---|---|
| 346 | cyclopropylmethyl-ethyl | 500 | 501 | 251 | 2-[2-(4-amidinophenyl)ethyl]-1-cyclopropylmethyl-benzimidazol-5-yl-carboxylic acid-N-(2-aminoethyl)-N-cyclohexylmethyl-amide |
| 347 | phenylethyl | 550 | 551 | 276 | 2-[2-(4-amidinophenyl)ethyl]-1-(2-phenylethyl)-benzimidazol-5-yl-carboxylic acid-N-(2-aminoethyl)-N-cyclohexylmethyl-amide |
| 348 | 4-chlorophenylethyl | 584 | 585 | 293 | 2-[2-(4-amidinophenyl)ethyl]-1-[2-(4-chlorophenyl)ethyl]-benzimidazol-5-yl-carboxylic acid-N-(2-aminoethyl)-N-cyclohexylmethyl-amide |
| 349 | 4-methylbenzyl | 550 | 551 | 276 | 2-[2-(4-amidinophenyl)ethyl]-1-(4-methylbenzyl)-benzimidazol-5-yl-carboxylic acid-N-(2-aminoethyl)-N-cyclohexylmethyl-amide |
| 350 | 1-methylpyrrolidin-2-yl-ethyl | 557 | 558 | 279 | 2-[2-(4-amidinophenyl)ethyl]-1-[2-(1-methylpyrrolidin-2-yl)-ethyl]-benzimidazol-5-yl-carboxylic acid-N-(2-aminoethyl)-N-cyclohexylmethyl-amide |
| 351 | 1-benzyl-4-phenyl-piperidin-4-yl-methyl | 708 | — | 355 | 2-[2-(4-amidinophenyl)ethyl]-1-[(1-benzyl-4-phenyl-piperidin-4-yl)-methyl]-benzimidazol-5-yl-carboxylic acid-N-(2-aminoethyl)-N-cyclohexylmethyl-amide |
| 352 | 3-[4-(2-methylphenyl)-piperazin-1-yl]-propyl | 662 | 663 | 332 | 2-[2-(4-amidinophenyl)ethyl]-1-{3-[4-(2-methylphenyl)-piperazin-1-yl]-propyl}-benzimidazol-5-yl-carboxylic acid-N-(2-aminoethyl)-N-cyclohexylmethyl-amide |
| 353 | 3-(morpholin-4-yl)-propyl | 573 | 574 | 287 | 2-[2-(4-amidinophenyl)ethyl]-1-[3-(morpholin-4-yl)-propyl]-benzimidazol-5-yl-carboxylic acid-N-(2-aminoethyl)-N-cyclohexylmethyl-amide |
| 354 | tetrahydrofuran-2-yl-methyl | 530 | 531 | 266 | 2-[2-(4-amidinophenyl)ethyl]-1-(tetrahydrofuran-2-yl-methyl)-benzimidazol-5-yl-carboxylic acid-N-(2-aminoethyl)-N-cyclohexylmethyl-amide |
| 355 | 2-thiophenyl-methyl | 542 | 543 | 272 | 2-[2-(4-amidinophenyl)ethyl]-1-(2-thiophenyl-methyl)-benzimidazol-5-yl-carboxylic acid-N-(2-aminoethyl)-N-cyclohexylmethyl-amide |
| 356 | 1,3-benzodioxol-5-yl-methyl | 580 | 581 | 291 | 2-[2-(4-amidinophenyl)ethyl]-1-(1,3-benzodioxol-5-yl-methyl)-benzimidazol-5-yl-carboxylic acid-N-(2-aminoethyl)-N-cyclohexylmethyl-amide |

*[M + H]⁺; #[M + 2H]²⁺

TABLE 19

Compounds of general formula (I) according to the invention wherein the following definitions apply:

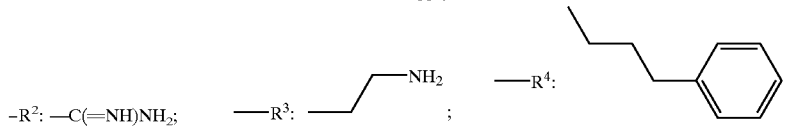

−R²: —C(=NH)NH₂;  —R³: ~~~NH₂ ;  —R⁴: (3-phenylpropyl)

| Ex. | −R¹ | calc. [M] | found * | found # | Chemical name |
|---|---|---|---|---|---|
| 357 | n-decyl | 608 | — | 305 | 2-[2-(4-amidinophenyl)ethyl]-1-n-decyl-benzimidazol-5-yl-carboxylic acid-N-(2-aminoethyl)-N-(3-phenylpropyl)-amide |
| 358 | ~~~OEt | 554 | — | 278 | 2-[2-(4-amidinophenyl)ethyl]-1-(3-ethoxypropyl)-benzimidazol-5-yl-carboxylic acid-N-(2-aminoethyl)-N-(3-phenylpropyl)-amide |
| 359 | ~~~N(n-Butyl)₂ | 637 | — | 319 | 2-[2-(4-amidinophenyl)ethyl]-1-(3-di-n-butylaminopropyl)-benzimidazol-5-yl-carboxylic acid-N-(2-aminoethyl)-N-(3-phenylpropyl)-amide |
| 360 | ~~~N(H)C(=O)Benzyl | 643 | — | 322 | 2-[2-(4-amidinophenyl)ethyl]-1-[3-(benzylcarbonylamino)-propyl]-benzimidazol-5-yl-carboxylic acid-N-(2-aminoethyl)-N-(3-phenylpropyl)-amide |
| 361 | ethyl-cyclohexyl | 578 | — | 290 | 2-[2-(4-amidinophenyl)ethyl]-1-(2-cyclohexylethyl)-benzirnidazol-5-yl-carboxylic acid-N-(2-aminoethyl)-N-(3-phenylpropyl)-amide |
| 362 | methyl-cyclopropyl | 522 | — | 262 | 2-[2-(4-amidinophenyl)ethyl]-1-cyclopropylmethyl-benzimidazol-5-yl-carboxylic acid-N-(2-aminoethyl)-N-(3-phenylpropyl)-amide |
| 363 | ethyl-phenyl | 572 | — | 287 | 2-[2-(4-amidinophenyl)ethyl]-1-(2-phenylethyl)-benzimidazol-5-yl-carboxylic acid-N-(2-arninoethyl)-N-(3-phenylpropyl)-amide |
| 364 | ethyl-(4-Cl-phenyl) | 606 | 607 | 304 | 2-[2-(4-amidinophenyl)ethyl]-1-[2-(4-chlorophenyl)ethyl]-benzimidazol-5-yl-carboxylic acid-N-(2-aminoethyl)-N-(3-phenylpropyl)-amide |
| 365 | methyl-(4-Me-phenyl) | 572 | — | 287 | 2-[2-(4-amidinophenyl)ethyl]-1-(4-methylbenzyl)-benzimidazol-5-yl-carboxylic acid-N-(2-aminoethyl)-N-(3-phenylpropyl)-amide |
| 366 | ethyl-(1-methyl-pyrrolidin-2-yl) | 579 | — | 290 | 2-[2-(4-amidinophenyl)ethyl]-1-[2-(1-methyl-pyrrolidin-2-yl)-ethyl]-benzimidazol-5-yl-carboxylic acid-N-(2-aminoethyl)-N-(3-phenylpropyl)-amide |
| 367 | (1-benzyl-4-phenyl-piperidin-4-yl)methyl | 731 | — | 366 | 2-[2-(4-amidinophenyl)ethyl]-1-[(1-benzyl-4-phenyl-piperidin-4-yl)-methyl]-benzimidazol-5-yl-carboxylic acid-N-(2-aminoethyl)-N-(3-phenylpropyl)-amide |

TABLE 19-continued

Compounds of general formula (I) according to the invention wherein the following definitions apply:

$-R^2$: $-C(=NH)NH_2$;  $-R^3$: $\diagup\!\!\!\diagdown\!\!\!\diagup NH_2$ ;  $-R^4$: 3-phenylpropyl

| Ex. | $-R^1$ | calc. [M] | found * | found # | Chemical name |
|---|---|---|---|---|---|
| 368 | 3-[4-(2-methylphenyl)-piperazin-1-yl]-propyl | 643 | 644 | 323 | 2-[2-(4-amidinophenyl)ethyl]-1-{3-[4-(2-methylphenyl)-piperazin-1-yl]-propyl}-benzimidazol-5-yl-carboxylic acid-N-(2-aminoethyl)-N-(3-phenylpropyl)-amide |
| 369 | 3-(morpholin-4-yl)-propyl | 595 | — | 298 | 2-[2-(4-amidinophenyl)ethyl]-1-[3-(morpholin-4-yl)-propyl]-benzimidazol-5-yl-carboxylic acid-N-(2-aminoethyl)-N-(3-phenylpropyl)-amide |
| 370 | (tetrahydrofuran-2-yl-methyl) | 552 | 553 | 277 | 2-[2-(4-amidinophenyl)ethyl]-1-(tetrahydrofuran-2-yl-methyl)-benzimidazol-5-yl-carboxylic acid-N-(2-aminoethyl)-N-(3-phenylpropyl)-amide |
| 371 | (2-thiophenyl-methyl) | 564 | — | 283 | 2-[2-(4-amidinophenyl)ethyl]-1-(2-thiophenyl-methyl)-benzimidazol-5-yl-carboxylic acid-N-(2-aminoethyl)-N-(3-phenylpropyl)-amide |
| 372 | (1,3-benzodioxol-5-yl-methyl) | 602 | — | 302 | 2-[2-(4-amidinophenyl)ethyl]-1-(1,3-benzodioxol-5-yl-methyl)-benzimidazol-5-yl-carboxylic acid-N-(2-aminoethyl)-N-(3-phenylpropyl)-amide |

*[M + H]⁺; #[M + 2H]²⁺

TABLE 20

Compounds of general formula (I) according to the invention wherein the following definitions apply:

$-R^2$: $-C(=NH)NH_2$;  $-R^3$: $\diagup\!\!\!\diagdown\!\!\!\diagup NH_2$ ;  $-R^4$: 4-chlorobenzyl-ethyl

| Ex. | $-R^1$ | calc. [M] | found * | found # | Chemical name |
|---|---|---|---|---|---|
| 373 | n-decyl | 615 | 616 | 308 | 2-[2-(4-amidinophenyl)ethyl]-1-n-decyl-benzimidazol-5-yl-carboxylic acid-N-(2-aminoethyl)-N-(4 chlorbenzyl)-amide |
| 374 | (3-ethoxypropyl) OEt | 560 | 561 | 281 | 2-[2-(4-amidinophenyl)ethyl]-1-(3-ethoxypropyl)-benzimidazol-5-yl-carboxylic acid-N-(2-aminoethyl)-N-(4-chlorbenzyl)-amide |
| 375 | N(n-Butyl)₂ | 643 | 644 | 323 | 2-[2-(4-amidinophenyl)ethyl]-1-(3-di-n-butylaminopropyl)-benzimidazol-5-yl-carboxylic acid-N-(2-aminoethyl)-N-(4-chlorbenzyl)-amide |

TABLE 20-continued

Compounds of general formula (I) according to the invention wherein the following definitions apply:

−R²: —C(=NH)NH₂;  −R³: —CH₂CH₂NH₂;  —R⁴: —CH₂-(4-chlorophenyl)

| Ex. | −R¹ | calc. [M] | found * | found # | Chemical name |
|---|---|---|---|---|---|
| 376 | butyl-N(H)-C(=O)-N(benzyl) | 649 | 650 | 326 | 2-[2-(4-amidinophenyl)ethyl]-1-[3-(benzylcarbonylamino)-propyl]-benzimidazol-5-yl-carboxylic acid-N-(2-aminoethyl)-N-(4-chlorbenzyl)-amide |
| 377 | ethyl-cyclohexyl | 584 | 585 | 293 | 2-[2-(4-amidinophenyl)ethyl]-1-(2-cyclohexylethyl)-benzimidazol-5-yl-carboxylic acid-N-(2-aminoethyl)-N-(4-chlorbenzyl)-amide |
| 378 | ethyl-cyclopropyl | 528 | 529 | 265 | 2-[2-(4-amidinophenyl)ethyl]-1-cyclopropylmethyl-benzimidazol-5-yl-carboxylic acid-N-(2-aminoethyl)-N-(4-chlorbenzyl)-amide |
| 379 | ethyl-phenyl | 578 | 579 | 290 | 2-[2-(4-amidinophenyl)ethyl]-1-(2-phenylethyl)-benzimidazol-5-yl-carboxylic acid-N-(2-aminoethyl)-N-(4-chlorbenzyl)-amide |
| 380 | ethyl-(4-chlorophenyl) | 613 | — | 307 | 2-[2-(4-amidinophenyl)ethyl]-1-[2-(4-chlorophenyl)ethyl]-benzimidazol-5-yl-carboxylic acid-N-(2-aminoethyl)-N-(4-chlorbenzyl)-amide |
| 381 | methyl-(4-methylphenyl) | 578 | 579 | 290 | 2-[2-(4-amidinophenyl)ethyl]-1-(4-methylbenzyl)-benzimidazol-5-yl-carboxylic acid-N-(2-aminoethyl)-N-(4-chlorbenzyl)-amide |
| 382 | propyl-(1-methylpyrrolidin-2-yl) | 585 | 586 | 294 | 2-[2-(4-amidinophenyl)ethyl]-1-[2-(1-methylpyrrolidin-2-yl)-ethyl]-benzimidazol-5-yl-carboxylic acid-N-(2-aminoethyl)-N-(4-chlorbenzyl)-amide |
| 383 | (1-benzyl-4-phenyl-piperidin-4-yl)-methyl | 737 | 738 | 370 | 2-[2-(4-amidinophenyl)ethyl]-1-[(1-benzyl-4-phenyl-piperidin-4-yl)-methyl]-benzimidazol-5-yl carboxylic acid-N-(2-aminoethyl)-N-(4-chlorbenzyl)-amide |
| 384 | propyl-[4-(2-methylphenyl)-piperazin-1-yl] | 690 | 691 | 346 | 2-[2-(4-amidinophenyl)ethyl]-1-{3-[4-(2-methylphenyl)-piperazin-1-yl]-propyl}-benzimidazol-5-yl-carboxylic acid-N-(2-aminoethyl)-N-(4-chlorbenzyl)-amide |
| 385 | propyl-morpholin-4-yl | 601 | 602 | 302 | 2-[2-(4-amidinophenyl)ethyl]-1-[3-(morpholin-4-yl)-propyl]-benzimidazol-5-yl-carboxylic acid-N-(2-aminoethyl)-N-(4-chlorbenzyl)-amide |
| 386 | methyl-(tetrahydrofuran-2-yl) | 558 | 559 | 280 | 2-[2-(4-amidinophenyl)ethyl]-1-(tetrahydrofuran-2-yl-methyl)-benzimidazol-5-yl-carboxylic acid-N-(2-aminoethyl)-N-(4-chlorbenzyl)-amide |
| 387 | methyl-(thiophen-2-yl) | 570 | 571 | 286 | 2-[2-(4-amidinophenyl)ethyl]-1-(2-thiophenyl-methyl)-benzimidazol-5-yl-carboxylic acid-N-(2-aminoethyl)-N-(4-chlorbenzyl)-amide |

TABLE 20-continued

Compounds of general formula (I) according to the invention wherein the following definitions apply:

$-R^2$: —C(=NH)NH$_2$;  $-R^3$: —CH$_2$CH$_2$NH$_2$ ;  $-R^4$: —CH$_2$-(4-chlorophenyl)

| Ex. | $-R^1$ | calc. [M] | found * | found # | Chemical name |
|---|---|---|---|---|---|
| 388 | (1,3-benzodioxol-5-yl-methyl) | 608 | 609 | 305 | 2-[2-(4-amidinophenyl)ethyl]-1-(1,3-benzodioxol-5-yl-methyl)-benzimidazol-5-yl-carboxylic acid-N-(2-aminoethyl)-N-(4-chlorbenzyl)-amide |

*[M + H]$^{3O}$; #[M + 2H]$^{2+}$

TABLE 21

Compounds of general formula (I) according to the invention wherein the following definitions apply:

$-R^2$: —C(=NH)NH$_2$;  $-R^3$: —CH$_2$CH$_2$NH$_2$ ;  $-R^4$: —CH$_2$-(3-trifluoromethylphenyl)

| Ex. | $-R^1$ | calc. [M] | found * | found # | Chemical name |
|---|---|---|---|---|---|
| 389 | n-decyl- | 648 | 649 | 325 | 2-[2-(4-amidinophenyl)ethyl]-1-n-decyl-benzimidazol-5-yl-carboxylic acid-N-(2-aminoethyl)-N-(3-trifluoromethylbenzyl)-amide |
| 390 | —(CH$_2$)$_3$OEt | 594 | 595 | 298 | 2-[2-(4-amidinophenyl)ethyl]-1-(3-ethoxypropyl)-benzimidazol-5-yl-carboxylic acid-N-(2-aminoethyl)-N-(3-trifluoromethylbenzyl)-amide |
| 391 | —(CH$_2$)$_3$N(n-Butyl)$_2$ | 677 | 678 | 339 | 2-[2-(4-amidinophenyl)ethyl]-1-(3-di-n-butylaminopropyl)-benzimidazol-5-yl-carboxylic acid-N-(2-aminoethyl)-N-(3-trifluoromethylbenzyl)-amide |
| 392 | —(CH$_2$)$_3$NHC(O)CH$_2$-Benzyl | 683 | 684 | 342 | 2-[2-(4-amidinophenyl)ethyl]-1-[3-(benzylcarbonylamino)-propyl]-benzimidazol-5-yl-carboxylic acid-N-(2-aminoethyl)-N-(3-trifluoromethylbenzyl)-amide |
| 393 | —CH$_2$CH$_2$-cyclohexyl | 618 | 619 | 310 | 2-[2-(4-amidinophenyl)ethyl]-1-(2-cyclohexylethyl)-benzimidazol-5-yl-carboxylic acid-N-(2-aminoethyl)-N-(3-trifluoromethylbenzyl)-amide |
| 394 | —CH$_2$-cyclopropyl | 562 | 563 | 282 | 2-[2-(4-amidinophenyl)ethyl]-1-cyclopropylmethyl-benzimidazol-5-yl-carboxyiic acid-N-(2-aminoethyl)-N-(3-trifluoromethylbenzyl)-amide |
| 395 | —CH$_2$CH$_2$-phenyl | 612 | 613 | 307 | 2-[2-(4-amidinophenyl)ethyl]-1-(2-phenylethyl)-benzimidazol-5-yl-carboxylic acid-N-(2-aminoethyl)-N-(3-trifluoromethylbenzyl)-amide |

TABLE 21-continued

Compounds of general formula (I) according to the invention wherein the following definitions apply:

−R²: —C(=NH)NH₂;  −R³: —CH₂CH₂—NH₂;  —R⁴: 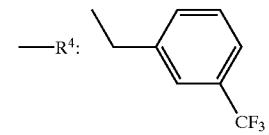 (3-trifluoromethylbenzyl)

| Ex. | −R¹ | calc. [M] | found * | found # | Chemical name |
|---|---|---|---|---|---|
| 396 | 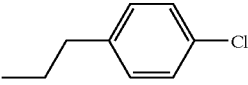 (4-chlorophenyl)ethyl | 646 | 647 | 324 | 2-[2-(4-amidinophenyl)ethyl]-1-[2-(4-chlorophenyl)ethyl]-benzimidazol-5-yl-carboxylic acid-N-(2-aminoethyl)-N-(3-trifluoromethylbenzyl)-amide |
| 397 | 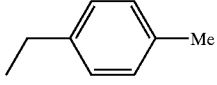 (4-methylphenyl)ethyl | 612 | 613 | 307 | 2-[2-(4-amidinophenyl)ethyl]-1-(4-methylbenzyl)-benzimidazol-5-yl-carboxylic acid-N-(2-aminoethyl)-N-(3-trifluoromethylbenzyl)-amide |
| 398 | 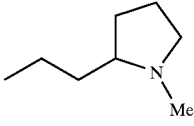 (1-methylpyrrolidin-2-yl)ethyl | 619 | 620 | 310 | 2-[2-(4-amidinophenyl)ethyl]-1-[2-(1-methylpyrrolidin-2-yl)-ethyl]-benzimidazol-5-yl-carboxylic acid-N-(2-aminoethyl)-N-(3-trifluoromethylbenzyl)-amide |
| [001b] 399 | 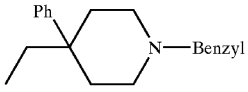 (1-benzyl-4-phenyl-piperidin-4-yl)methyl | 771 | 772 | 386 | 2-[2-(4-amidinophenyl)ethyl]-1-[(1-benzyl-4-phenyl-piperidin-4-yl)-methyl]-benzimidazol-5-yl-carboxylic acid-N-(2-aminoethyl)-N-(3-trifluoromethylbenzyl)-amide |
| 400 | 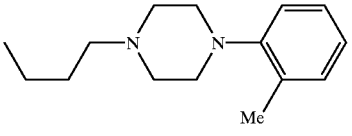 {3-[4-(2-methylphenyl)-piperazin-1-yl]-propyl} | 724 | 725 | 363 | 2-[2-(4-amidinophenyl)ethyl]-1-{3-[4-(2-methylphenyl)-piperazin-1-yl]-propyl}-benzimidazol-5-yl-carboxylic acid-N-(2-aminoethyl)-N-(3-trifluoromethylbenzyl)-amide |
| 401 | 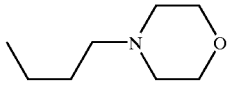 3-(morpholin-4-yl)-propyl | 635 | 636 | 318 | 2-[2-(4-amidinophenyl)ethyl]-1-[3-(morpholin-4-yl)-propyl]-benzimidazol-5-yl-carboxylic acid-N-(2-aminoethyl)-N-(3-trifluoromethylbenzyl)-amide |
| 402 | 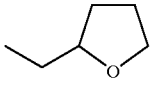 (tetrahydrofuran-2-yl-methyl) | 592 | 593 | 297 | 2-[2-(4-amidinophenyl)ethyl]-1-(tetrahydrofuran-2-yl-methyl)-benzimidazol-5-yl-carboxylic acid-N-(2-aminoethyl)-N-(3-trifluoromethylbenzyl)-amide |
| 403 | 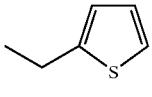 (2-thiophenyl-methyl) | 604 | 605 | 303 | 2-[2-(4-amidinophenyl)ethyl]-1-(2-thiophenyl-methyl)-benzimidazol-5-yl-carboxylic acid-N-(2-aminoethyl-N-(3-trifluoromethylbenzyl)-amide |
| 404 | 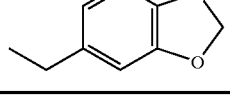 (1,3-benzodioxol-5-yl-methyl) | 642 | 643 | 322 | 2-[2-(4-amidinophenyl)ethyl]-1-(1,3-benzodioxol-5-yl-methyl)-benzimidazol-5-yl-carboxylic acid-N-(2-aminoethyl)-N-(3-trifluoromethylbenzyl)-amide |

*[M + H]⁺; #[M + 2H]²⁺

TABLE 22

Compounds of general formula (I) according to the invention wherein the following definitions apply:

-R²: —C(=NH)NH₂;  -R³: —CH₂CH₂—NH₂;  -R⁴: 2-fluoro-6-ethylphenyl (2-ethyl-6-fluorobenzyl group shown)

| Ex. | -R¹ | calc. [M] | found * | found # | Chemical name |
|---|---|---|---|---|---|
| 405 | n-decyl- | 598 | 599 | 300 | 2-[2-(4-amidinophenyl)ethyl]-1-n-decyl-benzimidazol-5-yl-carboxylic acid-N-(2-aminoethyl)-N-(2-fluorobenzyl)-amide |
| 406 | —CH₂CH₂CH₂—OEt | 544 | 545 | 273 | 2-[2-(4-amidinophenyl)ethyl]-1-(3-ethoxypropyl)-benzimidazol-5-yl-carboxylic acid-N-(2-aminoethyl)-N-(2-fluorobenzyl)-amide |
| 407 | —CH₂CH₂CH₂—N(n-Butyl)₂ | 627 | 628 | 314 | 2-[2-(4-amidinophenyl)ethyl]-1-(3-di-n-butylaminopropyl)-benzimidazol-5-yl-carboxylic acid-N-(2-aminoethyl)-N-(2-fluorobenzyl)-amide |
| 408 | —CH₂CH₂CH₂—N(H)—C(=O)—Benzyl | 633 | 634 | 317 | 2-[2-(4-amidinophenyl)ethyl]-1-[3-(benzylcarbonylamino)-propyl]-benzimidazol-5-yl-carboxylic acid-N-(2-aminoethyl)-N-(2-fluorobenzyl)-amide |
| 409 | —CH₂CH₂-cyclohexyl | 568 | 569 | 285 | 2-[2-(4-amidinophenyl)ethyl]-1-(2-cyclohexylethyl)-benzimidazol-5-yl-carboxylic acid-N-(2-aminoethyl)-N-(2-fluorobenzyl)-amide |
| 410 | —CH₂-cyclopropyl | 512 | 513 | 257 | 2-[2-(4-amidinophenyl)ethyl]-1-cyclopropylmethyl-benzimidazol-5-yl-carboxylic acid-N-(2-aminoethyl)-N-(2-fluorobenzyl)-amide |
| 411 | —CH₂CH₂-phenyl | 562 | 563 | 282 | 2-[2-(4-amidinophenyl)ethyl]-1-(2-phenylethyl)-benzimidazol-5-yl-carboxylic acid-N-(2-aminoethyl)-N-(2-fluorobenzyl)-amide |
| 412 | —CH₂CH₂-(4-chlorophenyl) | 596 | 597 | 299 | 2-[2-(4-amidinophenyl)ethyl]-1-[2-(4-chlorophenyl)ethyl]-benzimidazol-5-yl-carboxylic acid-N-(2-aminoethyl)-N-(2-fluorobenzyl)-amide |
| 413 | —CH₂-(4-methylphenyl) | 562 | 563 | 282 | 2-[2-(4-amidinophenyl)ethyl]-1-(4-methylbenzyl)-benzimidazol-5-yl-carboxylic acid-N-(2-aminoethyl)-N-(2-fluorobenzyl)-amide |
| 414 | —CH₂CH₂-(1-methylpyrrolidin-2-yl) | 569 | 570 | 285 | 2-[2-(4-amidinophenyl)ethyl]-1-[2-(1-methylpyrrolidin-2-yl)-ethyl]-benzimidazol-5-yl-carboxylic acid-N-(2-aminoethyl)-N-(2-fluorobenzyl)-amide |
| 415 | (1-benzyl-4-phenyl-piperidin-4-yl)methyl | 721 | 722 | 361 | 2-[2-(4-amidinophenyl)ethyl]-1-[(1-benzyl-4-phenyl-piperidin-4-yl)-methyl]-benzimidazol-5-yl-carboxylic acid-N-(2-aminoethyl)-N-(2-fluorobenzyl)-amide |

TABLE 22-continued

Compounds of general formula (I) according to the invention wherein the following definitions apply:

$-R^2$: —C(=NH)NH$_2$; $-R^3$: —CH$_2$CH$_2$CH$_2$—NH$_2$; $-R^4$: 2-fluorobenzyl (2-ethyl-fluorophenyl)

| Ex. | $-R^1$ | calc. [M] | found * | found # | Chemical name |
|---|---|---|---|---|---|
| 416 | 4-(2-methylphenyl)-piperazin-1-yl-propyl (butyl-piperazine-tolyl) | 674 | 675 | 338 | 2-[2-(4-amidinophenyl)ethyl]-1-{3-[4-(2-methylphenyl)-piperazin-1-yl]-propyl}-benzimidazol-5-yl-carboxylic acid-N-(2-aminoethyl)-N-(2-fluorobenzyl)-amide |
| 417 | (morpholin-4-yl)-propyl | 585 | 586 | 293 | 2-[2-(4-amidinophenyl)ethyl]-1-[3-(morpholin-4-yl)-propyl]-benzimidazol-5-yl-carboxylic acid-N-(2-aminoethyl)-N-(2-fluorobenzyl)-amide |
| 418 | (tetrahydrofuran-2-yl-methyl) | 542 | 543 | 272 | 2-[2-(4-amidinophenyl)ethyl]-1-(tetrahydrofuran-2-yl-methyl)-benzimidazol-5-yl-carboxylic acid-N-(2-aminoethyl)-N-(2-fluorobenzyl)-amide |
| 419 | (2-thiophenyl-methyl) | 554 | 555 | 278 | 2-[2-(4-amidinophenyl)ethyl]-1-(2-thiophenyl-methyl)-benzimidazol-5-yl-carboxylic acid-N-(2-aminoethyl)-N-(2-fluorobenzyl)-amide |
| 420 | (1,3-benzodioxol-5-yl-methyl) | 592 | 593 | 297 | 2-[2-(4-amidinophenyl)ethyl]-1-(1,3-benzodioxol-5-yl-methyl)-benzimidazol-5-yl-carboxylic acid-N-(2-aminoethyl)-N-(2-fluorobenzyl)-amide |

*[M + H]$^+$; #[M + 2H]$^{2+}$

TABLE 23

Compounds of general formula (I) according to the invention wherein the following definitions apply:

$-R^2$: —C(=NH)NH$_2$; $-R^3$: —CH$_2$CH$_2$CH$_2$—NH$_2$; $-R^4$: 2-naphthylmethyl

| Ex. | $-R^1$ | calc. [M] | found * | found # | Chemical name |
|---|---|---|---|---|---|
| 421 | n-decyl- | 630 | 631 | 316 | 2-[2-(4-amidinophenyl)ethyl]-1-n-decyl-benzimidazol-5-yl-carboxylic acid-N-(2-aminoethyl)-N-(2-naphthylmethyl)-amide |
| 422 | —(CH$_2$)$_3$—OEt | 576 | 577 | 289 | 2-[2-(4-amidinophenyl)ethyl]-1-(3-ethoxypropyl)-benzimidazol-5-yl-carboxyiic acid-N-(2-aminoethyl)-N-(2-naphthylmethyl)-amide |
| 423 | —(CH$_2$)$_3$—N(n-Butyl)$_2$ | 659 | 660 | 330 | 2-[2-(4-amidinophenyl)ethyl]-1-(3-di-n-butylaminopropyl)-benzimidazol-5-yl-carboxylic acid-N-(2-aminoethyl)-N-(2-naphthylmethyl)-amide |

TABLE 23-continued

Compounds of general formula (I) according to the invention wherein the following definitions apply:

$-R^2$: $-C(=NH)NH_2$; $-R^3$: -CH₂CH₂CH₂-NH₂; $-R^4$: -CH₂-(2-naphthyl)

| Ex. | -R¹ | calc. [M] | found * | found # | Chemical name |
|---|---|---|---|---|---|
| 424 | butyl-N(H)-C(=O)-N(Benzyl)- | 665 | 666 | 333 | 2-[2-(4-amidinophenyl)ethyl]-1-[3-(benzylcarbonylamino)-propyl]-benzimidazol-5-yl-carboxylic acid-N-(2-aminoethyl)-N-(2-naphthylmethyl)-amide |
| 425 | 2-(cyclohexyl)ethyl | 600 | 601 | 301 | 2-[2-(4-amidinophenyl)ethyl]-1-(2-cyclohexylethyl)-benzimidazol-5-yl-carboxylic acid-N-(2-aminoethyl)-N-(2-naphthylmethyl)-amide |
| 426 | cyclopropylmethyl | 544 | 545 | 273 | 2-[2-(4-amidinophenyl)ethyl]-1-cyclopropylmethyl-benzimidazol-5-yl-carboxylic acid-N-(2-aminoethyl)-N-(2-naphthylmethyl)-amide |
| 427 | 2-phenylethyl | 594 | 595 | 298 | 2-[2-(4-amidinophenyl)ethyl]-1-(2-phenylethyl)-benzimidazol-5-yl-carboxylic acid-N-(2-aminoethyl)-N-(2-naphthylmethyl)-amide |
| 428 | 2-(4-chlorophenyl)ethyl | 628 | 629 | 315 | 2-[2-(4-amidinophenyl)ethyl]-1-[2-(4-chlorophenyl)ethyl]-benzimidazol-5-yl-carboxylic acid-N-(2-aminoethyl)-N-(2-naphthylmethyl)-amide |
| 429 | 4-methylbenzyl | 594 | 595 | 298 | 2-[2-(4-amidinophenyl)ethyl]-1-(4-methylbenzyl)-benzimidazol-5-yl-carboxylic acid-N-(2-aminoethyl)-N-(2-naphthylmethyl)-amide |
| 430 | 2-(1-methylpyrrolidin-2-yl)ethyl | 601 | 602 | 301 | 2-[2-(4-amidinophenyl)ethyl]-1-[2-(1-methylpyrrolidin-2-yl)-ethyl]-benzimidazol-5-yl-carboxylic acid-N-(2-aminoethyl)-N-(2-naphthylmethyl)-amide |
| 431 | (1-benzyl-4-phenyl-piperidin-4-yl)methyl | 753 | — | 378 | 2-[2-(4-amidinophenyl)ethyl]-1-[(1-benzyl-4-phenyl-piperidin-4-yl)-methyl]-benzimidazol-5-yl-carboxylic acid-N-(2-aminoethyl)-N-(2-naphthylmethyl)-amide |
| 432 | 3-[4-(2-methylphenyl)-piperazin-1-yl]propyl | 706 | 707 | 354 | 2-[2-(4-amidinophenyl)ethyl]-1-{3-[4-(2-methylphenyl)-piperazin-1-yl]-propyl}-benzimidazol-5-yl-carboxylic acid-N-(2-aminoethyl)-N-(2-naphthylmethyl)-amide |
| 433 | 3-(morpholin-4-yl)propyl | 617 | 618 | 309 | 2-[2-(4-amidinophenyl)ethyl]-1-[3-(morpholin-4-yl)-propyl]-benzimidazol-5-yl-carboxylic acid-N-(2-aminoethyl)-N-(2-naphthylmethyl)-amide |
| 434 | (tetrahydrofuran-2-yl)methyl | 574 | 575 | 288 | 2-[2-(4-amidinophenyl)ethyl]-1-(tetrahydrofuran-2-yl-methyl)-benzimidazol-5-yl-carboxylic acid-N-(2-aminoethyl)-N-(2-naphthylmethyl)-amide |
| 435 | (2-thiophenyl)methyl | 586 | — | 294 | 2-[2-(4-amidinophenyl)ethyl]-1-(2-thiophenyl-methyl)-benzimidazol-5-yl-carboxylic acid-N-(2-aminoethyl)-N-(2-naphthylmethyl)-amide |

TABLE 23-continued

Compounds of general formula (I) according to the invention wherein the following definitions apply:

$-R^2$: —C(=NH)NH$_2$; $-R^3$: [propyl-NH$_2$]; $-R^4$: [2-ethylnaphthyl]

| Ex. | $-R^1$ | calc. [M] | found * | found # | Chemical name |
|---|---|---|---|---|---|
| 436 | [5-ethyl-1,3-benzodioxole] | 624 | 625 | 313 | 2-[2-(4-amidinophenyl)ethyl]-1-(1,3-benzodioxol-5-yl-methyl)-benzimidazol-5-yl-carboxylic acid-N-(2-aminoethyl)-N-(2-naphthylmethyl)-amide |

*[M + H]⁺; #[M + 2H]²⁺

TABLE 24

Compounds of general formula (I) according to the invention wherein the following definitions apply:

$-R^2$: —C(=NH)NH$_2$; $-R^3$: [4-ethylbenzyl-NH$_2$]; $-R^4$: [methyl 4-ethylbenzoate]

| Ex. | $-R^1$ | calc. [M] | found * | found # | Chemical name |
|---|---|---|---|---|---|
| 437 | n-decyl- | 714 | 715 | 358 | 2-[2-(4-amidinophenyl)ethyl]-1-n-decyl-benzimidazol-5-yl-carboxylic acid-N-[4-(amino-methyl)-benzyl]-N-[4-(methoxycarbonyl)-benzyl]-amide |
| 438 | [propyl-OEt] | 660 | 661 | 331 | 2-[2-(4-amidinophenyl)ethyl]-1-(3-ethoxypropyl)-benzimidazol-5-yl-carboxylic acid-N-[4-(amino-methyl)-benzyl]-N-[4-(methoxycarbonyl)-benzyl]-amide |
| 439 | [propyl-N(n-Butyl)$_2$] | 743 | 744 | 373 | 2-[2-(4-amidinophenyl)ethyl]-1-(3-di-n-butylaminopropyl)-benzimidazol-5-yl-carboxylic acid-N-[4-(amino-methyl)-benzyl]-N-[4-(methoxycarbonyl)-benzyl]-amide |
| 440 | [propyl-NH-C(=O)-Benzyl] | 749 | — | — | 2-[2-(4-amidinophenyl)ethyl]-1-[3-(benzylcarbonylamino)-propyl]-benzimidazol-5-yl-carboxylic acid-N-[4-(amino-methyl)-benzyl]-N-[4-(methoxycarbonyl)-benzyl]-amide |
| 441 | [ethyl-cyclohexyl] | 684 | — | 343 | 2-[2-(4-amidinophenyl)ethyl]-1-(2-cyclohexylethyl)-benzimidazol-5-yl-carboxylic acid-N-[4-(amino-methyl)-benzyl]-N-[4-(methoxycarbonyl)-benzyl]-amide |
| 442 | [methyl-cyclopropyl] | 628 | 629 | 315 | 2-[2-(4-amidinophenyl)ethyl]-1-cyclopropylmethyl-benzimidazol-5-yl-carboxylic acid-N-[4-(amino-methyl)-benzyl]-N-[4-(methoxycarbonyl)-benzyl]-amide |
| 443 | [ethyl-phenyl] | 678 | — | 340 | 2-[2-(4-amidinophenyl)ethyl]-1-(2-phenylethyl)-benzimidazol-5-yl-carboxylic acid-N-[4-(amino-methyl)-benzyl]-N-[4-(methoxycarbonyl)-benzyl]-amide |

TABLE 24-continued

Compounds of general formula (I) according to the invention wherein the following definitions apply:

-R²: —C(=NH)NH₂; -R³: 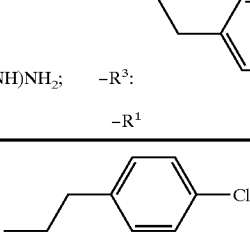 NH₂; -R⁴: 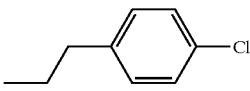 OMe

| Ex. | -R¹ | calc. [M] | found * | found # | Chemical name |
|---|---|---|---|---|---|
| 444 |  | 712 | 713 | 357 | 2-[2-(4-amidinophenyl)ethyl]-1-[2-(4-chlorophenyl)ethyl]-benzimidazol-5-yl-carboxylic acid-N-[4-(amino-methyl)-benzyl]-N-[4-(methoxycarbonyl)-benzyl]-amide |
| 445 | 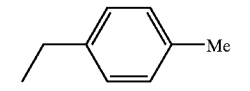 | 678 | — | 340 | 2-[2-(4-amidinophenyl)ethyl]-1-(4-methylbenzyl)-benzimidazol-5-yl-carboxylic acid-N-[4-(amino-methyl)-benzyl]-N-[4-(methoxycarbonyl)-benzyl]-amide |
| 446 |  | 685 | — | 343 | 2-[2-(4-amidinophenyl)ethyl]-1-[2-(1-methylpyrrolidin-2-yl)-ethyl]-benzimidazol-5-yl-carboxylic acid-N-[4-(amino-methyl)-benzyl]-N-[4-(methoxycarbonyl)-benzyl]-amide |
| 447 | 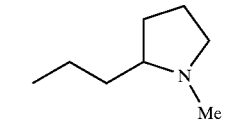 | 837 | — | — | 2-[2-(4-amidinophenyl)ethyl]-1-[(1-benzyl-4-phenyl-piperidin-4-yl)-methyl]-benzimidazol-5-yl-carboxylic acid-N-[4-(amino-methyl)-benzyl]-N-[4-(methoxycarbonyl)-benzyl]-amide |
| 448 |  | 790 | 791 | 396 | 2-[2-(4-amidinophenyl)ethyl]-1-{3-[4-(2-methylphenyl)-piperazin-1-yl]-propyl}-benzimidazol-5-yl-carboxylic acid-N-[4-(amino-methyl)-benzyl]-N-[4-(methoxycarbonyl)-benzyl]-amide |
| 449 | 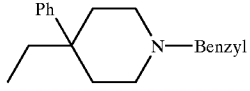 | 701 | 702 | 351 | 2-[2-(4-amidinophenyl)ethyl]-1-[3-(morpholin-4-yl)-propyl]-benzimidazol-5-yl-carboxylic acid-N-[4-(amino-methyl)-benzyl]-N-[4-(methoxycarbonyl)-benzyl]-amide |
| 450 |  | 658 | 659 | 330 | 2-[2-(4-amidinophenyl)ethyl]-1-(tetrahydrofuran-2-yl-methyl)-benzimidazol-5-yl-carboxylic acid-N-[4-(amino-methyl)-benzyl]-N-[4-(methoxycarbonyl)-benzyl]-amide |
| 451 | 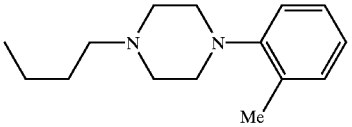 | 670 | — | — | 2-[2-(4-amidinophenyl)ethyl]-1-(2-thiophenyl-methyl)-benzimidazol-5-yl-carboxylic acid-N-[4-(amino-methyl)-benzyl]-N-[4-(methoxycarbonyl)-benzyl]-amide |
| 452 |  | 708 | 709 | 347 | 2-[2-(4-amidinophenyl)ethyl]-1-(1,3-benzodioxol-5-yl-methyl)-benzimidazol-5-yl-carboxylic acid-N-[4-(amino-methyl)-benzyl]-N-[4-(methoxycarbonyl)-benzyl]-amide |

*[M + H]⁺; #[M + 2H]²⁺

The mass spectrometry data listed above were determined by MS-ESI (Electrospray Ionisation).

The compounds according to the invention are characterised by their tryptase-inhibiting activity. This ability to inhibit tryptase was investigated using the test described below.

The measurement is carried out in Tris HCl buffer (100 mM), which additionally contains calcium (5 mM) and heparin (100 mg/ml), at pH 7.4. The standard used is rh beta tryptase which may be obtained commercially from Promega, for example. The substrate used is N-p-tosyl-Gly-Pro-Lys-para-nitroaniline in a concentration of 0.6 mM. The substrate is digested with tryptase to form p-nitroaniline which can be measured at 405 nm. Usually, an incubation period of 5 minutes and an incubation temperature of 37° C. are chosen. The enzyme activity used is 0.91 U/ml. The measurements are carried out in an Autoanalyser (Cobas Bio) made by Hofmann LaRoche. The potential inhibitory substances are used in concentrations of 10 μM in the screening, the inhibition of the tryptase being given in percent. The $IC_{50}$ is determined at over 70% inhibition (concentration at which 50% of the enzyme activity is inhibited). After 5 minutes' pre-incubation of the potential inhibitory substances, the substrate is added to start the reaction, the formation of p-nitroaniline being taken as a measurement of the enzyme activity after 5 minutes, after testing the linearity.

The data obtained after the above test has been carried out (% inhibition) are assembled in Table 25 for the compounds according to the invention. The $IC_{50}$ values obtained for the compounds according to the invention can be found in Table 26.

TABLE 25

| Example | % Inhibition (10 μM) | Example | % Inhibition (10 μM) |
|---|---|---|---|
| 70 | 63 | 124 | 55 |
| 71 | 58 | 125 | 63 |
| 72 | 69 | 128 | 51 |
| 74 | 66 | 129 | 63 |
| 75 | 60 | 130 | 77 |
| 76 | 58 | 134 | 69 |
| 80 | 53 | 135 | 64 |
| 81 | 69 | 136 | 74 |
| 82 | 61 | 137 | 52 |
| 86 | 72 | 138 | 72 |
| 87 | 59 | 139 | 76 |
| 88 | 70 | 140 | 63 |
| 90 | 67 | 144 | 54 |
| 91 | 62 | 145 | 73 |
| 93 | 56 | 146 | 65 |
| 96 | 55 | 147 | 51 |
| 97 | 56 | 150 | 60 |
| 98 | 67 | 152 | 65 |
| 99 | 58 | 154 | 63 |
| 100 | 67 | 155 | 57 |
| 103 | 60 | 161 | 56 |
| 104 | 74 | 162 | 60 |
| 106 | 58 | 166 | 57 |
| 107 | 65 | 167 | 52 |
| 113 | 56 | 168 | 66 |
| 114 | 58 | 169 | 52 |
| 118 | 71 | 170 | 57 |
| 119 | 57 | 173 | 51 |
| 120 | 74 | 177 | 68 |
| 121 | 52 | 178 | 51 |
| 122 | 70 | 182 | 67 |
| 123 | 60 | 183 | 56 |
| 184 | 72 | 284 | 55 |
| 186 | 60 | 288 | 65 |
| 187 | 63 | 290 | 70 |
| 193 | 59 | 291 | 75 |
| 194 | 61 | 294 | 69 |
| 198 | 63 | 295 | 55 |
| 200 | 69 | 296 | 51 |
| 202 | 58 | 298 | 57 |
| 203 | 53 | 304 | 51 |
| 209 | 61 | 306 | 62 |
| 210 | 59 | 307 | 57 |
| 214 | 54 | 310 | 70 |
| 216 | 65 | 312 | 55 |
| 219 | 51 | 314 | 61 |
| 225 | 58 | 322 | 51 |
| 226 | 64 | 323 | 59 |
| 230 | 61 | 326 | 51 |
| 231 | 54 | 330 | 54 |
| 232 | 58 | 342 | 75 |
| 233 | 53 | 346 | 51 |
| 235 | 52 | 352 | 51 |
| 237 | 52 | 354 | 58 |
| 241 | 69 | 355 | 51 |
| 242 | 63 | 358 | 77 |
| 262 | 58 | 359 | 59 |

TABLE 25-continued

| Example | % Inhibition (10 μM) | Example | % Inhibition (10 μM) |
|---|---|---|---|
| 266 | 61 | 362 | 74 |
| 274 | 57 | 369 | 57 |
| 278 | 83 | 370 | 53 |
| 279 | 60 | 371 | 55 |
| 280 | 59 | 374 | 62 |
| 282 | 65 | 375 | 58 |
| 283 | 59 | 378 | 52 |
| 384 | 59 | | |
| 386 | 55 | | |
| 387 | 55 | | |
| 390 | 60 | | |
| 394 | 52 | | |
| 400 | 52 | | |
| 402 | 51 | | |
| 406 | 54 | | |
| 422 | 58 | | |
| 438 | 59 | | |
| 440 | 64 | | |
| 442 | 59 | | |
| 443 | 52 | | |
| 444 | 53 | | |
| 445 | 52 | | |
| 450 | 72 | | |

Table 26 contains the $IC_{50}$ binding values obtained for the compounds according to the invention. These were measured as described above.

TABLE 26

| Example | $IC_{50}$ [μM] |
|---|---|
| 1 | 0.887 |
| 2 | 0.153 |
| 3 | 0.66 |
| 4 | 0.081 |
| 5 | 0.245 |
| 6 | 0.571 |
| 7 | 0.67 |
| 8 | 0.201 |
| 9 | 0.14 |
| 10 | 0.316 |
| 11 | 0.086 |
| 12 | 0.479 |
| 15 | 0.098 |
| 16 | 0.1545 |
| 17 | 0.1069 |
| 18 | 0.312 |
| 19 | 0.032 |
| 20 | 0.31 |
| 21 | 0.051 |
| 22 | 0.056 |
| 23 | 0.049 |
| 24 | 0.016 |
| 25 | 0.055 |
| 26 | 0.168 |
| 27 | 0.153 |
| 29 | 0.158 |
| 36 | 0.067 |
| 37 | 0.068 |
| 38 | 0.113 |
| 40 | 0.192 |
| 41 | 0.1725 |
| 42 | 0.836 |
| 43 | 0.319 |
| 47 | 0.118 |
| 48 | 0.147 |
| 49 | 0.152 |
| 50 | 0.176 |
| 51 | 0.231 |
| 52 | 0.231 |

TABLE 26-continued

| Example | IC$_{50}$ [μM] |
|---|---|
| 53 | 0.241 |
| 54 | 0.305 |
| 55 | 0.346 |
| 70 | 0.422 |
| 86 | 0.135 |
| 102 | 0.369 |
| 107 | 0.344 |
| 118 | 0.304 |
| 122 | 0.515 |
| 134 | 0.231 |
| 138 | 0.431 |
| 150 | 0.292 |
| 166 | 0.274 |
| 198 | 0.458 |
| 202 | 0.822 |
| 214 | 0.335 |
| 230 | 0.153 |
| 234 | 0.76 |
| 262 | 0.284 |
| 266 | 0.641 |
| 278 | 0.251 |
| 294 | 0.35 |
| 310 | 0.253 |
| 314 | 0.771 |
| 326 | 0.288 |
| 330 | 0.503 |
| 342 | 0.275 |
| 358 | 0.169 |
| 390 | 0.402 |
| 406 | 0.392 |
| 410 | 0.626 |
| 422 | 0.364 |

The tryptase inhibitors according to the invention may be administered orally, transdermally, by inhalation or parenterally. The compounds according to the invention, meaning compounds of the formulas (I) and (II), may be incorporated, as active ingredients of formula (I) or as prodrugs of the formula (II), into otherwise conventional pharmaceutical preparations, for example in compositions which consist essentially of an inert pharmaceutical carrier and an effective dose of the active substance, such as for example tablets, coated tablets, capsules, powders, solutions, suspensions, emulsions, syrups, suppositories, transdermal systems etc. An effective dose of the compounds according to the invention, whether of the formula (I) or (II), is between 1 and 100, preferably between 1 and 50, most preferably between 5–30 mg/dose for oral adminstration, and between 0.001 and 50, preferably between 0.1 and 10 mg/dose for intravenous or intramuscular administration. For inhalation, according to the invention, solution containing 0.01 to 1.0, preferably 0.1 to 0.5% active substance are suitable. For administration by inhalation the use of powders is preferred. It is also possible to use the compounds according to the invention as a solution for infusion, preferably in a physiological saline or nutrient saline solution.

The compounds according to the invention may be used on their own or in conjunction with other active substances according to the invention, optionally also in conjunction with other pharmacologically active substances. Suitable preparations include for example tablets, capsules, suppositories, solutions, elixirs, emulsions or dispersible powders.

Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number or layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavour enhancer, e.g. a flavouring such as vanilline or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions for injection are prepared in the usual way, e.g. with the addition of preservatives such as p-hydroxybenzoates, or stabilisers such as alkali metal salts of ethylenediamine tetraacetic acid, and transferred into injection vials or ampoules.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

A therapeutically effective daily dose is between 1 and 800 mg, preferably 10–300 mg per adult.

The Examples which follow illustrate the present invention without restricting its scope:

Examples of Pharmaceutical Formulations

| A) | Tablets | per tablet |
|---|---|---|
| | active substance | 100 mg |
| | lactose | 140 mg |
| | corn starch | 240 mg |
| | polyvinylpyrrolidone | 15 mg |
| | magnesium stearate | 5 mg |
| | | 500 mg |

The finely ground active substance, lactose and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

| B) | Tablets | per tablet |
|---|---|---|
| | active substance | 80 mg |
| | corn starch | 190 mg |
| | lactose | 55 mg |
| | microcrystalline cellulose | 35 mg |
| | polyvinylpyrrolidone | 15 mg |
| | sodium-carboxymethyl starch | 23 mg |
| | magnesium stearate | 2 mg |
| | | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sodium-carboxymethyl starch and the magnesium stearate are added and mixed in and the mixture is compressed to form tablets of a suitable size.

| C) | Coated tablets | per coated tablet |
|---|---|---|
| | Active substance | 5 mg |
| | Corn starch | 41.5 mg |
| | Lactose | 30 mg |
| | Polyvinylpyrrolidone | 3 mg |
| | Magnesium stearate | 0.5 mg |
| | | 80 mg |

The active substance, corn starch, lactose and polyvinylpyrrolidone are thoroughly mixed and moistened with water. The moist mass is pushed through a screen with a 1 mm mesh size, dried at about 45° C. and the granules are then passed through the same screen. After the magnesium stearate has been mixed in, convex tablet cores with a diameter of 6 mm are compressed in a tablet-making machine. The tablet cores thus produced are coated in known manner with a covering consisting essentially of sugar and talc. The finished coated tablets are polished with wax.

| D) | Capsules | per capsule |
|---|---|---|
| | Active substance | 50 mg |
| | Corn starch | 268.5 mg |
| | Magnesium stearate | 1.5 mg |
| | | 320 mg |

The substance and corn starch are mixed and moistened with water. The moist mass is screened and dried. The dry granules are screened and mixed with magnesium stearate. The finished mixture is packed into size 1 hard gelatine capsules.

| E) | Ampoule solution | |
|---|---|---|
| | active substance | 50 mg |
| | sodium chloride | 50 mg |
| | water for inj. | 5 ml |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilised and sealed by fusion. The ampoules contain 5 mg, 25 mg and 50 mg of active substance.

| F) | Suppositories | |
|---|---|---|
| | Active substance | 50 mg |
| | Solid fat | 1650 mg |
| | | 1700 mg |

The hard fat is melted. At 40° C. the ground active substance is homogeneously dispersed. It is cooled to 38° C. and poured into slightly chilled suppository moulds.

What is claimed is:

1. A method for treating an inflammatory or allergic disease, which method comprises administering to a host in need of such treatment a therapeutically effective amount of a compound of the formula (I)

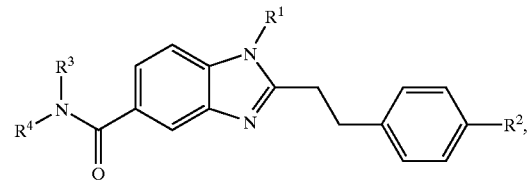

wherein:
R$^1$ denotes C$_1$–C$_{10}$-alkyl, which may optionally be mono-, di- or tri-substituted by one or more of the groups C$_1$–C$_4$-alkoxy, phenoxy, hydroxyphenoxy, C$_1$–C$_4$-alkoxy-phenoxy, C$_3$–C$_6$-cycloalkyl, —NH$_2$, —NH(C$_1$–C$_4$-alkyl), —N(C$_1$–C$_4$-alkyl)$_2$, —NH—CO—(C$_1$–C$_4$-alkyl), —CO—NH$_2$, —CO—NH—(C$_1$–C$_4$-alkyl) or —NH—CO-benzyl, or phenyl-C$_1$–C$_4$-alkyl, wherein the phenyl ring may optionally be mono-, di- or tri- substituted by one or more of the groups C$_1$–C$_4$-alkyl, CF$_3$, fluorine, chlorine, bromine, COOH or COO—C$_1$–C$_4$-alkyl, or a 5 or 6 membered, saturated or unsaturated heterocyclic group linked via a single bond or via a C$_1$–C$_4$-alkylene bridge, which heterocyclic group contains one, two or three heteroatoms selected from the group consisting of oxygen, nitrogen and sulphur and which may optionally be mono-, di- or tri-substituted by one or more of the groups C$_1$–C$_4$-alkyl, optionally by C$_1$–C$_4$-alkyl substituted phenyl or optionally by C$_1$–C$_4$-alkyl substituted benzyl or to which a benzene ring may optionally be fused via two adjacent carbon atoms;

$R^2$ denotes —C(=NH)NH$_2$ or —CH$_2$—NH$_2$;

$R^3$ and $R^4$ which may be identical or different, denote hydrogen, C$_1$–C$_6$-alkyl, which may be mono- or dis-ubstituted by one or more of the groups COOH, COO—C$_1$–C$_4$-alkyl, C$_3$–C$_6$-cycloalkyl, —NH$_2$, —NH(C$_1$–C$_4$-alkyl), —N(C$_1$–C$_4$-alkyl)$_2$, —NHphenyl, —N(phenyl)$_2$, —NHbenzyl, —N(benzyl)$_2$, —NH—CO—(C$_1$–C$_4$-alkyl), —C(=NH)NH$_2$ or —NH—C(=NH)NH$_2$, or phenyl-C$_1$–C$_4$-alkyl, wherein the C$_1$–C$_4$-alkylene bridge may optionally be substituted by phenyl, COOH or COO—C$_1$–C$_4$-alkyl and wherein the phenyl ring may optionally be mono-, di- or tri-substituted, directly or via a C$_1$–C$_4$-alkylene bridge, by one or more of the groups C$_1$–C$_4$-alkyl, C$_1$–C$_4$-alkoxy, CF$_3$, fluorine, chlorine, bromine, COOH, COO—C$_1$–C$_4$-alkyl, —NH$_2$, —NH(C$_1$–C$_4$-alkyl), —N(C$_1$–C$_4$-alkyl)$_2$, —NHphenyl, —N(phenyl)$_2$, —NHbenzyl, —N(benzyl)$_2$, —NH—CO—(C$_1$C$_4$-alkyl), —C(=NH)NH$_2$ or —NH—C(=NH)NH$_2$, or a 5-, 6- or 7-membered, saturated or unsaturated heterocyclic group linked directly or via a C$_1$–C$_4$-alkylene bridge, which heterocyclic group contains one, two, three or four heteroatoms selected from the group consisting of oxygen, nitrogen and sulphur and which may optionally be mono-, di- or tri-substituted by one or more of the groups C$_1$–C$_4$-alkyl, phenyl or benzyl or to which a benzene ring may optionally be fused via two adjacent carbon atoms, or C$_3$–C$_8$-cycloalkyl, naphthyl or phenyl, which may optionally be mono-, di- or tri-substituted by one or more of the groups C$_1$–C$_4$-alkyl, C$_1$–C$_4$-alkoxy, phenyloxy, benzyloxy, CF$_3$, fluorine, chlorine, bromine, COOH or COO—C$_1$–C$_4$-alkyl, or $R^3$ and $R^4$ together with the nitrogen atom form a 5-, 6- or 7-membered, saturated or unsaturated heterocyclic group, which heterocyclic group optionally contains one or two further heteroatoms selected from the group consisting of oxygen, nitrogen and sulphur and which may optionally be substituted by one or more of the groups C$_1$–C$_4$-alkyl, C$_{5-C_6}$-cycloalkyl, benzyl, which may optionally be substituted by C$_1$–C$_4$-alkyl, pyridyl or phenyl, optionally substituted by C$_1$–C$_4$-alkyl, C$_1$–C$_4$-alkoxy or hydroxy, or a tautomer or pharmaceutically acceptable salt thereof.

2. A method for treating bronchial asthma, allergic rhinitis, allergic conjunctivitis, atopic dermatitis, urticaria, allergic otitis, allergic gastro-intestinal disorders, Crohn's disease, ulcerative colitis, anaphylactic shock, septic shock, shock lung (ARDS) or arthritis, which method comprises administering to a host in need of such treatment a therapeutically effective amount of a compound of the formula (I)

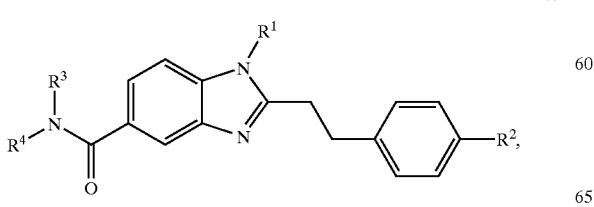

(I)

wherein:

$R^1$ denotes C$_1$–C$_{10}$-alkyl, which may optionally be mono-, di- or tri-substituted by one or more of the groups C$_1$–C$_4$-alkoxy, phenoxy, hydroxyphenoxy, C$_1$–C$_4$alkoxy-phenoxy, C$_3$–C$_6$-cycloalkyl, —NH$_2$, —NH(C$_1$–C$_4$-alkyl), —N(C$_1$–C$_4$-alkyl)$_2$, —NH—CO—(C$_1$–C$_4$-alkyl), —CO—NH$_2$, —CO—NH—(C$_1$–C$_4$-alkyl) or —NH—CO-benzyl, or phenyl-C$_1$–C$_4$-alkyl, wherein the phenyl ring may optionally be mono-, di- or tri-substituted by one or more of the groups C$_1$–C$_4$-alkyl, CF$_3$, fluorine, chlorine, bromine, COOH or COO—C$_1$–C$_4$-alkyl, or a 5 or 6 membered, saturated or unsaturated heterocyclic group linked via a single bond or via a C$_1$–C$_4$-alkylene bridge, which heterocyclic group contains one, two or three heteroatoms selected from the group consisting of oxygen, nitrogen and sulphur and which may optionally be mono-, di- or tri-substituted by one or more of the groups C$_1$–C$_4$-alkyl, optionally by C$_1$–C$_4$-alkyl substituted phenyl or optionally by C$_1$–C$_4$-alkyl substituted benzyl or to which a benzene ring may optionally be fused via two adjacent carbon atoms;

$R^2$ denotes —C(=NH)NH$_2$ or —CH$_2$—NH$_2$;

$R^3$ and $R^4$ which may be identical or different, denote hydrogen, C$_1$–C$_6$-alkyl, which may be mono- or dis-ubstituted by one or more of the groups COOH, COO—C$_1$–C$_4$-alkyl, C$_3$–C$_6$-cycloalkyl, —NH$_2$, —NH(C$_1$–C$_4$-alkyl), —N(C$_1$–C$_4$-alkyl)$_2$, —NHphenyl, —N(phenyl)$_2$, —NHbenzyl, —N(benzyl)$_2$, —NH—CO—(C$_1$–C$_4$-alkyl), —C(=NH)NH$_2$ or —NH—C(=NH)NH$_2$, or phenyl-C$_1$–C$_4$-alkyl, wherein the C$_1$–C$_4$-alkylene bridge may optionally be substituted by phenyl, COOH or COO—C$_1$–C$_4$-alkyl and wherein the phenyl ring may optionally be mono-, di- or tri-substituted, directly or via a C$_1$–C$_4$-alkylene bridge, by one or more of the groups C$_1$–C$_4$-alkyl, C$_1$–C$_4$-alkoxy, CF$_3$, fluorine, chlorine, bromine, COOH, COO—C$_1$–C$_4$-alkyl, —NH$_2$, —NH(C$_1$–C$_4$-alkyl), —N(C$_1$–C$_4$-alkyl)$_2$, —NHphenyl, —N(phenyl)$_2$, —NHbenzyl, —N(benzyl)$_2$, —NH—CO—(C$_1$C$_4$-alkyl), —C(=NH)NH$_2$ or —NH—C(=NH)NH$_2$, or a 5-, 6- or 7-membered, saturated or unsaturated heterocyclic group linked directly or via a C$_1$–C$_4$-alkylene bridge, which heterocyclic group contains one, two, three or four heteroatoms selected from the group consisting of oxygen, nitrogen and sulphur and which may optionally be mono-, di- or tri-substituted by one or more of the groups C$_1$–C$_4$-alkyl, phenyl or benzyl or to which a benzene ring may optionally be fused via two adjacent carbon atoms, or C$_3$–C$_8$-cycloalkyl, naphthyl or phenyl, which may optionally be mono-, di- or tri-substituted by one or more of the groups C$_1$–C$_4$-alkyl, C$_1$–C$_4$-alkoxy, phenyloxy, benzyloxy, CF$_3$, fluorine, chlorine, bromine, COOH or COO—C$_1$–C$_4$-alkyl, or $R^3$ and $R^4$ together with the nitrogen atom form a 5-, 6- or 7-membered, saturated or unsaturated heterocyclic group, which heterocyclic group optionally contains one or two further heteroatoms selected from the group consisting of oxygen, nitrogen and sulphur and which may optionally be substituted by one or more of the groups C$_1$–C$_4$-alkyl, C$_5$–C$_6$-cycloalkyl, benzyl, which may optionally be substituted by C$_1$C$_4$-alkyl, pyridyl or phenyl, optionally substituted by $C_1$–$C_4$-alkyl, $C_1$–$C_4$-alkoxy or hydroxy, or a tautomer or pharmaceutically acceptable salt thereof.

3. A compound of the formula (I)

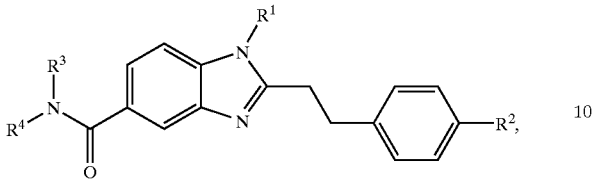

(I)

wherein:
$R^1$ denotes $C_1$–$C_{10}$-alkyl, which may optionally be mono-, di- or tri-substituted by one or more of the groups $C_1$–$C_4$-alkoxy, phenoxy-, $C_1$–$C_4$-alkoxy-phenoxy, hydroxyphenoxy, $C_3$–$C_6$-cycloalkyl, —$NH_2$, —NH($C_1$–$C_4$-alkyl), —N($C_1$–$C_4$-alkyl)$_2$, —NH—CO—($C_1$–$C_4$-alkyl), —CO—$NH_2$, —CO—NH—($C_1$–$C_4$-alkyl) or —NH—CO-benzyl, or phenyl-$C_1$–$C_4$-alkyl, wherein the phenyl ring may optionally be mono-, di- or tri-substituted by one or more of the groups $C_1$–$C_4$-alkyl, $CF_3$, fluorine, chlorine, bromine, COOH or COO—$C_1$–$C_4$-alkyl, or a 5 or 6 membered, saturated or unsaturated heterocyclic group linked via a single bond or via a $C_1$–$C_4$-alkylene bridge, which heterocyclic group contains one, two or three heteroatoms selected from the group consisting of oxygen, nitrogen and sulphur and may optionally be mono-, di- or tri-substituted by one or more of the groups $C_1$–$C_4$-alkyl, optionally by $C_1$–$C_4$-alkyl substituted phenyl or optionally by $C_1$–$C_4$-alkyl substituted benzyl, or to which a benzene ring may optionally be fused via two adjacent carbon atoms;

$R^2$ denotes —C(=NH)$NH_2$ or —$CH_2$—$NH_2$;

$R^3$ denotes $C_1$–$C_6$-alkyl, which is mono- or disubstituted by one or more of the groups —$NH_2$, —NH($C_1$–$C_4$-alkyl), —N($C_1$–$C_4$-alkyl)$_2$, —NHphenyl, —N(phenyl)$_2$, —NHbenzyl, —N(benzyl)$_2$, —NH—CO—($C_1$–$C_4$-alkyl), —C(=NH)$NH_2$ or —NH—C(=NH)$NH_2$, or benzyl, wherein the phenyl ring is mono- or disubstituted, directly or via a $C_1$–$C_4$-alkylene bridge, by one or more of the groups —$NH_2$, —NH($C_1$–$C_4$-alkyl), —N($C_1$–$C_4$-alkyl)$_2$, —NHphenyl, —N(phenyl)$_2$, —NHbenzyl, —N(benzyl)$_2$, —NH—CO—($C_1$–$C_4$-alkyl), —C(=NH)$NH_2$ or —NH—C(=NH)$NH_2$, or phenyl-$C_2$–$C_4$-alkyl, wherein the $C_2$–$C_4$-alkylene bridge may optionally be substituted by phenyl, COOH or COO—$C_1$–$C_4$-alkyl and wherein the phenyl ring may optionally be mono- or di-substituted, directly or via a $C_1$–$C_4$-alkylene bridge, by one or more of the groups —$NH_2$, —NH($C_1$–$C_4$-alkyl), —N($C_1$–$C_4$-alkyl)$_2$—NHphenyl, —N(phenyl)$_2$, —NHbenzyl, —N(benzyl)$_2$, —NH—CO—($C_1$–$C_4$-alkyl), —C(=NH)$NH_2$ or —NH—C(=NH)$NH_2$, or a 5 or 6 membered, saturated or unsaturated heterocyclic group linked via a $C_1$–$C_4$-alkylene bridge, which heterocyclic group contains one, two or three heteroatoms selected from the group consisting of oxygen, nitrogen and sulphur and which may optionally be mono-, di- or tri-substituted by one or more of the groups $C_1$–$C_4$-alkyl, phenyl or benzyl;

$R^4$ denotes hydrogen, $C_1$–$C_6$-alkyl, which may be mono- or disubstituted by one or more of the groups COOH, COO—$C_1$–$C_4$-alkyl or $C_3$–$C_6$-cycloalkyl, or phenyl-$C_1$–$C_4$-alkyl, wherein the $C_1$–$C_4$-alkylene bridge may optionally be substituted by phenyl and wherein the phenyl ring may optionally be mono-, di- or tri-substituted by one or more of the groups $C_1$–$C_4$-alkyl, $C_1$–$C_4$-alkoxy, $CF_3$, fluorine, chlorine, bromine, COOH or COO—$C_1$–$C_4$-alkyl, or $C_3$–$C_8$-cycloalkyl, naphthyl or phenyl, which may optionally be mono-, di- or tri-substituted by one or more of the groups $C_1$–$C_4$-alkyl, $C_1$–$C_4$-alkoxy, phenyloxy, benzyloxy, $CF_3$, fluorine, chlorine, bromine, COOH or COO—$C_1$–$C_4$-alkyl, or a 5-, 6- or 7-membered, saturated or unsaturated heterocyclic group linked via a $C_1$–$C_4$-alkylene bridge, which heterocyclic group contains one heteroatom selected from the group consisting of oxygen, nitrogen and sulphur and which may optionally be mono-, di- or tri-substituted by one or more of the groups $C_1$–$C_4$-alkyl, phenyl or benzyl or to which a benzene ring may optionally be fused via two adjacent carbon atoms, or $R^3$ and $R^4$ together with the nitrogen atom form a 5-, 6- or 7-membered, saturated or unsaturated heterocyclic group, which heterocyclic group optionally contains one or two further heteroatoms selected from the group consisting of oxygen, nitrogen and sulphur and may optionally be substituted by one or more of the groups $C_1$–$C_4$-alkyl, benzyl, which is optionally $C_1$–$C_4$-alkyl-substituted, $C_5$–$C_6$-cycloalkyl, pyridyl or phenyl, which optionally bears a group selected from the group consisting of $C_1$–$C_4$-alkyl, $C_1$–$C_4$-alkoxy and hydroxy, or a tautomer or pharmaceutically acceptable salt thereof.

4. A compound of the formula (I) according to claim 3, wherein:
$R^1$ denotes unsubstituted $C_1$–$C_{10}$-alkyl, or may be mono- or disubstituted by $C_1$–$C_4$-alkoxy, phenoxy, $C_1$–$C_4$-alkoxy-phenoxy, hydroxyphenoxy, $C_3$–$C_6$-cycloalkyl, —$NH_2$, —NH($C_1$–$C_4$-alkyl), —N($C_1$–$C_4$-alkyl)$_2$, —NH—CO—($C_1$–$C_4$-alkyl), —CO—$NH_2$, —CO—NH—($C_1$–$C_4$-alkyl) or —NH—CO—benzyl substituted $C_1$–$C_4$-alkyl, or phenyl-$C_1$–$C_3$-alkyl, wherein the phenyl ring may optionally be mono- or disubstituted by $C_1$–$C_4$-alkyl, $CF_3$, fluorine, chlorine, bromine, COOH or COO—$C_1C_4$-alkyl, or a 5-, 6- or 7-membered, saturated or unsaturated heterocyclic group linked via a $C_1$–$C_3$-alkylene bridge, which heterocyclic group contains one or two heteroatoms selected from the group consisting of oxygen, nitrogen and sulphur and may optionally be mono- or disubstituted by one or more of the groups methyl, ethyl, propyl, phenyl, methylphenyl- or benzyl or to which a benzene ring may optionally be fused via two adjacent carbon atoms;

$R^2$ denotes —C(=NH)$NH_2$ or —$CH_2$—$NH_2$;

$R^3$ denotes $C_1$–$C_6$-alkyl, which is mono- or disubstituted by one or more of the groups —$NH_2$, —NH($C_1$–$C_4$-alkyl), —N($C_1$–$C_4$-alkyl)$_2$, —NHphenyl, —N(phenyl)$_2$, —NHbenzyl, —N(benzyl)$_2$, —NH—CO—($C_1C_4$-alkyl), —C(=NH)$NH_2$ or —NH—C(=NH)$NH_2$, or benzyl, wherein the phenyl ring is substituted directly or via a $C_1$–$C_4$-alkylene bridge by one of the groups —$NH_2$, —NH($C_1$–$C_4$-alkyl), —N($C_1$–$C_4$-alkyl)$_2$, —NHphenyl, —N(phenyl)$_2$, —NHbenzyl, —N(benzyl)$_2$, —NH—CO—(C$_1$–C$_4$-alkyl), —C(=NH)NH$_2$ or —NH—C(=NH)NH$_2$, or phenyl-C$_2$–C$_4$-alkyl, wherein the C$_2$–C$_4$-alkylene bridge may optionally be substituted by phenyl, COOH or COO—C$_1$–C$_4$-alkyl and wherein the phenyl ring may be substituted directly or via a C$_1$–C$_4$-alkylene bridge by one of the groups —NH$_2$, —NH(C$_1$–C$_4$-alkyl), —N(C$_1$–C$_4$-alkyl)$_2$, —NHphenyl, —(phenyl)$_2$, —NHbenzyl, —N(benzyl)$_2$, —C(=NH)NH$_2$ or —NH—C(=NH)NH$_2$, or a 5-, 6- or 7-membered, saturated or unsaturated heterocyclic group linked via a C$_1$–C$_4$-alkylene bridge, which heterocyclic group contains one or two heteroatoms selected from the group consisting of oxygen and nitrogen and may optionally be mono- or disubstituted by one or more of the groups methyl, ethyl, propyl, phenyl or benzyl;

R$^4$ denotes hydrogen, C$_1$–C$_4$-alkyl, which may be substituted by one of the groups COOH, COO—C$_1$–C$_4$-alkyl or C$_3$–C$_6$-cycloalkyl, or phenyl-C$_1$–C$_4$-alkyl, wherein the C$_1$–C$_4$-alkylene bridge may optionally be substituted by phenyl and wherein the phenyl ring may optionally be mono- or disubstituted by one or more of the groups C$_1$–C$_4$-alkyl, C$_1$–C$_4$-alkoxy, CF$_3$, fluorine, chlorine, bromine, COOH or COO—C$_1$–C$_4$-alkyl, or C$_3$–C$_8$-cycloalkyl, naphthyl or phenyl, which may optionally be mono- or disubstituted by one or more of the groups C$_1$–C$_4$-alkyl, C$_1$–C$_4$-alkoxy, phenyloxy, benzyloxy, CF$_3$, fluorine, chlorine, bromine, COOH or COO—C$_1$–C$_4$-alkyl, or a 5-, 6- or 7-membered, saturated or unsaturated heterocyclic group linked via a C$_1$–C$_4$-alkylene bridge, which heterocyclic group contains one heteroatom selected from the group consisting of oxygen, nitrogen and sulphur and which may optionally be mono- or disubstituted by one or more of the groups methyl, ethyl, propyl, phenyl or benzyl or to which a benzene ring may optionally be fused via two adjacent carbon atoms, or R$^3$ and R$^4$ together with the nitrogen atom form a 6- or 7-membered, saturated or unsaturated heterocyclic group, which contains one or two further heteroatoms selected from the group consisting of oxygen and nitrogen and which may optionally be substituted by one or more of the groups methyl, ethyl, propyl, benzyl, cyclopentyl, cyclohexyl, pyridyl or phenyl, which optionally carries a group selected from the group consisting of methyl, methoxy, ethoxy, propyloxy and hydroxy, or a tautomer or pharmaceutically acceptable salt thereof.

5. A compound of the formula (I) according to claim 3, wherein:

R$^1$ denotes unsubstituted C$_1$–C$_{10}$-alkyl, or by C$_1$–C$_4$-alkoxy, phenoxy, C$_1$–C$_4$-alkoxy-phenoxy, hydroxyphenoxy, C$_3$–C$_6$-cycloalkyl, —NH$_2$, —NH(C$_1$–C$_4$-alkyl), —N(C$_1$–C$_4$-alkyl)$_2$, —NH—CO—(C$_1$–C$_4$-alkyl), —CO—NH$_2$, —CO—NH—(C$_1$–C$_4$-alkyl) or —NH—CO—benzyl substituted C$_1$–C$_4$-alkyl, or phenyl-C$_1$–C$_3$-alkyl, wherein the phenyl ring may optionally be mono- or disubstituted by C$_1$–C$_4$-alkyl, CF$_3$, fluorine, chlorine, bromine, COOH or COO—C$_1$–C$_4$-alkyl, or a heterocyclic group linked via a C$_1$–C$_3$-alkylene bridge, optionally mono- or disubstituted by one or more of the groups methyl, ethyl, propyl, phenyl, methylphenyl or benzyl, selected from the group consisting of pyrrole, pyrroline, pyrrolidine, pyridine, piperidine, pyrimidine, piperazine, morpholine, thiomorpholine, imidazole, imidazoline, imidazolidine, pyrazole, pyrazoline, pyrazolidine, triazole, furan, tetrahydrofuran, α-pyran, γ-pyran, dioxolan, tetrahydropyran, dioxane, thiophene, dihydrothiophene, thiolan, dithiolan, oxazole, isoxazole, thiazole, isothiazole, oxadiazole, benzodioxole, benzimidazole, benzothiophene, benzofuran and indole;

R$^2$ denotes —C(=NH)NH$_2$ or —CH$_2$—NH$_2$; R$^3$ denotes C$_1$–C$_3$-alkyl, which is substituted by —NH$_2$, —NH(C$_1$–C$_3$-alkyl), —N(C$_1$–C$_3$alkyl)$_2$, —NHphenyl, —N(phenyl)$_2$, —NHbenzyl, —N(benzyl)$_2$, —NH—CO—(C$_1$–C$_3$-alkyl), —C(=NH)NH$_2$ or —NH—C(=NH)NH$_2$, or benzyl, wherein the phenyl ring is substituted directly or via a methylene bridge by one of the groups —NH$_2$, —NH(C$_1$–C$_3$-alkyl), —N(C$_1$–C$_4$-alkyl)$_2$, —NHphenyl, —N(phenyl)$_2$, —NHbenzyl, —N(benzyl)$_2$, —H—CO—(C$_1$–C$_3$-alkyl), —C(=NH)NH$_2$ or —NH—C(=NH)NH$_2$, or phenyl-C$_2$—C$_3$-alkyl, wherein the C$_2$–C$_3$-alkylene bridge may optionally be substituted by phenyl, COOH or COO—C$_1$–C$_3$-alkyl and wherein the phenyl ring may be substituted directly or via a methylene bridge by one of the groups —NH$_2$, —NH(C$_1$–C$_3$-alkyl), —N(C$_1$–C$_3$-alkyl)$_2$, —NHphenyl, —N(phenyl)$_2$, —NHbenzyl, —N(benzyl)$_2$, —C(=NH)NH$_2$ or —NH—C(=NH)NH$_2$, or a heterocyclic group linked via a C$_1$–C$_3$-alkylene bridge, optionally mono- or disubstituted by one or more of the groups methyl, ethyl, propyl, phenyl or benzyl, selected from the group consisting of pyrrole, pyrroline, pyrrolidine, pyridine, piperidine, pyrimidine, piperazine morpholine, diazepan, imidazole, imidazoline, imidazolidine, pyrazole, pyrazoline, pyrazolidine, furan, tetrahydrofuran, α-pyran, γ-pyran, dioxolan, tetrahydropyran, dioxane, oxazole and isoxazole;

R$^4$ denotes hydrogen, C$_1$–C$_4$-alkyl, which may be substituted by one of the groups COOH, COO—C$_1$–C$_3$-alkyl or C$_3$–C$_6$-cycloalkyl, or phenyl-C$_1$–C$_3$-alkyl, wherein the C$_1$–C$_3$-alkylene bridge may optionally be substituted by phenyl and wherein the phenyl ring may optionally be substituted by C$_1$–C$_3$-alkyl, C$_1$–C$_3$-alkoxy, CF$_3$, fluorine, chlorine, bromine, COOH or COO—C$_1$–C$_3$-alkyl, or C$_3$–C$_8$-cycloalkyl, naphthyl or phenyl, which may optionally be mono- or disubstituted by one or more of the groups C$_1$–C$_3$-alkyl, C$_1$–C$_3$-alkoxy, phenyloxy, benzyloxy, CF$_3$, fluorine, chlorine, bromine, COOH or COO—C$_1$–C$_3$-alkyl, or a heterocyclic group linked via a C$_1$–C$_3$-alkylene bridge, optionally mono- or disubstituted by one or more of the groups methyl, ethyl, propyl, phenyl, methylphenyl- or benzyl, selected from the group consisting of pyrrole, pyrroline, pyrrolidine, pyridine, piperidine, pyrimidine, piperazine morpholine, thiomorpholine, imidazole, imidazoline, imidazolidine, pyrazole, pyrazoline, pyrazolidine, triazole, furan, tetrahydrofuran, α-pyran, γ-pyran, dioxolan, tetrahydropyran, dioxane, thiophene, dihydrothiophene, thiolan, dithiolan, oxazole, isoxazole, thiazole, isothiazole, oxadiazole, benzodioxole, benzimidazole, benzothiophene, benzofuran and indole; or R³ and R⁴ together with the nitrogen atom form a 6- or 7-membered, saturated heterocyclic group, which contains one or two further nitrogen heteroatoms and which may optionally be substituted by one or more of the groups methyl, ethyl, propyl, benzyl, cyclopentyl, cyclohexyl, pyridyl or phenyl, which optionally carries a group selected from the group consisting of methyl, methoxy, ethoxy, propyloxy and hydroxy, or a pharmaceutically acceptable salt thereof.

6. A compound of the formula (I) according to claim 3, wherein:

$R^1$ denotes methyl, ethyl, propyl, butyl, pentyl, hexyl, heptyl, octyl, nonyl or decyl, or a methyl, ethyl or propyl group which is substituted by methoxy, ethoxy, cyclopropyl, cyclopentyl, cyclohexyl, phenyl, methoxyphenoxy, —NH₂, —NH(C₁-C₄-alkyl), —N(C₁-C₄-alkyl)₂, —NH—CO-methyl, —CO—NH₂, —CO—NH-methyl or —NH—CO-benzyl, or benzyl, which is mono- or disubstituted by methyl, ethyl, propyl, CF₃, fluorine, chlorine, bromine, COOH, COOMe or COOEt, or phenylethyl, which is mono- or disubstituted by methyl, ethyl, propyl, CF₃, fluorine, chlorine, bromine, COOH, COOMe or COOEt, or a heterocyclic group linked via a methylene, ethylene or propylene bridge, optionally mono- or disubstituted by one or more of the groups methyl, ethyl, propyl, phenyl, methylphenyl or benzyl, selected from the group consisting of pyrrole, pyrrolidine, pyridine, piperidine, piperazine, morpholine, furan, tetrahydrofuran, thiophene, benzodioxole and benzimidazole;

$R^2$ denotes —C(=NH)NH₂ or —CH₂—NH₂;

$R^3$ denotes a methyl, ethyl or propyl group which is substituted by —NH₂, —NH(C₁-C₃-alkyl), —N(C₁-C₃-alkyl)₂, —NHphenyl, —N(phenyl)₂, —NHbenzyl, —N(benzyl)₂, —NH—CO—(C₁-C₃-alkyl), —NH-benzyl or —C(=NH)NH₂, or benzyl, which is substituted directly or via a methylene bridge by one of the groups —NH₂, —NH(C₁-C₃-alkyl), —N(C₁-C₄-alkyl)₂, —NHphenyl, —N(phenyl)₂, —NHbenzyl, —N(benzyl)₂, —NH—CO—(C₁-C₃-alkyl) or —C(=NH)NH₂, or phenyl-C₂-C₃-alkyl, wherein the C₂-C₃-alkylene bridge may optionally be substituted by phenyl, COOH or COO—C₁-C₃-alkyl and wherein the phenyl ring may be substituted directly or via a methylene bridge by one of the groups —NH₂, —NH(C₁-C₃-alkyl), —N(C₁-C₃-alkyl)₂, —NHphenyl, —N(phenyl)₂, —NHbenzyl, —N(benzyl)₂ or —C(=NH)NH₂, or a heterocyclic group linked via a methylene, ethylene or propylene bridge, optionally mono- or disubstituted by methyl, ethyl, propyl, phenyl or benzyl, selected from the group consisting of pyrrole, pyrrolidine, pyridine, piperidine, piperazine, morpholine, diazepan, furan, tetrahydrofuran, thiophene, benzodioxole and benzimidazoles;

$R^4$ denotes hydrogen or a methyl, ethyl, propyl or butyl group which may be substituted by one of the groups COOH, COOMe, COOEt, cyclopropyl, cyclopentyl or cyclohexyl, or benzyl, which may optionally be substituted by methyl, ethyl, propyl, methoxy, ethoxy, CF₃, fluorine, chlorine, bromine, COOH, COOMe or COOEt, or phenylethyl, phenylpropyl, diphenylpropyl;

cyclopropyl, cyclopentyl, cyclohexyl, cyclooctyl, naphthyl or phenyl, which may optionally be substituted by methyl, ethyl, propyl, methoxy, ethoxy, phenyloxy, benzyloxy, CF₃, fluorine, chlorine, bromine, COOH, COOMe or COOEt, or a heterocyclic group linked via a methylene, ethylene or propylene bridge, optionally mono- or disubstituted by methyl, ethyl, propyl, phenyl or benzyl, selected from the group consisting of pyrrole, pyrrolidine, pyridine, piperidine, piperazine, morpholine, furan, tetrahydrofuran, thiophene, quinoline, isoquinoline, benzodioxole and benzimidazole; or R³ and R⁴ together with the nitrogen atom form a piperazine or diazepan ring which may optionally be substituted by one of the groups methyl, ethyl, propyl, cyclopentyl, cyclohexyl, pyridyl, benzyl or phenyl, which optionally carries a group selected from the group consisting of methyl, methoxy, ethoxy, propyloxy and hydroxy, or a tautomer or pharmaceutically acceptable salt thereof.

7. A compound of the formula (I) according to claim 3, wherein:

$R^1$ denotes methyl, ethyl, propyl, pentyl or n-decyl, or a methyl, ethyl- or propyl group which is substituted by methoxy, ethoxy, cyclopropyl, cyclopentyl, cyclohexyl, phenyl or methoxyphenoxy, or benzyl, which is mono- or disubstituted by methyl, CF₃, COOH, COOMe or COOEt, or a tetrahydrofuran linked via a methylene bridge;

$R^2$ denotes —C(=NH)NH₂ or —CH₂—NH₂;

$R^3$ denotes an ethyl or propyl group which is substituted by —NH₂, —NHMe, —NMe₂, —NHEt, —NEt₂, —NHphenyl, —N(phenyl)₂, —NHbenzyl, —N(benzyl)₂ or —C(=NH)NH₂, or Benzyl which is substituted by one of the groups —NH₂, —CH₂—NH₂, —NMe₂, —NHMe, —NEt₂, —NHEt, —NH—CO-Me, —CH₂—NH—CO-Me or —C(=NH)NH₂, or phenylethyl, wherein the ethylene bridge may be substituted by COOH, COOMe or COOEt and wherein the phenyl ring is optionally substituted by one of the groups —NH₂, —CH₂—NH₂, —NMe₂, —NHMe, —NEt₂, —NHEt, —NH—CO-Me, —CH₂—NH—CO-Me or —C(=NH)NH₂, or phenylpropyl, diphenylpropyl or pyridylmethyl;

$R^4$ denotes hydrogen or a methyl, ethyl, propyl or butyl group, which may be substituted by one of the groups COOH, COOMe, COOEt, cyclopropyl, cyclopentyl or cyclohexyl, or benzyl, which may optionally be substituted by methyl, ethyl, propyl, methoxy, ethoxy, CF₃, fluorine, chlorine, bromine, COOH, COOMe or COOEt, or phenyl-ethyl, phenylpropyl, diphenylpropyl, or cyclopentyl, cyclohexyl, cyclooctyl, naphthyl or phenyl, which may optionally be substituted by methyl, ethyl, methoxy, ethoxy, phenyloxy or CF₃, or a pyridine or quinoline linked via a methylene bridge, or R³ and R⁴ together with the nitrogen atom form a piperazine or diazepan ring, which may optionally be substituted by one of the groups cyclopentyl, cyclohexyl, pyridyl, benzyl or phenyl, which optionally carries one of the groups selected from the group consisting of methyl, methoxy, ethoxy, propyloxy and hydroxy, or a tautomer or pharmaceutically acceptable salt thereof.

8. A compound of the formula (I) according to claim 3, wherein:

$R^1$ denotes methyl, ethyl, propyl, pentyl, phenylethyl, phenylpropyl, cyclopropylmethyl, tetrahydrofuranylmethyl or benzyl, which is mono- or disubstituted by $CF_3$, COOH, COOMe or COOEt;

$R^2$ denotes —C(=NH)$NH_2$ or —$CH_2$—$NH_2$, preferably —C(=NH)$NH_2$;

$R^3$ denotes an ethyl or propyl group which is substituted by —$NH_2$, —NHMe, —$NMe_2$, —NHEt, —$NEt_2$, —NHphenyl, —N(phenyl)$_2$, —NHbenzyl, —N(benzyl)$_2$ or —C(=NH)$NH_2$, or benzyl substituted by one of the groups —$NH_2$, —$CH_2$—$NH_2$, —$NMe_2$, —NHMe, —$NEt_2$, —NHEt, —NH—CO-Me, —$CH_2$—NH—CO-Me or —C(=NH)$NH_2$, or phenylethyl, wherein the ethylene bridge is substituted by COOH, COOMe or COOEt and wherein the phenyl ring carries one of the groups —$NH_2$, —$CH_2$—$NH_2$, —$NMe_2$, —NHMe, —$NEt_2$, —NHEt, —NH—CO-Me, —$CH_2$—NH—CO-Me or —C(=NH)$NH_2$, or phenylpropyl, diphenylpropyl or pyridylmethyl;

$R^4$ denotes hydrogen or a methyl, ethyl, propyl or butyl group which may be substituted by one of the groups COOH, COOMe, COOEt or cyclohexyl, or phenyl, which may optionally be substituted by methyl, ethyl, methoxy, ethoxy, phenyloxy or $CF_3$, or benzyl, phenylethyl, phenylpropyl, diphenylpropyl, cyclohexyl, cyclooctyl or naphthyl, or a pyridine or quinoline linked via a methylene bridge, or $R^3$ and $R^4$ together with the nitrogen atom form a piperazine or diazepan ring, which may optionally be substituted by one of the groups cyclopentyl, cyclohexyl, pyridyl, benzyl or phenyl, which optionally carries a group selected from the group consisiting of methyl, methoxy, ethoxy, propyloxy and hydroxy, or a tautomer or pharmaceutically acceptable salt thereof.

9. A compound of the formula (I) according to claim 3, wherein:

$R^1$ denotes methyl;

$R^2$ denotes —C(=NH)$NH_2$ or —$CH_2$—$NH_2$, preferably —C(=NH)$NH_2$;

$R^3$ denotes ethyl, substituted by —$NH_2$, —$NMe_2$, —NHphenyl, —NHbenzyl, —N(benzyl)$_2$, pyrrolidine, piperidine, diazepan or —C(=NH)$NH_2$, benzyl substituted by one of the groups —$CH_2$—$NH_2$, —$NMe_2$ or —C(=NH)$NH_2$, phenylethyl, wherein the ethylene bridge is substituted by COOH, COOMe or COOEt and wherein the phenyl ring carries one of the groups —$CH_2$—NH—CO-Me or —C(=NH)$NH_2$, diphenylpropyl or pyridylmethyl;

$R^4$ denotes hydrogen or a methyl or ethyl group which may optionally be substituted by one of the groups COOH or COOEt; propyl, butyl or phenyl, which may optionally be substituted by methyl, ethyl, methoxy, ethoxy, phenyloxy or $CF_3$; benzyl, phenylethyl, phenylpropyl, diphenylpropyl, cyclohexyl, cyclooctyl, naphthyl, pyridylmethyl or quinolinylmethyl or $R^3$ and $R^4$ together with the nitrogen atom form a piperazine or diazepan ring substituted by one of the groups benzyl, cyclopentyl, cyclohexyl or phenyl, which optionally carries a group selected from the group consisting of methyl, ethoxy, propyloxy and hydroxy, or a tautomer or pharmaceutically acceptable salt thereof.

10. A compound of the formula I, according to claim 3, wherein:

$R^1$ denotes methyl;

$R^2$ denotes —C(=NH)$NH_2$;

$R^3$ denotes ethyl, substituted by —$NH_2$, —NHphenyl, —NHbenzyl, —N(benzyl)$_2$, pyrrolidine, piperidine, diazepan or —C(=NH)$NH_2$ ; benzyl substituted by —C(=NH)$NH_2$ , or diphenylpropyl;

$R^4$ denotes hydrogen, methyl, propyl, butyl, benzyl or phenyl, which may optionally be substituted by ethyl or phenyloxy; phenylethyl, cyclohexyl or cyclooctyl, or $R^3$ and $R^4$ together with the nitrogen atom form a piperazine ring which is substituted by a group selected from the group consisting of cyclopentyl, cyclohexyl, phenyl, methylphenyl, ethoxyphenyl and propoxyphenyl, or a diazepan ring substituted by methylphenyl, or a tautomer or pharmaceutically acceptable salt thereof.

11. A compound of the formula I, according to claim 3, wherein:

$R^1$ denotes methyl;

$R^2$ denotes —C(=NH)$NH_2$;

$R^3$ denotes ethyl, substituted by —$NH_2$, —NHbenzyl, —N(benzyl)$_2$, pyrrolidine, piperidine, diazepan or —C(=NH)$NH_2$, benzyl substituted by —C(=NH)$NH_2$, or diphenylpropyl;

$R^4$ denotes hydrogen, methyl, butyl or phenyl, which may optionally be substituted by ethyl or phenyloxy; phenylethyl, cyclohexyl or cyclooctyl, or a tautomer or pharmaceutically acceptable salt thereof.

12. A compound of the formula (II)

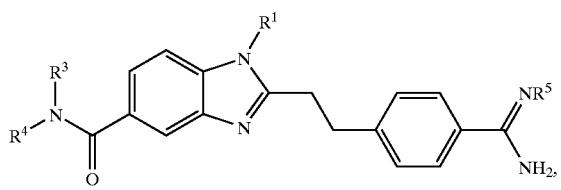

(II)

wherein $R^1$ and $R^4$ are defined as in claim 3 and $R^3$ may have the meanings given in claim 3 or denotes $C_1$-$C_4$-alkyl, which is substituted by a group selected from the group consisting of —C(=NOH)$NH_2$, —C(=NCOO—$C_1$-$C_4$-alkyl)$NH_2$ and —C(=NCOO—$C_1$-$C_4$-alkyl-phenyl)$NH_2$;

$R^5$ denotes hydroxy, —COO—$C_1$-$C_8$-alkyl or —COO—$C_1$-$C_4$-alkyl-phenyl, whilst in the abovementioned group the phenyl ring may be substituted by $C_1$-$C_4$-alkyl or $C_1$-$C_4$-alkoxy, or a tautomer or pharmaceutically acceptable salt thereof.

13. A compound of the formula II, according to claim 12, wherein:

$R^1$ and $R^4$ have the meanings given in claim 3;

$R^3$ has the meanings given in claim 3, or denotes $C_1$-$C_4$-alkyl, which is substituted by a group selected from the group comprising —C(=NOH)$NH_2$, —C(=NCOOmethyl)$NH_2$, —C(NCOOethyl)$NH_2$, —C(=NCOOpropylyl)$NH_2$ or —C(=NCOO-benzyl)$NH_2$;

$R^5$ denotes hydroxy, methoxycarbonyl, ethoxycarbonyl, propyloxycarbonyl, butyloxycarbonyl, pentyloxycarbonyl, hexyloxycarbonyl, or benzyloxycarbonyl;

or a tautomer or pharmaceutically acceptable salt thereof.

14. A compound of the formula (III)

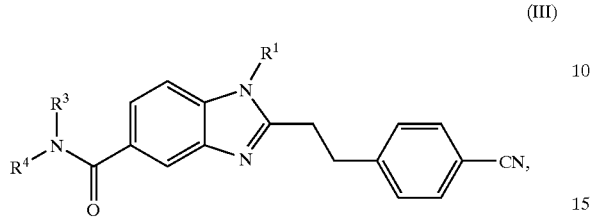

(III)

wherein the groups $R^1$, $R^3$ and $R^4$ have the meanings given in claim 3.

15. A pharmaceutical composition comprising a compound of the formula I, in accordance with claim 3.

16. A pharmaceutical composition comprising a compound of the formula II, in accordance with claim 12.

17. A compound of the formula (I)

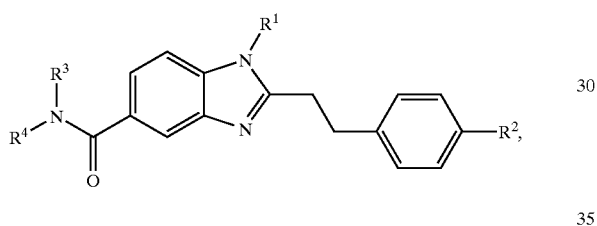

(I)

wherein:

$R^1$ denotes methyl, ethyl, propyl, butyl, pentyl, hexyl, heptyl, octyl, nonyl or decyl, or a methyl, ethyl or propyl group which is substituted by methoxy, ethoxy, cyclopropyl, cyclopentyl, cyclohexyl, phenyl, methoxyphenoxy, —$NH_2$, —$NH(C_1$–$C_4$alkyl), —$N(C_1$–$C_4$-alkyl)$_2$, —NH—CO-methyl, —CO—$NH_2$, —CO—NH-methyl or —NH—CO-benzyl, or benzyl, which is mono- or disubstituted by methyl, ethyl, propyl, $CF_3$, fluorine, chlorine, bromine, COOH, COOMe or COOEt, or phenylethyl, which is mono- or disubstituted by methyl, ethyl, propyl, $CF_3$, fluorine, chlorine, bromine, COOH, COOMe or COOEt, or a heterocyclic group linked via a methylene, ethylene or propylene bridge, optionally mono- or disubstituted by one or more of the groups methyl, ethyl, propyl, phenyl, methylphenyl or benzyl, selected from the group consisting of pyrrole, pyrrolidine, pyridine, piperidine, piperazine, morpholine, furan, tetrahydrofuran, thiophene, benzodioxole and benzimidazole;

$R^2$ denotes —C(=NH)$NH_2$ or —$CH_2$—$NH_2$;

$R^3$ denotes a methyl, ethyl or propyl group which is substituted by —$NH_2$, —NH($C_1$–$C_3$alkyl), —N($C_1$–$C_3$-alkyl)$_2$, —NHphenyl, —N(phenyl)$_2$, —NHbenzyl, —N(benzyl)$_2$, —NH—CO—($C_1$–$C_3$-alkyl), —NH-benzyl or —C(=NH)$NH_2$, or benzyl, which is substituted directly or via a methylene bridge by one of the groups —$NH_2$, —NH($C_1$–$C_3$-alkyl), —N($C_1$–$C_4$-alkyl)$_2$, —NHphenyl, —N(phenyl)$_2$, —NHbenzyl, —N(benzyl)$_2$, —NH—CO—($C_1$–$C_3$-alkyl) or —C(=NH)$NH_2$, or phenyl-$C_2$–$C_3$-alkyl, wherein the $C_2$–$C_3$-alkylene bridge may optionally be substituted by phenyl, COOH or COO—$C_1$–$C_3$-alkyl and wherein the phenyl ring may be substituted directly or via a methylene bridge by one of the groups —$NH_2$, —NH($C_1$–$C_3$-alkyl), —N($C_1$–$C_3$-alkyl)$_2$, —NHphenyl, —N(phenyl)$_2$, —NHbenzyl, —N(benzyl)$_2$ or —C(=NH)$NH_2$, or a heterocyclic group linked via a methylene, ethylene or propylene bridge, optionally mono- or disubstituted by methyl, ethyl, propyl, phenyl or benzyl, selected from the group consisting of pyrrole, pyrrolidine, pyridine, piperidine, piperazine, morpholine, diazepan, furan, tetrahydrofuran, thiophene, benzodioxole and benzimidazoles;

$R^4$ denotes hydrogen or a methyl, ethyl, propyl or butyl group which may be substituted by one of the groups COOH, COOMe, COOEt, cyclopropyl, cyclopentyl or cyclohexyl, or benzyl, which may optionally be substituted by methyl, ethyl, propyl, methoxy, ethoxy, $CF_3$, fluorine, chlorine, bromine, COOH, COOMe or COOEt, or phenylethyl, phenylpropyl, diphenylpropyl;

cyclopropyl, cyclopentyl, cyclohexyl, cyclooctyl, naphthyl or phenyl, which may optionally be substituted by methyl, ethyl, propyl, methoxy, ethoxy, phenyloxy, benzyloxy, $CF_3$, fluorine, chlorine, bromine, COOH, COOMe or COOEt, or a heterocyclic group linked via a methylene, ethylene or propylene bridge, optionally mono- or disubstituted by methyl, ethyl, propyl, phenyl or benzyl, selected from the group consisting of pyrrole, pyrrolidine, pyridine, piperidine, piperazine, morpholine, furan, tetrahydrofuran, thiophene, quinoline, isoquinoline, benzodioxole and benzimidazole; or $R^3$ and $R^4$ together with the nitrogen atom form a piperazine or diazepan ring which may optionally be substituted by one of the groups methyl, ethyl, propyl, cyclopentyl, cyclohexyl, pyridyl, benzyl or phenyl, which optionally carries a group selected from the group consisting of methyl, methoxy, ethoxy, propyloxy and hydroxy, or a tautomer or pharmaceutically acceptable salt thereof.

* * * * *